(12) United States Patent
Morioka et al.

(10) Patent No.: US 7,928,126 B2
(45) Date of Patent: Apr. 19, 2011

(54) CYANOPYRIDINE DERIVATIVE AND USE THEREOF AS MEDICINE

(75) Inventors: Masahiko Morioka, Osaka (JP); Hiroshi Ikegami, Osaka (JP); Makoto Sakiyama, Osaka (JP); Masayuki Hayashi, Osaka (JP); Shinsuke Ooike, Osaka (JP); Yasuhiro Fujino, Osaka (JP); Daisuke Abe, Osaka (JP); Hideo Tomozane, Osaka (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 581 days.

(21) Appl. No.: 11/919,173

(22) PCT Filed: Apr. 28, 2006

(86) PCT No.: PCT/JP2006/308937
§ 371 (c)(1),
(2), (4) Date: Nov. 29, 2007

(87) PCT Pub. No.: WO2006/118231
PCT Pub. Date: Nov. 9, 2006

(65) Prior Publication Data
US 2009/0292121 A1    Nov. 26, 2009

(30) Foreign Application Priority Data
Apr. 28, 2005  (JP) ................... 2005-131498

(51) Int. Cl.
*A61K 31/4439* (2006.01)
*C07D 401/14* (2006.01)
(52) U.S. Cl. ...................... 514/333; 546/256
(58) Field of Classification Search .................. 546/256; 514/333
See application file for complete search history.

(56) References Cited

U.S. PATENT DOCUMENTS
2005/0256102 A1   11/2005  Claiborne et al.

FOREIGN PATENT DOCUMENTS
| JP | 2002-95479 | 4/2002 |
|---|---|---|
| WO | 01/21595 | 3/2001 |
| WO | 02/22601 | 3/2002 |
| WO | 02/066461 | 8/2002 |
| WO | 03/055491 | 7/2003 |
| WO | 2005/013996 | 2/2005 |

OTHER PUBLICATIONS

Vippagunta et al., "Crystalline Solid", Advanced Drug Delivery Reviews 48 (2001) 3-26.*
Guillory (in Brittain ed.), "Polymorphism, etc.," NY: Marcel Dekker, Inc., 1999, 1-2, 183-226.*
I. Melnikova et al., "Targeting Protein Kinases", Nat. Rev. Drug Discovery, vol. 3, pp. 993-994, Dec. 2004.

D. M. Glover et al., "Mutations in *aurora* Prevent Centrosome Separation Leading to the formation of Monopolar Spindles", Cell, vol. 81, pp. 95-105, Apr. 7, 1995.
D. Berdnik et al., "Drosophila Aurora-A is Required for Centrosome Maturation and Actin-Dependent Asymmetric Protein Localization During Mitosis", Current Biology, vol. 12, pp. 640-647, Apr. 16, 2002.
H. Zhou et al., "Tumour Amplified Kinase STK15/BTAK Induces Centrosome Amplification, Aneuploidy and Transformation", Nature Genetics, vol. 20, pp. 189-193, Oct. 20, 1998.
T. Tanaka et al., "Centrosomal Kinase AIK1 is Overexpressed in Invasive Ductal Carcinoma of the Breast", Cancer Research, vol. 59, pp. 2041-2044, May 1, 1999.
C. Sakakura et al., "Tumour-Amplified Kinase BTAK is Amplified and Overexpressed in Gastric Cancers with Possible Involvement in Aneuploid Formation", British Journal of Cancer, vol. 84, No. 6, pp. 824-831, 2001.
S. Sen et al., "Amplification/Overexpression of a Mitotic Kinase Gene in Human Bladder Cancer", Journal of the National Cancer Institute, vol. 94, No. 17, pp. 1320-1329, Sep. 4, 2002.
D. Li et al., "Overexpression of Oncogenic STK15/BTAK/Aurora A Kinase in Human Pancreatic Cancer", Clinical Cancer Research, vol. 9, pp. 991-997, Mar. 2003.
Y. M. Jeng et al., "Overexpression and Amplification of Aurora-A in Hepatocellular Carcinoma", Clinical Cancer Research, vol. 10, pp. 2065-2071, Mar. 15, 2004.
S. Rojanala et al., "The Mitotic Serine Threonine Kinase, *Aurora-2* is a Potential Target for Drug Development in Human Pancreatic Cancer", Molecular Cancer Therapeutics, vol. 3, No. 4, pp. 451-457, 2004.
J. R. Bischoff et al., "A Homologue of *Drosophila aurora* Kinase is Oncogenic and Amplified in Human Colorectal Cancers", The EMBO Journal, vol. 17, No. 11, pp. 3052-3065, 1998.
E. A. Harrington et al., "VX-680, A Potent and Selective Small-Molecule Inhibitor of the Aurora Kinases, Suppresses Tumor Growth In Vitro", Nature Medicine, vol. 10, No. 3, pp. 262-267, 2004.
N. Keen et al., "Aurora-Kinase Inhibitors as Anticancer Agents", Nature Reviews Cancer, vol. 4, No. 12, pp. 927-936, Dec. 2004.
D. Fancelli et al., "Potent and Selective Aurora Inhibitors Identified by the Expansion of a Novel Scaffold for Protein Kinase Inhibition", J. Med. Chem., vol. 48, pp. 3080-3084, 2005.
R. R. Adams et al., "Human INCENP Colocalizes with the Aurora-B/AIRK2 Kinase on Chromosomes and is Overexpressed in Tumor Cells", Chromosoma, vol. 110, No. 2, pp. 65-74, 2001.
W. Fischle et al., "Regulation of HP1-Chromatin Binding by Histone H3 Methylation and Phosphorylation", Nature, vol. 438, pp. 1116-1122, Dec. 2005.
T. Hirota et al., "Histone H3 Serine 10 Phosphorylation by Aurora B Causes HP1 Dissociation from Heterochromatin", Nature, vol. 438, pp. 1176-1180, Dec. 2005.

(Continued)

*Primary Examiner* — Patricia L Morris
(74) *Attorney, Agent, or Firm* — Wenderoth, Lind & Ponack, LLP.

(57) ABSTRACT

A therapeutic drug for cancer containing a substance selected from the group consisting of a novel cyanopyridine derivative, a pharmaceutically acceptable salt, a hydrate, a water adduct and a solvate as an active ingredient can be provided.

9 Claims, No Drawings

OTHER PUBLICATIONS

J. J. Manfredi et al., "Taxol Binds to Cellular Microtubules", The Journal of Biology, vol. 94, pp. 688-696, Sep. 1982.

I. Durko et al., "Effects of Two Microtubule-Depolymerizing Drugs, Vincristine and Vinblastine, on Porphyrin Production by Primary Neural Tissue Cultures" Neurochemical Research, vol. 15, No. 11, pp. 1135-1139, 1990.

P. B. Schiff et al., "Promotion of Microtubule Assembly In Vitro by Taxol", Nature, vol. 277, pp. 665-667, 1979.

Chinese Office Action issued Mar. 10, 2010, in corresponding Chinese Application No. 200680014451 8.4, with English translation.

Response to Chinese Office Action (2010), with English translation.

\* cited by examiner

CYANOPYRIDINE DERIVATIVE AND USE THEREOF AS MEDICINE

This application is a U.S. national stage of International Application No. PCT/JP2006/308937 filed Apr. 28, 2006.

TECHNICAL FIELD

The present invention relates to a novel cyanopyridine derivative and a pharmaceutical agent comprising the same as an active ingredient.

BACKGROUND ART

Protein kinase is considered a drug target as important as GPCR (G protein-coupled receptor). Abnormal activation of protein kinase is related to a number of diseases associated with cell overgrowth. Examples thereof include inflammatory and proliferative diseases, namely, what is called an overgrowth disorder, such as tumor, rheumatoid arthritis, cardiac disease, neurotic disease, psoriasis, asthma, angiogenesis and intravascular smooth muscle growth in postoperative stenosis or restenosis. Abnormality in protein kinase is said to be directly and indirectly involved in 400 kinds of human diseases, and therefore, once the activity of protein kinase can be controlled, various diseases are considered to be effectively treated. However, there are only a few compounds marketed as pharmaceutical products (non-patent reference 1).

It has been clarified that a protein phosphorylation reaction is extremely important for the mitotic progress of the cells causing cancer, genetic disease and the like, where a series of serine/threonine kinases called mitotic protein kinases play the role. Mitotic protein kinase phosphorylate substrate of various proteins at particular timing and site, whereby accurate mitosis proceeds. However, once the control thereof collapses, abnormality occurs in various events in the M-phase such as chromosome separation, causing radical character change of the cells. One of those mitotic protein kinases is aurora kinase. Aurora kinase is a highly-preserved serine/threonine kinase, which is expressed in the M phase of the cell cycle, and therefore, is considered an important enzyme for the progress of the M phase. It is highly preserved from yeast to human. There are human homologues of aurora 1-3: aurora 2 kinase and aurora 1 kinase are ubiquitously present in various cells but aurora 3 kinase is localized in testis. A gene encoding aurora 2 kinase is present on the long arm of chromosome 20, and this region relates to many cancers. The significance of the kinase family in the M phase has also been suggested by a function inhibitory experiment of aurora 2 kinase homologous gene using yeast, *Drosophila* and *Caenorhabditis elegans* (non-patent reference 2 and non-patent reference 3).

In addition, there have been clarified as facts that aurora 2 kinase is overexpressed in many cancers (non-patent reference 4, non-patent reference 5, non-patent reference 6, non-patent reference 7, non-patent reference 8, non-patent reference 9 and non-patent reference 10) and experimental overexpression of aurora 2 kinase in normal cell results in the cell showing a sign of malignant transformation (non-patent reference 11).

Furthermore, it has been documented that a treatment of human proliferative cell lines with antisense oligonucleotide suppresses expression of aurora 2 kinase, thus inhibiting growth of the cell (patent reference 1). This is considered to suggest that abnormal cell growth can be suppressed by the inhibition of aurora 2 kinase activity, which is useful for the treatment of a number of diseases associated with abnormal cell growth, such as cancer.

Some low molecular weight compounds inhibiting Aurora 2 kinase have been reported in patent reference and the like. For example, patent reference 2, patent reference 3, patent reference 4, patent reference 5, patent reference 6, patent reference 7, non-patent reference 12, non-patent reference 13 and non-patent reference 14 can be mentioned.

In addition, there are many reports relating to the involvement of aurora 1 kinase in cancer. For example, non-patent reference 15, non-patent reference 16, non-patent reference 17 can be mentioned. In the M-phase of cell cycle, duplicated chromosomes are equally separated into two daughter cells. In the M-phase, microtubules (tubulin polymerization products) form spindle bodies, which play a key role in the physical migration of chromosomes. Accordingly, tubulin polymerization and depolymerization play an important role in chromosome migration, and further, cell division. Paclitaxel, vincristine and the like widely used clinically as antitumor drugs are known to be pharmaceutical agents that act on tubulin and inhibit depolymerization and polymerization thereof (see non-patent references 18 and 19). It is considered that they consequently provoke M-phase arrest in the cell cycle (see non-patent reference 20), and show an antitumor action.

patent reference 1: JP-A-2002-95479
patent reference 2: WO2001-21595
patent reference 3: WO2002-22601
patent reference 4: WO2002-66461
patent reference 5: WO2003-55491
patent reference 6: WO2005-013996
patent reference 7: US-A-2005-0256102
non-patent reference 1: Irena Melnikova et al., Nature Reviews/Drug Discovery, vol. 3, pages 993-994, 2004
non-patent reference 2: David M. Glover et al., Cell, vol. 81, pages 95-105, 1995
non-patent reference 3: Daniela Berdnik et al., Current Biology, vol. 12, pages 640-647, 2002
non-patent reference 4: Hongyi Zhou et al., Nature Genetics, vol. 20, pages 189-193, 1998
non-patent reference 5: Takuji Tanaka et al., Cancer Research, vol. 59, pages 2041-2044, 1999
non-patent reference 6: C. Sakakura et al., British Journal of Cancer, vol. 84, pages 824-831, 2001
non-patent reference 7: Subrata Sen et al., Journal of the National Cancer Institute, vol. 94, pages 1320-1329, 2002
non-patent reference 8: Donghui Li et al., Clinical Cancer Research, vol. 9, pages 991-997, 2003
non-patent reference 9: Yung-Ming Jeng et al., Clinical Cancer Research, vol. 10, pages 2065-2071, 2004
non-patent reference 10: Sangeeta Rojanala et al., Molecular Cancer Therapeutics, vol. 3, No. 4, pages 451-457, 2004
non-patent reference 11: James R. Bischoff et al., EMBO Journal, vol. 17, pages 3052-3065, 1998
non-patent reference 12: Elizabeth A. Harrington et al., Nature Medicine, vol. 10, No. 3, pages 262-267, 2004
non-patent reference 13: Nicolas Keen et al., Nature Reviews Cancer, vol. 4, pages 927-936, 2004
non-patent reference 14: Daniele Faucelli et al., J. Med. Chem, vol. 48, pages 3080-3084, 2005
non-patent reference 15: Adams et al., Chromsoma, vol. 110, No. 2, pages 65-74, 2001
non-patent reference 16: W. Fischle et al., Nature, vol. 438, pages 1116-1122, 2005
non-patent reference 17: T. Hirota et al., Nature, vol. 438 pages 1176-1180, 2005 non-patent reference 18: Manfredi J. J.; Parness J.; Horwitz S. B. J. Cell Biol. 1982, 94, 688-696.
non-patent reference 19: Durko I.; Juhasz A. Neurochem. Res. 1990, 15, 1135-1139.
non-patent reference 20: Schiff P. B.; Fant J.; Horwitz S. B. Nature 1979, 227(5698), 665-667.

DISCLOSURE OF THE INVENTION

Problems to be Solved by the Invention

An object of the present invention is to provide a therapeutic drug for cancer, which has an aurora kinase inhibitory action and/or a tubulin polymerization inhibitory action.

Means of Solving the Problems

The present inventors have conducted intensive studies in an attempt to solve the aforementioned problems and found that a cyanopyridine derivative represented by the following formula (I), a pharmaceutically acceptable salt, a hydrate, a water adduct and a solvate show an aurora kinase inhibitory effect and/or a tubulin polymerization inhibitory effect, and have a strong anti-cancer effect. The present invention has been completed based on the above-mentioned findings.

Accordingly, the present invention provides the following.

(1) A cyanopyridine derivative represented by the formula (I)

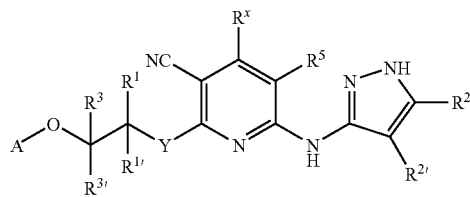

wherein $R^1$, $R^{1\prime}$, $R^3$, $R^{3\prime}$ and $R^5$ are each a hydrogen atom, a halogen atom or alkyl,
$R^2$ is a hydrogen atom, a hydroxyl group, alkyl, alkoxy, hydroxyalkyl, alkylthio, carbamoyl, alkanoylamino or amine,
$R^{2\prime}$ is a hydrogen atom or alkyl, or $R^2$ and $R^{2\prime}$ are taken together to form a 5- to 7-membered cyclic compound,
Y is N—$R^4$ or S,
$R^4$ is a hydrogen atom or alkyl,
A is aryl or heteroaryl,
$R^x$ is -T-$R^4$,
T is a valence bond or a $C_{1-4}$ alkylene chain, and
$R^4$ is —R, a halogen atom, —OR or —$NR_2$ wherein R is a hydrogen atom, alkyl, aryl, heteroaryl or heterocycle, or $R^x$ and $R^5$ are taken together to form a 5- to 7-membered cyclic compound, or a pharmaceutically acceptable salt, hydrate, water adduct or solvate thereof.
(2) The cyanopyridine derivative of the aforementioned (1), wherein, in the above-mentioned formula (I), T is a valence bond, $R^4$ is alkyl, aryl, heteroaryl or heterocycle, and A is aryl or heteroaryl, or a pharmaceutically acceptable salt, hydrate, water adduct or solvate thereof.
(3) The cyanopyridine derivative of the aforementioned (1) or (2), wherein, in the above-mentioned formula (I), $R^4$ is alkyl, phenyl, pyridyl, piperidyl or thienyl, and A is phenyl, pyridyl or pyrimidyl, or a pharmaceutically acceptable salt, hydrate, water adduct or solvate thereof.
(4) A prophylactic and/or therapeutic agent for cancer, which comprises a cyanopyridine derivative of the aforementioned (1)-(3), or a pharmaceutically acceptable salt, hydrate, water adduct or solvate thereof.
(5) A cyanopyridine derivative represented by the following formula (III)

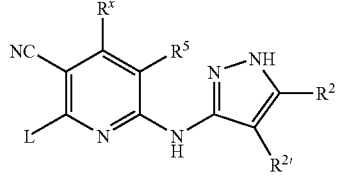

wherein L is a halogen atom, and $R^2$, $R^{2\prime}$, $R^5$ and $R^x$ are as defined above, or a pharmaceutically acceptable salt, hydrate, water adduct or solvate thereof.
(6) The cyanopyridine derivative of the aforementioned (5), which is selected from the group consisting of the following compounds, or a pharmaceutically acceptable salt, hydrate, water adduct or solvate thereof:
2-chloro-6-(5-methyl-1H-pyrazol-3-ylamino)-4-methyl nicotinonitrile,
2-chloro-6-(5-methyl-1H-pyrazol-3-ylamino)-4-phenyl nicotinonitrile,
2-chloro-6-(5-methyl-1H-pyrazol-3-ylamino)-4-(4-methoxyphenyl)nicotinonitrile,
2-chloro-6-(5-methyl-1H-pyrazol-3-ylamino)-4-(pyridin-3-yl)nicotinonitrile,
6-(5-methyl-1H-pyrazol-3-ylamino)-2-chloronicotinonitrile,
2-chloro-6-(5-methyl-1H-pyrazol-3-ylamino)-4-(trifluoromethyl)nicotinonitrile,
2-chloro-6-(5-methyl-1H-pyrazol-3-ylamino)-4,4'-bipyridine-3-carbonitrile,
2-chloro-6-(5-methyl-1H-pyrazol-3-ylamino)-4-(3,4,5-trimethoxyphenyl)nicotinonitrile,
2-chloro-4-(3-methoxyphenyl)-6-(5-methyl-1H-pyrazol-3-ylamino)nicotinonitrile,
2-chloro-4-(2-methoxyphenyl)-6-(5-methyl-1H-pyrazol-3-ylamino)nicotinonitrile,
4-(1,3-benzodioxol-5-yl)-2-chloro-6-(5-methyl-1H-pyrazol-3-ylamino)nicotinonitrile,
2-chloro-6-(5-methyl-1H-pyrazol-3-ylamino)-4-(2-thienyl)nicotinonitrile,
2-chloro-6-(5-methyl-1H-pyrazol-3-ylamino)-4-(3-methyl-2-thienyl)nicotinonitrile,
2-chloro-6-(5-methyl-1H-pyrazol-3-ylamino)-4-(5-methyl-2-thienyl)nicotinonitrile,
2-chloro-4-(4-isopropyloxyphenyl)-6-(5-methyl-1H-pyrazol-3-ylamino)nicotinonitrile,
2-chloro-6-(5-cyclopropyl-1H-pyrazol-3-ylamino)-4-methylnicotinonitrile,
2-chloro-6-(5-isopropyl-1H-pyrazol-3-ylamino)-4-methylnicotinonitrile
2-chloro-4-ethyl-6-(5-methyl-1H-pyrazol-3-ylamino)nicotinonitrile,
2-chloro-6-(5-ethyl-1H-pyrazol-3-ylamino)-4-methylnicotinonitrile,
2-chloro-5-methyl-6-(5-methyl-1H-pyrazol-3-ylamino) nicotinonitrile,
2-chloro-5-fluoro-6-(5-methyl-1H-pyrazol-3-ylamino)nicotinonitrile, 2-chloro-4-cyclopropyl-6-(5-methyl-1H-pyrazol-3-ylamino)nicotinonitrile,
2-chloro-6-(5-methyl-1H-pyrazol-3-ylamino)-4-(3-morpholin-4-ylpropyl)nicotinonitrile,
2-1-(5-methyl-1H-pyrazol-3-ylamino)6,7-dihydro-5H-cyclopenta(c)pyridine-4-carbonitrile,
2-chloro-4-methyl-6-(5-(methylthio)-1H-pyrazol-3-ylamino)nicotinonitrile,
2-chloro-6-(5-cyclopropyl-1H-pyrazol-3-ylamino)nicotinonitrile, tert-butyl 4-(2-chloro-3-cyano-6-(5-methyl-1H-pyrazol-3-ylamino)pyridine-1-carboxylate,
2-chloro-6-(5-ethoxy-1H-pyrazol-3-ylamino)-4-methylnicotinonitrile,
2-chloro-4-(4-isobutylphenyl-6-(5-methyl-1H-pyrazol-3-ylamino)nicotinonitrile,
2-chloro-4-isopropyl-6-(5-methyl-1H-pyrazol-3-ylamino)nicotinonitrile,
2-chloro-6-(5-methylthio-1H-pyrazol-3-ylamino)nicotinonitrile,
2-chloro-4-methyl-6-(1H-pyrazol-3-ylamino)nicotinonitrile, and
4-(1-acetylpiperidin-4-yl)-2-chloro-6-(5-methyl-1H-pyrazol-3-ylamino)nicotinonitrile.

(7) An inhibitor of aurora kinase and/or tubulin polymerization, comprising, as an active ingredient, a cyanopyridine derivative of any of the aforementioned (1)-(3), or a pharmaceutically acceptable salt, hydrate, water adduct or solvate thereof.

EFFECT OF THE INVENTION

The present invention can provide a therapeutic drug for cancer, comprising, as an active ingredient, a substance selected from the group consisting of a cyanopyridine derivative represented by the above-mentioned formula (I), a pharmaceutically acceptable salt, a hydrate, a water adduct and a solvate.

BEST MODE FOR EMBODYING THE INVENTION

The present invention is explained in detail in the following.

Each substituent represented by the above-mentioned formula (I) of the present invention is defined below.

Examples of the "halogen atom" for $R^1$, $R^{1'}$, $R^3$, $R^{3'}$ or $R^5$ include a fluorine atom.

Examples of the "alkyl" for $R^1$, $R^{1'}$, $R^3$, $R^{3'}$ or $R^5$ include $C_{1-6}$ alkyl (e.g., methyl, ethyl, propyl, isopropyl, cyclopropyl, butyl, isobutyl, sec-butyl, tert-butyl, pentyl, hexyl etc.), and $C_{1-3}$ alkyl (e.g., methyl, ethyl, propyl, isopropyl) is particularly preferable.

Examples of the "alkyl" for $R^2$ or $R^{2'}$ include those similar to the "alkyl" for the aforementioned $R^1$.

Examples of the "alkylthio" for $R^2$ include alkylthio wherein the alkyl moiety is similar to the "alkyl" for the aforementioned $R^1$, such as methylthio, ethylthio, propylthio, isopropylthio, cyclopropylthio, butylthio and the like.

Examples of the "alkoxy" for $R^2$ include methoxy, ethoxy, isopropoxy and the like.

Examples of the "hydroxyalkyl" for $R^2$ include hydroxymethyl, hydroxyethyl and the like.

Examples of the "carbamoyl" for $R^2$ include methylcarbamoyl, ethylcarbamoyl and the like.

Examples of the "alkanoylamino" for $R^2$ include acetylamino, pivaloylamino and the like.

Examples of the "amine" for $R^2$ include dimethylamine, diethylamine and the like.

Examples of the "5- to 7-membered cyclic compound" formed by $R^2$ and $R^{2'}$ in combination include benzene, pyridine, pyrimidine, indole, pyrrolidine, piperidine, morpholine, homopiperidine, tetrahydrothiophene and the like.

Examples of the "alkyl" for $R^A$ include those similar to the "alkyl" for the aforementioned $R^1$.

The alkyl for $R^1$, $R^{1'}$, $R^2$, $R^{2'}$, $R^3$, $R^{3'}$ or $R^A$ is optionally substituted by a suitable substituent. Examples of the "substituent" include a halogen atom (e.g., fluorine atom, chlorine atom, bromine atom, iodine atom), $C_{1-6}$ alkyl (methyl, ethyl, propyl, isopropyl, butyl, isobutyl, sec-butyl, tert-butyl, pentyl, hexyl), haloalkyl (fluoromethyl, difluoromethyl, trifluoromethyl, 2-fluoroethyl, 2,2-difluoroethyl, 2,2,2-trifluoroethyl etc.), cyano, nitro, hydroxy, $C_{1-6}$ alkoxy (methoxy, ethoxy, propoxy, isopropoxy, butoxy, tert-butoxy etc.), mercapto, $C_{1-6}$ alkylthio (methylthio, ethylthio, n-propylthio, isopropylthio, n-butylthio etc.), amino, $C_{1-6}$ alkylamino (methylamino, ethylamino, n-propylamino, isopropylamino, n-butylamino, dimethylamino, diethylamino, N-methyl-N-ethylamino etc.) and the like.

Examples of the "aryl" for A include phenyl, 1-naphthyl, 2-naphthyl and the like, with preference given to phenyl.

Examples of the "heteroaryl" for A include 5- or 6-membered heteroaryl containing, besides carbon atom, one or two kinds of 1 to 4 hetero atoms selected from nitrogen atom, sulfur atom and oxygen atom (e.g., thienyl, furyl, pyrrolyl, imidazolyl, pyrazolyl, pyridyl, pyrazinyl, pyrimidinyl, thiazolyl, oxazolyl, triazolyl, benzothienyl, indolyl, quinazolyl, N-oxopyridyl etc.).

The aryl and heteroaryl for A are optionally substituted by suitable substituent(s). Examples of the "substituent" include halogen atom (e.g., fluorine, chlorine, bromine, iodine), $C_{1-6}$ alkyl (methyl, ethyl, propyl, isopropyl, butyl, isobutyl, sec-butyl, tert-butyl, pentyl, hexyl), haloalkyl (fluoromethyl, difluoromethyl, trifluoromethyl, 2-fluoroethyl, 2,2-difluoroethyl, 2,2,2-trifluoroethyl etc.), cyano, nitro, hydroxy, $C_{1-6}$ alkoxy (methoxy, ethoxy, propoxy, isopropoxy, butoxy, tert-butoxy etc.), mercapto, $C_{1-6}$ alkylthio (methylthio, ethylthio, n-propylthio, isopropylthio, n-butylthio etc.), amino, $C_{1-6}$ alkylamino (methylamino, ethylamino, n-propylamino, isopropylamino, n-butylamino, dimethylamino, diethylamino, N-methyl-N-ethylamino etc.), $C_{2-6}$ alkanoylamino (acetylamino, propionylamino etc.), $C_{1-6}$ alkanesulfonylamino (methanesulfonylamino, ethanesulfonylamino etc.), 5- to 7-membered cyclic compound (e.g., piperidine, piperazine, pyrrolidine, morpholine, thiomorpholine etc.), carboxyl (methylcarboxyl, ethylcarboxyl etc.), carbamoyl (methylcarbamoyl, ethylcarbamoyl etc.), alkylcarbonyl (methylcarbonyl, ethylcarbonyl) and the like. These substituents are optionally further substituted by the above-mentioned substituent(s).

The "$C_{1-4}$ alkylene chain" for T is a divalent group derived from straight chain or branched chain saturated hydrocarbon having 1 to 4 carbon atoms. Specific examples include methylene, ethylene, propylene and the like.

Examples of the "halogen atom" for $R_4$ include those similar to the "halogen atom" for the aforementioned $R^1$.

Examples of the "alkyl" for R include those similar to the "alkyl" for the aforementioned $R^1$, with preference given to methyl, trifluoromethyl and the like.

Examples of the "aryl" for R include those similar to the "aryl" for the aforementioned A, with preference given to phenyl.

Examples of the "heteroaryl" for R include those similar to the "heteroaryl" for the aforementioned A, with preference given to pyridine and the like.

Examples of the "heterocycle" for R include 5- to 7-membered heterocycle containing, besides carbon atom, one or two kinds of 1 to 3 hetero atoms selected from nitrogen atom, sulfur atom and oxygen atom (e.g., piperidine, piperazine, pyrrolidine, morpholine, thiomorpholine etc.).

The alkyl, aryl, heteroaryl and heterocycle for R are optionally substituted by suitable substituent(s). Examples of the "substituent" include halogen atom (e.g., fluorine, chlorine, bromine, iodine), $C_{1-6}$ alkyl (methyl, ethyl, propyl, isopropyl, butyl, isobutyl, sec-butyl, tert-butyl, pentyl, hexyl), haloalkyl (fluoromethyl, difluoromethyl, trifluoromethyl, 2-fluoroethyl, 2,2-difluoroethyl, 2,2,2-trifluoroethyl etc.), cyano, nitro, hydroxy, $C_{1-6}$ alkoxy (methoxy, ethoxy, propoxy, isopropoxy, butoxy, tert-butoxy etc.), mercapto, $C_{1-6}$ alkylthio (methylthio, ethylthio, n-propylthio, isopropylthio, n-butylthio etc.), amino, $C_{1-6}$ alkylamino (methylamino, ethylamino, n-propylamino, isopropylamino, n-butylamino, dimethylamino, diethylamino, N-methyl-N-ethylamino etc.), $C_{2-6}$ alkanoylamino (acetylamino, propionylamino etc.), $C_{1-6}$ alkanesulfonylamino (methanesulfonylamino, ethanesulfonylamino etc.), 5- to 7-membered cyclic compound (e.g., piperidine, piperazine, pyrrolidine, morpholine, thiomorpholine etc.), carboxyl (methylcarboxyl, ethylcarboxyl etc.), carbamoyl (methylcarbamoyl, ethylcarbamoyl etc.), alkylcarbonyl (methylcarbonyl, ethylcarbonyl) and the like. These substituents are optionally further substituted by the above-mentioned substituent(s).

In the formula (I), Y is preferably NH or S, and is particularly preferably NH.

Examples of the pharmaceutically acceptable salt of the compound of the formula (I) include acid addition salts with inorganic acid or organic acid.

The pharmaceutically acceptable salt of the compound of the formula (I) may present as a water adduct, a hydrate or a solvate, and such water adduct, hydrate and solvate are also encompassed in the present invention.

An optically active form of the compound of the formula (I) is also encompassed in the present invention.

The compound of the present invention encompassed in the formula (I) can be synthesized by the following methods.

In the following reaction scheme, each symbol is as defined above unless otherwise specified.

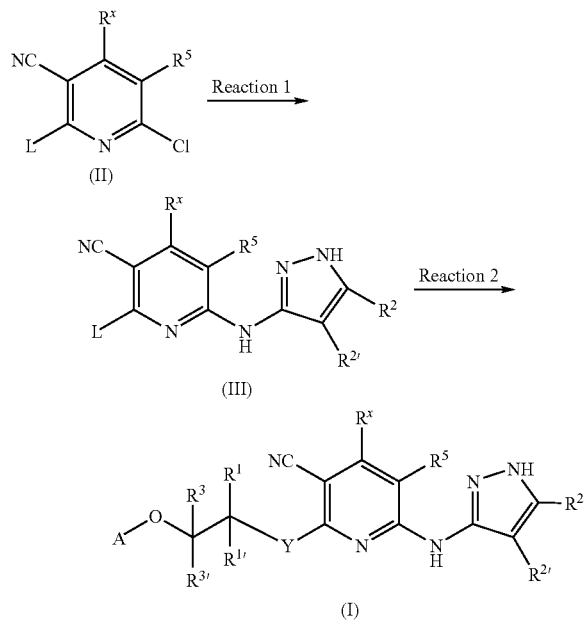

As a production starting material of the compound of the formula (I) according to the present invention, a 2,6-dihalo-3-cyanopyridine derivative of the formula (II) is used. The starting compound can be produced by a known method. ((1) J. Org. Chem., Vol. 25, p 560 (2) JP-A-49-62477 (3) Bioorg Med Chem Lett, 11 (2001) p 475 (4) J. Org. Chem., 44 (1979) p 2693). Alternatively, the compound can be easily synthesized by reacting the corresponding β-ketoester with 2-cyanoacetamide in the presence of DBU (diazabicyclo[5,4,0]undecene), and heat-treating the precipitate with phenylphosphonic dichloride. In reaction 1, a compound of the formula (II) and a 3-aminopyrazole derivative are reacted in the presence of a base in a suitable solvent at room temperature or under heating to give a compound of the formula (III). When the base is absent, the reaction proceeds thermally by raising the reaction temperature, whereby compound (III) can be obtained.

The above-mentioned base is not particularly limited as long as it can accelerate the reaction, and tertiary amine, metal alkoxide such as potassium-tert-butoxide and the like, diazabicyclo[5,4,0]undecane, amidine, guanidine, metal hydride such as sodium hydride and the like, metal fluoride such as potassium fluoride and the like, a solid carrying metal fluoride, and the like can be used. Particularly, tertiary amine (triethylamine, Hunig's Base) is preferable.

The amount of the base to be added is generally 0.1-30 equivalents, preferably 1-10 equivalents, relative to the compound.

While the solvent to be used for the reaction is not limited as long as it does not inhibit the reaction, it is preferably tetrahydrofuran (hereinafter to be referred to as THF), dimethyl sulfoxide (hereinafter to be referred to as DMSO), 1,4-dioxane, N,N-dimethylformamide (hereinafter to be referred to as DMF) and the like.

The reaction temperature of this reaction is generally from 20° C. to 200° C., preferably from 80° C. to 150° C.

While the reaction time varies depending on the temperature or the kind of the solvent, it is generally 30 min-8 hr.

Similar reaction proceeds with a compound wherein nitrogen of pyrazole of the compound of the formula (III) has been protected with a general protecting group, whereby a corresponding protected compound of the formula (III) can be obtained, which may be later deprotected to also give a compound of the formula (III).

After completion of the above-mentioned reaction, the objective product of each reaction can be obtained from the reaction mixture according to a conventional method. For example, the reaction mixture is concentrated, or when a solid is present, the solid is removed by filtration as appropriate, and the solution is added to basic or neutral water to allow crystallization, whereby the objective product can be obtained. When the objective product does not crystallize, the objective product can be obtained by washing with an organic solvent (e.g., ethyl acetate, chloroform) immiscible with water, separating an organic layer containing the objective product, drying the layer over anhydrous magnesium sulfate etc. and evaporating the solvent.

Where necessary, the obtained object compound can be further purified by a conventional method, for example, recrystallization, reprecipitation, washing with solvent, chromatography and the like.

In reaction 2, a compound of the formula (III) and an amine derivative or thiol derivative are reacted in the presence of a base in a suitable solvent under heating to give a compound of the formula (I). When the base is absent, the reaction proceeds thermally by raising the reaction temperature, whereby compound (I) can be obtained.

The above-mentioned base is not particularly limited as long as it can accelerate the reaction, and tertiary amine, metal alkoxide such as potassium-tert-butoxide and the like, diazabicyclo[5,4,0]undecane, amidine, guanidine, metal hydride such as sodium hydride and the like, sodium hydrogencarbonate and the like can be used. Sodium bicarbonate is particularly preferable.

The amount of the base to be added is generally 0.1-30 equivalents, preferably 1-10 equivalents, relative to the compound.

While the solvent to be used for the reaction is not limited as long as it does not inhibit the reaction, it is preferably THF, DMSO, 1,4-dioxane, DMF and the like.

The reaction temperature of this reaction is generally from 60° C. to 200° C., preferably from 80° C. to 150° C.

While the reaction time varies depending on the temperature or the kind of the solvent, it is generally 1 hr-100 hr.

Similar reaction proceeds with a compound wherein nitrogen of pyrazole of the compound of the formula (III) has been protected with a general protecting group, whereby a corresponding protected compound of the formula (I) can be obtained, which may be later deprotected to also give a compound of the formula (I).

After completion of the above-mentioned reaction, the objective product of each reaction can be obtained from the reaction mixture according to a conventional method. For example, the reaction mixture is concentrated, or when a solid is present, the solid is removed by filtration as appropriate, and the solution is added to water to allow crystallization, whereby the objective product can be obtained. When the objective product does not crystallize, the objective product can be obtained by washing with an organic solvent (e.g., ethyl acetate, chloroform) immiscible with water, separating an organic layer containing the objective product, drying the layer over anhydrous magnesium sulfate etc. and evaporating the solvent.

The cyanopyridine derivative of the formula (I) of the present invention produced in this way can be obtained at any purity by applying a known separation and purification means as appropriate, for example, concentration, extraction, chromatography, reprecipitation, recrystallization and the like.

A salt, a hydrate and a solvate of the cyanopyridine derivative of the formula (I) can be produced from the cyanopyridine derivative by a known method.

The compound of the formula (I) obtained by the above-mentioned method, or a pharmaceutically acceptable salt, hydrate, water adduct or solvate thereof has a strong aurora kinase inhibitory action and/or tubulin polymerization inhibitory action, as well as an anti-cancer action, and is useful as a prophylactic and/or therapeutic drug for cancer.

The compound of the present invention, an optical isomer thereof or a pharmaceutically acceptable salt thereof are low toxic and can be used safely. The dose thereof can be appropriately determined according to the conditions of patients such as age, general condition, body weight and the like, and when a pharmaceutical agent is to be administered simultaneously, the conditions such as the kind thereof, administration frequency and the like, or property of the desired effect and the like. In general, a daily dose of the active ingredient is 0.5-300 mg/kg body weight, generally 1-30 mg/kg body weight, which can be administered in one or more portions per day.

When the compound of the present invention is used as a pharmaceutical agent, a pharmaceutical composition containing the above-mentioned active ingredient and one or more kinds of additives for preparation is preferably formulated and administered.

Examples of the pharmaceutical composition suitable for administration include tablets, capsules, powders, solutions, elixirs and the like, and examples of the pharmaceutical composition suitable for parenteral administration include sterile liquid pharmaceutical composition such as solutions, suspensions and the like.

The kind of the additives for formulation to be used for preparation of a pharmaceutical composition is not particularly limited, and appropriate additives for preparation making can be selected according to various forms of the pharmaceutical composition. The additives for formulation may be solid or liquid and, for example, solid carrier, liquid carrier and the like can be used. Examples of the solid carrier include general gelatin type capsules. Moreover, for example, the active ingredient can be tableted together with one or more kinds of additives for formulation or without using an additive for formulation, or can be prepared as a powder and encapsulated. Such capsule, tablet and powder can generally contain the active ingredient in a proportion of 5-95 wt %, preferably 5-90 wt %, relative to the whole weight of the preparation, and an administration unit form preferably contains 5-500 mg, preferably 25-250 mg, of the active ingredient. As a liquid carrier, water, or animal or plant oil such as petroleum, peanut oil, soybean oil, mineral oil, sesame oil, or synthetic oil and the like can be used.

In general, moreover, saline, dextrose or related sucrose solution, and glycols such as ethylene glycol, propylene glycol, polyethylene glycol and the like are preferable as a liquid carrier. Particularly, an injection using saline can be prepared to contain generally 0.5-20%, preferably 1-10% by weight, of the active ingredient.

EXAMPLES

The present invention is explained in more detail in the following by referring to Examples and Pharmacological Experimental Examples, which are not to be construed as limitative.

The chemical shift of 1H-NMR was expressed as relative delta (δ) value in parts per million (ppm) using tetramethylsilane (TMS) as the internal standard. For the coupling constant, obvious multiplicity is shown using s (singlet), d (doublet), t (triplet), m (multiplet), dd (double doublet), brs (broad singlet) and the like in hertz (Hz). Thin-layer chromatography was performed using silica gel manufactured by Merck, and column chromatography was performed using silica gel manufactured by Fuji Silysia Chemical.

In addition, organic solution in extraction was dried over anhydrous sodium sulfate or anhydrous magnesium sulfate, unless otherwise specified.

Reference Example 1

Synthesis of 2,6-dichloro-4-phenylnicotinonitrile

To a suspension of ethyl 3-oxo-3-phenyl-propionate (18 g: 94 mmol) and 2-cyanoacetamide (7.9 g: 94 mmol) in 2-propanol was added diazabicyclo[5,4,0]undecene (hereinafter to be referred to as DBU, 14 mL), and the mixture was heated under reflux for 22 hr, allowed to cool to room temperature. 1N-Hydrochloric acid solution (140 mL) was added, and the insoluble substance was filtrated to give a solid (9.4 g). This was dissolved in phenylphosphonic dichloride (150 mL), and the mixture was heated at 182° C. for 4.5 hr. The reaction mixture was allowed to cool to room temperature, and poured into cool water (700 mL). The insoluble substance was collected by filtration, dried, and dissolved in a chloroform:

ethanol solution (1 L, 1:1). The solution was treated with activated carbon, and concentrated, and the obtained residue was crystallized from ethanol to give 2,6-dichloro-4-phenylnicotinonitrile (10.7 g, yield: 28%).

$^1$H-NMR (300 MHz, DMSO-d$_6$) δ(ppm): 7.79 (s, 1H), 7.73-7.68 (m, 2H), 7.60-7.55 (m, 3H)

Reference Example 2

Synthesis of 2',6'-dichloro-3,4'-bipyridine-3'-carbonitrile

To a solution of ethyl 3-oxo-3-pyridin-3-yl-propionate (10.5 g, 54 mmol) and 2-cyanoacetamide (6 g, 65 mmol) in ethanol was added DBU (9 mL, 60 mmol), and the mixture was heated under reflux for 12 hr. The insoluble substance was collected by filtration to give a solid (5.8 g). 4.65 g of these was dissolved in phenylphosphonic dichloride at 180° C., and the mixture was treated for 3 hr. The reaction mixture was allowed to cool to room temperature, and poured into cool water (600 mL). This mixture was neutralized with 1N-sodium hydroxide solution, and the insoluble substance was collected by filtration. The filtrate was extracted with ethyl acetate, and the extract was concentrated to dryness. The obtained solid and the above insoluble substance were combined, and dissolved in methanol. The solution was treated with activated carbon, and concentrated to give 2',6'-dichloro-3,4'-bipyridine-3'-carbonitrile (2.44 g).

$^1$H-NMR (300 MHz, DMSO-d$_6$) δ(ppm): 8.86 (s, 1H), 8.77 (d-like, 1H), 8.14 (d, 1H), 8.07 (s, 1H), 7.62 (t-like, 1H)

Reference Example 3

Synthesis of 2,6-dichloro-4-(2-thienyl)nicotinonitrile

To a solution of ethyl 3-oxo-3-(2-thienyl)propionate (87 g, 390 mmol) and 2-cyanoacetamide (34 g, 410 mmol) in ethanol was slowly added potassium hydroxide (22 g) with stirring under heating. The mixture was heated under reflux for 72 hr, and allowed to cool to room temperature, and the insoluble substance was collected by filtration to give a solid (43 g). This solid was slowly added to phenylphosphonic dichloride, and the mixture was treated at 180° C. for 5 hr. The mixture was allowed to cool to room temperature, and poured into cool water. The insoluble substance was collected by filtration, thoroughly washed with saturated aqueous sodium hydrogencarbonate solution, dried, and dissolved in chloroform. The solution was treated with activated carbon, and concentrated, and the residue was crystallized from 2-propanol:ethyl acetate mixture to give 2,6-dichloro-4-(2-thienyl)nicotinonitrile (8.6 g).

$^1$H-NMR (300 MHz, DMSO-d$_6$) δ(ppm): 8.1-8.0 (m, 3H), 7.33 (t, 1H)

Reference Example 4

Synthesis of 2,6-dichloro-4-cyclopropyl-nicotinonitrile

To a solution of ethyl 3-cyclopropyl-3-oxopropionate (99 g, 635 mmol) and 2-cyanoacetamide (54 g, 635 mmol) in 2-propanol was added DBU (95 mL), and the mixture was heated under reflux for 58 hr, allowed to cool to room temperature, and poured into 1N hydrochloric acid (1 L). The resulting insoluble substance was collected by filtration (solid A). 3.48 g of these was added to phenylphosphonic dichloride, and the mixture was treated at 130° C. for 10 hr. The insoluble substance was collected by filtration and washed with ethanol to give 2,6-dichloro-4-cyclopropyl-nicotinonitrile (1.4 g).

$^1$H-NMR (300 MHz, DMSO-d$_6$) δ(ppm): 7.30 (s, 1H), 2.2-2.1 (m, 1H), 1.32-1.26, 1.14-1.10 (each m, each 2H)

Reference Example 5

Synthesis of 2,6-dichloro-4-(3-(morpholin-4-yl)propyl)nicotinonitrile

The solid A (11 g) obtained in Reference Example 4 was treated with phenylphosphonic dichloride (150 mL) at 180° C. for 22 hr, and the mixture was allowed to cool to room temperature, and poured into cool water. The clayish insoluble substance was collected by filtration, and purified by silica gel column chromatography to give a solid (2,6-dichloro-4-(3-chloropropyl)nicotinonitrile) (8 g). 1 g of these was dissolved in dichloromethane and the solution was reacted with morpholine (0.4 mL) in the presence of triethylamine (hereinafter to be referred TEA, 1.22 mL). The reaction mixture was purified by silica gel column chromatography to give 2,6-dichloro-4-(3-(morpholin-4-yl)propyl)nicotinonitrile (740 mg) as white crystals.

$^1$H-NMR (300 MHz, DMSO-d$_6$) δ(ppm): 6.82 (s, 1H) 3.7-3.6 (m, 10H), 2.76 (dd, 2H), 2.1-2.0 (m, 2H)

Reference Example 6

Synthesis of tert-butyl 4-(2,6-dichloro-3-cyanopyridin-4-yl)piperidine-1-carboxylate To a solution of tert-butyl 4-(3-ethoxy-3-oxopropanoyl)piperidine-1-carboxylate (104 g, 349 mmol) and 2-cyanoacetamide (29.3 g, 349 mmol) in ethanol (600 mL) was added potassium hydroxide (23 g, 349 mmol), and the mixture was heated under reflux for 27 hr. The insoluble substance was collected by filtration to give a solid (48.7 g). 6.5 g of these was added to phenylphosphonic dichloride (65 mL), and the mixture was treated at 140° C. for 21 hr, and allowed to cool to room temperature. Ethyl acetate (450 ml) was added thereto. The resulting insoluble substance in this process was collected by filtration to give a solid (3.27 g) containing crude 2,6-dichloro-(4-piperidin-4-yl)nicotinonitrile. This solid was dissolved in dichloromethane (80 ml), TEA (4.8 mL) and di-tert-butyl dicarbonate (3.7 g) were added under ice-cooling, and the mixture was stirred at room temperature for 9 hr. Ethyl acetate was added to the reaction mixture, and the organic layer was washed with water and concentrated. The residue was purified by silica gel column chromatography to give tert-butyl 4-(2,6-dichloro-3-cyanopyridin-4-yl)piperidine-1-carboxylate (2.3 g).

$^1$H-NMR (300 MHz, CDCl$_3$) δ(ppm): 7.25 (s, 1H), 3.15-3.05 (m, 1H), 2.85 (t, 2H), 1.91-1.86 (m, 2H), 1.67-1.56 (m, 4H), 1.47 (s, 9H)

Reference Example 7

Synthesis of 2-((6-methylpyridin-3-yl)oxy)ethylamine dihydrochloride

To a solution of tert-butyl N-(2-hydroxyethyl)carbamate (49.9 g, 310 mmol) and 4-dimethylaminopyridine (42 g, 340 mmol) in dichloromethane (500 mL) was slowly added tosyl chloride (59 g, 310 mmol) under ice-cooling. The mixture was allowed to cool to room temperature, stirred for 15 hr, washed with water and saturated brine, and concentrated to give 2-((tert-butoxycarbonyl)amino)ethyl 4-methyl benzenesulfonate (98 g). 66 g (209 mmol) of these was dissolved in DMF (500 mL), 5-hydroxy-2-methylpyridine (22.8 g, 209 mmol) and cesium carbonate (102 g, 314 mmol) were added, and the mixture was stirred at 100° C. for 2 hr. The reaction mixture was allowed to cool to room temperature, poured into cool water, and extracted with ethyl acetate three times. The organic layer was washed with saturated brine, and concentrated to give crystals (35 g). The crystals were washed with tert-butyl-methyl ether to give tert-butyl (2-((6-methylpyridin-3-yl)oxy)ethyl)carbamate (24.5 g) as white crystals. The crystals were treated with 2N—HCl/Dioxane solution (140 ml) at room temperature, and the obtained insoluble substance was collected by filtration to give the object compound of 2-((6-methylpyridin-3-yl)oxy)ethylamine dihydrochloride (17.6 g).

$^1$H-NMR (300 MHz, DMSO-$d_6$) δ(ppm): 8.49 (d, 1H), 8.42 (br-s, 2H), 8.05 (dd, 1H), 7.78 (d, 1H), 4.40 (t, 2H) 3.23-3.13 (m, 2H)

Reference Example 8

Synthesis of 3-(2-aminoethoxy)benzonitrile hydrochloride

Using 2-((tert-butoxycarbonyl)amino)ethyl 4-methylbenzenesulfonate (4 g, 12.7 mmol) synthesized in Reference Example 7 and 3-cyanophenol instead of 5-hydroxy-2-methylpyridine in Reference Example 7, 3-(2-aminoethoxy)benzonitrile hydrochloride (0.75 g) was obtained.

$^1$H-NMR (300 MHz, DMSO-$d_6$) δ(ppm): 8.23 (br-s, 3H); 7.54-7.42 (m, 3H), 7.34-7.30 (m, 1H), 4.24 (t, 2H), 3.19 (t, 2H)

IR (neat): 2905, 2225, 1595 cm$^{-1}$

Starting Material Synthetic Example 1

2-chloro-6-(5-methyl-1H-pyrazol-3-ylamino)-4-methylnicotinonitrile 2,6-Dichloro-4-methylnicotinonitrile (38.2 g, 204 mmol), 3-amino-5-methylpyrazole (23.8 g, 245 mmol), potassium iodide (34 g) and TEA (34 ml) were dissolved in DMF (400 ml), and the mixture was stirred at 100° C. for 8 hr.

After stirring, the reaction mixture was added to cold water (3 L), and allowed to warm to room temperature. The insoluble substance was collected by filtration using Buechner funnel to give a solid (98 g). This solid was dissolved in DMF (500 ml), and aq. 0.5N—NaOH (1 L) was slowly added. The residue was filtered using KIRIYAMA funnel, and the filtrated product was washed with methanol (300 ml). The filtrated product was 38 g. This filtrated product was washed by suspending in a mixed solvent of ethyl acetate (400 ml)-methanol (80 ml) under heating for 3 hr, and collected by filtration to give the desired product of 2-chloro-6-(5-methyl-1H-pyrazol-3-ylamino)-4-methylnicotinonitrile (hereinafter to be referred to as compound A, 15.3 g, yield: 31%).

$^1$H-NMR (300 MHz, DMSO-$d_6$) δ(ppm): 12.08 (1H, s), 10.25 (1H, s), 7.15 (1H, br-s), 6.04 (1H, br-s), 2.40 (3H, s), 2.26 (3H, s).

m/z=248 (M+H)

Starting Material Synthetic Example 2

2-chloro-6-(5-methyl-1H-pyrazol-3-ylamino)-4-phenylnicotinonitrile

Using 2,6-dichloro-4-phenylnicotinonitrile and in the same manner as in Starting Material Synthetic Example 1, 2-chloro-6-(5-methyl-1H-pyrazol-3-ylamino)-4-phenylnicotinonitrile (hereinafter to be referred to as compound B) was obtained.

$^1$H-NMR (300 MHz, DMSO-$d_6$) δ(ppm): 12.13 (1H, s), 10.59 (1H, s), 7.70-7.40 (5H, m), 6.05 (1H, br-s), 2.20 (3H, s).

Starting Material Synthetic Example 3

2-chloro-6-(5-methyl-1H-pyrazol-3-ylamino)-4-(4-methoxyphenyl)nicotinonitrile

Using 2,6-dichloro-4-(4-methoxyphenyl)nicotinonitrile and in the same manner as in Starting Material Synthetic Example 1, 2-chloro-6-(5-methyl-1H-pyrazol-3-ylamino)-4-(4-methoxyphenyl)nicotinonitrile (hereinafter to be referred to as compound C) was obtained.

$^1$H-NMR (400 MHz, DMSO-$d_6$) δ(ppm): 12.12 (1H, s), 10.41 (1H, s), 7.55 (2H, d), 7.11 (2H, d), 6.10 (1H, br-s), 3.84 (3H, s), 2.22 (3H, s).

Starting Material Synthetic Example 4

2-chloro-6-(5-methyl-1H-pyrazol-3-ylamino)-4-(pyridin-3-yl)nicotinonitrile

Using 2,6-dichloro-4-(pyridin-3-yl)-3-nicotinonitrile and in the same manner as in Starting Material Synthetic Example 1, 2-chloro-6-(5-methyl-1H-pyrazol-3-ylamino)-4-(pyridin-3-yl)nicotinonitrile (hereinafter to be referred to as compound D) was obtained.

$^1$H-NMR (300 MHz, DMSO-$d_6$) δ(ppm): 12.12 (1H, s), 10.56 (1H, s), 8.76 (1H, d), 8.71 (1H, d), 8.10-7.90 (1H, m), 7.70-7.40 (1H, m), 6.13 (1H, br-s), 2.33 (3H, s).

Starting Material Synthetic Example 5

2-chloro-6-(5-methyl-1H-pyrazol-3-ylamino)-nicotinonitrile

Using 2,6-dichloronicotinonitrile and in the same manner as in Starting Material Synthetic Example 1,2-chloro-6-(5-methyl-1H-pyrazol-3-ylamino)-nicotinonitrile (hereinafter to be referred to as compound E) was obtained.

$^1$H-NMR (300 MHz, DMSO-$d_6$) δ(ppm): 12.12 (1H, s), 10.40 (1H, s), 7.97 (1H, d), 7.28 (1H, br-s), 6.11 (1H, br-s) 2.22 (3H, s).

Starting Material Synthetic Example 6

2-chloro-6-(5-methyl-1H-pyrazol-3-ylamino)-4-(trifluoromethyl)nicotinonitrile

Using 2,6-dichloro-4-(trifluoromethyl)nicotinonitrile and in the same manner as in Starting Material Synthetic Example 1, 2-chloro-6-(5-methyl-1H-pyrazol-3-ylamino)-4-(trifluoromethyl)nicotinonitrile (hereinafter to be referred to as compound F) was obtained.

$^1$H-NMR (300 MHz, DMSO-$d_6$) δ(ppm): 12.31 (1H, s), 11.04 (1H, s), 7.22 (1H, br-s), 6.46 (1H, br-s), 2.36 (3H, s).

Starting material synthesis compounds 1-6 are shown in the following Tables.

TABLE 1

| Starting Material Synthetic Example 1 | 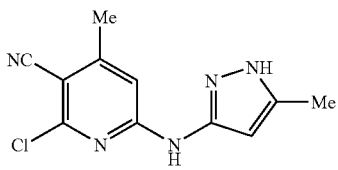 |
| --- | --- |
| Starting Material Synthetic Example 2 | 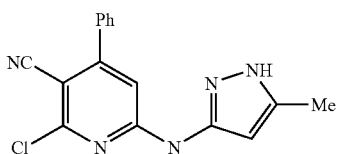 |
| Starting Material Synthetic Example 3 | 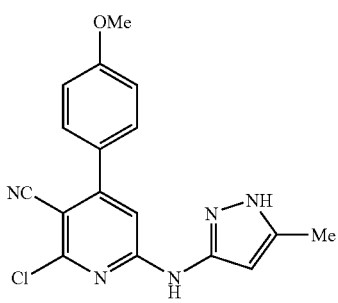 |
| Starting Material Synthetic Example 4 | 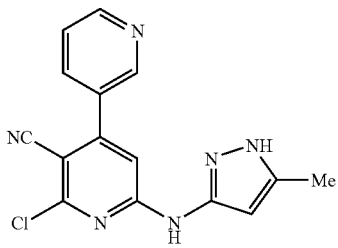 |
| Starting Material Synthetic Example 5 | 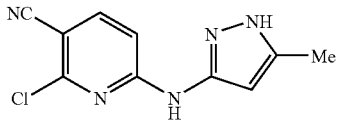 |
| Starting Material Synthetic Example 6 | 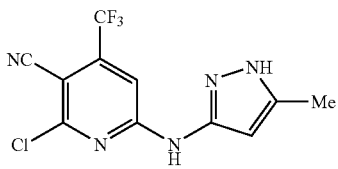 |

In addition, the following starting material compounds were synthesized in the same manner.

Starting Material Synthetic Example 7

2-chloro-6-((5-methyl-1H-pyrazol-3-yl)amino-4,4'-bipyridine-3-carbonitrile

Starting Material Synthetic Example 8

2-chloro-6-((5-methyl-1H-pyrazol-3-yl)amino)-4-(3,4,5-trimethoxyphenyl)nicotinonitrile Starting Material Synthetic Example 9

2-chloro-4-(3-methoxyphenyl)-6-(5-methyl-1H-pyrazol-3-ylamino)nicotinonitrile

Starting Material Synthetic Example 10

2-chloro-4-(2-methoxyphenyl)-6-(5-methyl-1H-pyrazol-3-ylamino)nicotinonitrile

Starting Material Synthetic Example 11

4-(1,3-benzodioxol-5-yl)-2-chloro-6-(5-methyl-1H-pyrazol-3-ylamino)nicotinonitrile Starting Material Synthetic Example 12

2-chloro-6-(5-methyl-1H-pyrazol-3-ylamino)-4-(2-thienyl)nicotinonitrile

Starting Material Synthetic Example 13

2-chloro-6-(5-methyl-1H-pyrazol-3-ylamino)-4-(3-methyl-2-thienyl)nicotinonitrile Starting Material Synthetic Example 14

2-chloro-6-(5-methyl-1H-pyrazol-3-ylamino)-4-(5-methyl-2-thienyl)nicotinonitrile Starting Material Synthetic Example 15

2-chloro-4-(4-isopropyloxyphenyl)-6-(5-methyl-1H-pyrazol-3-ylamino)nicotinonitrile Starting Material Synthetic Example 16

2-chloro-6-(5-cyclopropyl-1H-pyrazol-3-ylamino)-4-methylnicotinonitrile

Starting Material Synthetic Example 17

2-chloro-6-(5-isopropyl-1H-pyrazol-3-ylamino)-4-methylnicotinonitrile

Starting Material Synthetic Example 18

2-chloro-4-ethyl-6-(5-methyl-1H-pyrazol-3-ylamino)nicotinonitrile

Starting Material Synthetic Example 19

2-chloro-6-(5-ethyl-1H-pyrazol-3-ylamino)-4-methylnicotinonitrile

Starting Material Synthetic Example 20

2-chloro-5-methyl-6-(5-methyl-1H-pyrazol-3-ylamino)nicotinonitrile

Starting Material Synthetic Example 21

2-chloro-5-fluoro-6-(5-methyl-1H-pyrazol-3-ylamino)nicotinonitrile

Starting Material Synthetic Example 22

2-chloro-4-cyclopropyl-6-(5-methyl-1H-pyrazol-3-ylamino)nicotinonitrile

Starting Material Synthetic Example 23

2-chloro-6-(5-methyl-1H-pyrazol-3-ylamino)-4-(3-(morpholin-4-yl)propyl)nicotinonitrile Starting Material Synthetic Example 24

2-1-(5-methyl-1H-pyrazol-3-ylamino)-6,7-dihydro-5H-cyclopenta(c)pyridine-4-carbonitrile Starting Material Synthetic Example 25

2-chloro-4-methyl-6-(5-(methylthio)-1H-pyrazol-3-ylamino)nicotinonitrile

Starting Material Synthetic Example 26

2-chloro-6-(5-cyclopropyl-1H-pyrazol-3-ylamino)nicotinonitrile

Starting Material Synthetic Example 27 tert-butyl 4-(2-chloro-3-cyano-6-(5-methyl-1H-pyrazol-3-ylamino)pyridin-4-ylpiperidine-1-carboxylate Starting Material Synthetic Example 28

2-chloro-6-(5-ethoxy-1H-pyrazol-3-ylamino)-4-methylnicotinonitrile

Starting Material Synthetic Example 29

2-chloro-4-(4-isobutylphenyl-6-(5-methyl-1H-pyrazol-3-ylamino)nicotinonitrile

Starting Material Synthetic Example 30

2-chloro-4-isopropyl-6-(5-methyl-1H-pyrazol-3-ylamino)nicotinonitrile

Starting Material Synthetic Example 31

2-chloro-6-(5-methylthio-1H-pyrazol-3-ylamino)nicotinonitrile

Starting Material Synthetic Example 32

2-chloro-4-methyl-6-(1H-pyrazol-3-ylamino)nicotinonitrile

Starting Material Synthetic Example 33

4-(1-acetylpiperidin-4-yl)-2-chloro-6-(5-methyl-1H-pyrazol-3-ylamino)nicotinonitrile Starting material Synthetic Examples 7-33 are shown in the following Tables.

TABLE 2

| | Compound | NMR (ppm) |
|---|---|---|
| Starting Material Synthetic Example 7 | (structure) | 12.15 (s, 1H), 10.60 (s, 1H), 8.75 (d, 2H), 7.66 (d, 2H), 6.14 (br-s, 1H), 2.27 (s, 3H) |
| Starting Material Synthetic Example 8 | (structure) | 12.15 (s, 1H), 10.35 (s, 1H), 6.95 (br-s, 1H), 6.90 (s, 2H), 6.68 (br-s, 1H), 3.85 (s, 6H), 3.75 (s, 3H) |
| Starting Material Synthetic Example 9 | (structure) | 12.13 (s, 1H), 10.47 (s, 1H), 7.47 (t, 1H), 7.14-7.11 (m, 3H), 6.2-5.7 (m, 2H), 3.82 (s, 3H), 2.23 (s, 3H) |

TABLE 2-continued

| | Compound | NMR (ppm) |
|---|---|---|
| Starting Material Synthetic Example 10 | 2-methoxyphenyl substituted 4-aryl-3-cyano-2-chloro-6-(5-methyl-1H-pyrazol-3-ylamino)pyridine | 12.11 (s, 1H), 10.43 (s, 1H), 7.48 (dd, 1H), 7.28 (d, 1H), 7.17 (d, 1H), 7.06 (dd, 1H), 6.4-5.6 (m, 2H), 3.78 (s, 3H 2.20 (s, 3H) |
| Starting Material Synthetic Example 11 | benzo[1,3]dioxol-5-yl substituted 4-aryl-3-cyano-2-chloro-6-(5-methyl-1H-pyrazol-3-ylamino)pyridine | 12.12 (s, 1H), 10.43 (s, 1H) 7.2-7.0 (m, 2H), 6.10 (s, 2H), 1.97 (s, 3H) |

TABLE 3

| | Compound | NMR (ppm) |
|---|---|---|
| Starting Material Synthetic Example 12 | thiophen-2-yl substituted 4-aryl-3-cyano-2-chloro-6-(5-methyl-1H-pyrazol-3-ylamino)pyridine | 12.17 (s, 1H), 10.49 (s, 1H), 7.85 (d, 1H), 7.74 (d, 1H), 7.27 (dd, 1H), 6.06 (br-s, 1H) 2.20 (s, 3H) |
| Starting Material Synthetic Example 13 | 3-methylthiophen-2-yl substituted 4-aryl-3-cyano-2-chloro-6-(5-methyl-1H-pyrazol-3-ylamino)pyridine | 12.14 (s, 1H), 10.54 (s, 1H), 7.68 (d, 1H), 7.06 (d, 1H), 2.21, 2.20 (each s, each 3H) |
| Starting Material Synthetic Example 14 | 5-methylthiophen-2-yl substituted 4-aryl-3-cyano-2-chloro-6-(5-methyl-1H-pyrazol-3-ylamino)pyridine | 12.15 (s, 1H), 10.43 (s, 1H), 7.58 (d, 1H), 6.96 (d, 1H), 6.02 (br-s, 1H), 2.52, 2.20 (each s, each 3H) |

TABLE 3-continued

| | Structure | NMR |
|---|---|---|
| Starting Material Synthetic Example 15 | (structure: 2-chloro-3-cyano-4-[4-(1-methylethoxy)phenyl]-6-[(5-methyl-1H-pyrazol-3-yl)amino]pyridine) | 8.09 (s, 1H), 7.47 (d, 2H), 7.16 (s, 1H), 6.94 (d, 2H), 6.06 (s, 1H), 4.60 (dt, 1H), 2.31 (s, 3H), 1.37, 1.35 (each s, each 3H) |
| Starting Material Synthetic Example 16 | (structure: 2-chloro-3-cyano-4-methyl-6-[(5-cyclopropyl-1H-pyrazol-3-yl)amino]pyridine) | 12.14 (s, 1H), 10.24 (s, 1H), 7.21 (br-s, 1H), 5.96 (br-s, 1H), 2.37 (s, 3H), 1.89 (m, 1H) 0.93 (m, 2H), 0.68 (m, 2H) |
| Starting Material Synthetic Example 17 | (structure: 2-chloro-3-cyano-4-methyl-6-[(5-isopropyl-1H-pyrazol-3-yl)amino]pyridine) | 12.14 (s, 1H), 10.27 (s, 1H), 7.24 (br-s, 1H), 6.05 (br-s, 1H), 2.93 (m, 1H), 2.37 (s, 3H) 1.22 (d, 6H) |

TABLE 4

| | Structure | NMR |
|---|---|---|
| Starting Material Synthetic Example 18 | (structure: 2-chloro-3-cyano-4-ethyl-6-[(5-methyl-1H-pyrazol-3-yl)amino]pyridine) | 12.10 (s, 1H), 10.28 (s, 1H), 7.21 (br-s, 1H), 6.06 (br-s, 1H), 2.67 (q, 2H), 2.19 (s, 1H) 1.71 (t, 3H) |
| Starting Material Synthetic Example 19 | (structure: 2-chloro-3-cyano-4-methyl-6-[(5-ethyl-1H-pyrazol-3-yl)amino]pyridine) | 12.13 (s, 1H), 10.27 (s, 1H), 7.20 (br-s, 1H), 6.08 (br-s, 1H), 2.59 (q, 2H), 2.37 (s, 3H) 1.19 (t, 3H) |
| Starting Material Synthetic Example 20 | (structure: 2-chloro-3-cyano-5-methyl-6-[(5-methyl-1H-pyrazol-3-yl)amino]pyridine) | 12.86 (s, 1H), 9.26 (s, 1H), 7.81 (s, 1H), 6.35 (s, 1H), 2.25 (s, 3H), 2.21 (s, 3H), |
| Starting Material Synthetic Example 21 | (structure: 2-chloro-3-cyano-5-fluoro-6-[(5-methyl-1H-pyrazol-3-yl)amino]pyridine) | 12.02 (s, 1H), 10.32 (s, 1H), 8.07 (d, 1H), 6.32 (s, 1H), 2.22 (s, 3H) |
| Starting Material Synthetic Example 22 | (structure: 2-chloro-3-cyano-4-cyclopropyl-6-[(5-methyl-1H-pyrazol-3-yl)amino]pyridine) | 12.07 (s, 1H), 10.14 (s, 1H), 6.90 (br-s, 1H), 6.01 (br-s, 1H), 2.18 (s, 3H), 2.03 (m, 1H), 1.3-1.1 (m, 2H) 0.8-0.6 (m, 2H) |

TABLE 4-continued

| | | |
|---|---|---|
| Starting Material Synthetic Example 23 | 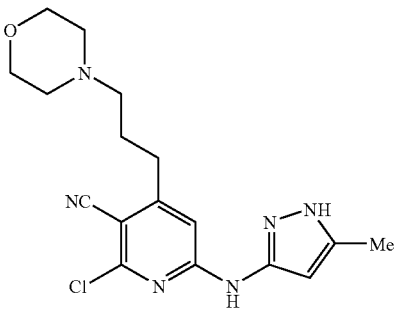 | 11.06 (s, 1H), 6.80 (s, 1H), 5.17 (s, 1H), 4.93 (br-s, 1H), 3.7-3.4 (m, 8H), 2.97 (q, 2H), 2.68 (t, 1H), 2.05 (s, 3H), 1.80 (t, 2H) |

TABLE 5

| | | |
|---|---|---|
| Starting Material Synthetic Example 24 | 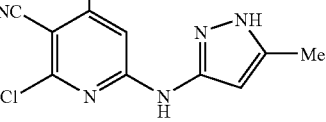 | 12.12 (s, 1H), 9.59 (s, 1H), 6.36 (s, 1H), 2.94 (t, 2H), 2.81 (t, 2H), 2.23 (s, 3H), 2.14-2.06 (m, 2H) |
| Starting Material Synthetic Example 25 | 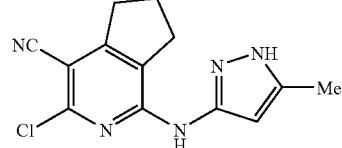 | 12.66 (s, 1H), 10.39 (s, 1H), 7.10 (br-s, 1H), 6.34 (s, 1H), 2.47, 2.36 (each s, each 3H) |
| Starting Material Synthetic Example 26 | 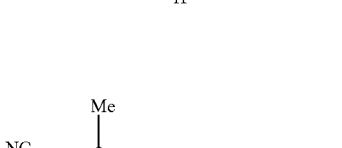 | 12.17 (s, 1H), 10.38 (s, 1H), 7.97 (d, 1H), 7.28 (br-s, 1H), 6.00 (br-s, 1H), 1.89 (m, 1H) 0.93 (m, 2H), 0.68 (m, 2H) |
| Starting Material Synthetic Example 27 | 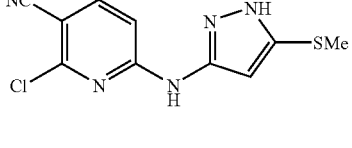 | 12.10 (s, 1H), 10.30 (s, 1H), 6.05 (br-s, 1H), 4.06 (d, 2H), 3.6-2.8 (m, 5H), 2.18 (s, 3H), 1.84-1.79 (m, 2H), 1.40 (s, 9H) |
| Starting Material Synthetic Example 28 | 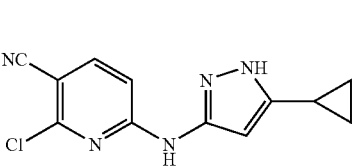 | 12.00 (s.0.67H), 11.56 (s, 0.33H), 10.24 (s, 1H), 7.27 (br-s, 0.67H), 6.68 (br-s, 0.33H) 5.62 (br-s, 1H), 4.15-4.00 (m, 2H), 2.38 (s, 3H), 1.40-1.10 (m, 3H) |

TABLE 6

| | | |
|---|---|---|
| Starting Material Synthetic Example 29 | *(structure: 4-(4-isobutylphenyl)-substituted pyridine with Cl, CN, and 5-methyl-1H-pyrazol-3-ylamino)* | 12.11 (s, 1H), 10.45 (s, 1H), 7.48 (d, 2H), 7.32 (d, 2H), 6.6-5.8 (m, 1H), 2.6-2.4 (m, 2H), 2.20 (s, 3H), 1.88 (m, 1H), 0.88, 0.86 (each s, each 3H) |
| Starting Material Synthetic Example 30 | *(structure: 4-isopropyl-substituted pyridine with Cl, CN, and 5-methyl-1H-pyrazol-3-ylamino)* | 12.10 (s, 1H), 10.27 (s, 1H), 7.30 (br-s, 1H), 6.06 (s, 1H), 3.03 (m, 1H), 2.19 (s, 3H), 1.22, 1.20 (each s, each 3H) |
| Starting Material Synthetic Example 31 | *(structure: pyridine with Cl, CN, and 5-SMe-1H-pyrazol-3-ylamino)* | 12.70 (s, 1H), 10.53 (s, 1H), 8.00 (d, 1H), 7.30-7.10 (br-s, 1H), 6.39 (brs, 1H), 2.47 (s, 3H) |
| Starting Material Synthetic Example 32 | *(structure: 4-methyl pyridine with Cl, CN, and 1H-pyrazol-3-ylamino)* | 12.42 (s, 1H), 10.36 (s, 1H), 7.67 (s, 1H), 7.18 (br-s, 1H) 6.32 (br-s, 1H), 2.38 (s, 3H) |
| Starting Material Synthetic Example 33 | *(structure: 4-(1-acetylpiperidin-4-yl)-substituted pyridine with Cl, CN, and 5-methyl-1H-pyrazol-3-ylamino)* | 12.13 (s, 1H), 10.33 (s, 1H), 7.34 (br-s, 1H), 6.04 (br-s, 1H), 4.52 (d, 1H), 3.93 (d, 1H), 3.18 (t, 1H), 2.92 (t, 1H), 2.60 (t, 1H), 2.19 (s, 3H), 2.01 (s, 3H), 2.0-1.7 (m, 2H), 1.6-1.3 (m, 2H) |

Example 1

Compound B (300 mg, 972 μmol), 2-phenoxyethylamine (254 μl) and sodium hydrogencarbonate (817 mg) were added to DMSO (10 ml), and the mixture was stirred at 100° C. for 27 hr. After stirring, the reaction mixture was added to cold water, and the mixture was extracted with ethyl acetate. The organic layer was washed with saturated brine, and concentrated, and the residue was washed by suspending in ethyl acetate to give the object compound of 2-(2-phenoxyethylamino)-6-(5-methyl-1H-pyrazol-3-ylamino)-4-phenylnicotinonitrile (130 mg).

$^1$H-NMR (400 MHz, DMSO-$d_6$) δ(ppm): 11.87 (1H, br-s), 9.69 (1H, br-s), 7.50 (5H, m), 7.28 (2H, t), 6.97-6.93 (4H. m), 6.38 (1H, br-s), 6.25 (1H, br-s), 4.18 (2H, t), 3.82 (2H, q), 2.06 (3H, s).

Example 2

Compound A (400 mg, 1.63 mmol), 2-phenoxyethylamine (638 μl) and sodium hydrogencarbonate (1.37 g) were added to DMSO (12 ml), and the mixture was stirred at 100° C. for 27 hr. After stirring, the reaction mixture was added to cold water, and the mixture was extracted with ethyl acetate. The organic layer was washed with saturated brine, and concentrated, and the residue was washed by suspending in ethyl acetate to give the object compound of 2-(2-phenoxyethylamino)-6-(5-methyl-1H-pyrazol-3-ylamino)-4-methylnicotinonitrile (66 mg).

$^1$H-NMR (400 MHz, DMSO-$d_6$) δ(ppm): 11.84 (1H, br-s), 9.48 (1H, br-s), 7.27 (2H, t), 6.95-6.90 (3H, m), 6.79 (1H, br-s), 6.31-6.15 (2H, m), 4.12 (2H, t), 3.75 (2H, q), 2.19 (3H, s), 2.04 (3H, s).

m/z=349 (M+H)

Example 3

Compound F (300 mg, 1.00 mmol), 2-phenoxyethylamine (261 μl) and sodium hydrogencarbonate (837 mg) were added to DMSO (10 ml), and the mixture was stirred at 100° C. for 27 hr. After stirring, the reaction system was added to cold water, and the mixture was extracted with ethyl acetate. The organic layer was washed with saturated brine, and concentrated, and the residue was washed by suspending in ethyl acetate to give the object compound of 2-(2-phenoxyethylamino)-6-(5-methyl-1H-pyrazol-3-ylamino)-4-trifluoromethylnicotinonitrile (80 mg).

$^1$H-NMR (400 MHz, DMSO-$d_6$) δ(ppm): 12.04 (1H, br-s), 10.23 (1H, br-s), 7.38 (1H, br-s), 7.27 (2H, t), 6.98-6.91 (3H, m), 6.52-6.35 (2H, m), 4.15 (2H, t), 3.80 (2H, q), 2.06 (3H, s).

Example 4

Compound C (300 mg, 885 μmol), 2-phenoxyethylamine (290 μl) and sodium hydrogencarbonate (743 mg) were added to DMSO (10 ml), and the mixture was stirred at 100° C. for 27 hr.

After stirring, the reaction mixture was added to cold water, and the mixture was extracted with ethyl acetate. The organic layer was washed with saturated brine, and concentrated, and the residue was washed by suspending in ethyl acetate to give the object compound of 2-(2-phenoxyethylamino)-6-(5-methyl-1H-pyrazol-3-ylamino)-4-(4-methoxyphenyl)nicotinonitrile (87 mg).

$^1$H-NMR (400 MHz, DMSO-$d_6$) δ(ppm): 11.87 (1H, br-s), 9.63 (1H, br-s), 7.45 (2H, d), 7.26 (2H, t), 7.06 (2H, d), 6.98-6.91 (3H, m), 6.88 (1H, br-s), 6.41 (1H, br-s), 6.25 (1H, br-s), 4.17 (2H, t), 3.82 (5H, m), 2.05 (3H, s).

Example 5

Compound A (300 mg, 1.22 mmol), 2-(4-methoxyphenoxy)ethylamine hydrochloride (489 mg) and sodium hydrogencarbonate (1.37 g) were added to DMSO (10 ml), and the mixture was stirred at 100° C. for 27 hr. After stirring, the reaction mixture was added dropwise to cold water, and the mixture was extracted with ethyl acetate. The organic layer was washed with saturated brine, and concentrated, and the residue was washed by suspending in ethyl acetate. This was converted to hydrochloride to give the object compound of 2-(2-(4-methoxyphenoxy)ethylamino)-6-(5-methyl-1H-pyrazol-3-ylamino)-4-methylnicotinonitrile hydrochloride (98 mg).

$^1$H-NMR (400 MHz, DMSO-$d_6$) δ(ppm): 10.06 (1H, br-s), 7.03 (1H, br-s), 6.88-6.81 (4H, m), 6.28 (1H, s), 6.23 (1H, s), 4.07 (2H, t), 3.75 (2H, q), 3.68 (3H, s), 2.23 (3H, s), 2.13 (3H, s).

Example 6

Compound D (150 mg, 483 μmol), 2-phenoxyethylamine (127 μl) and sodium hydrogencarbonate (400 mg) were added to DMSO (3 ml), and the mixture was stirred at 100° C. for 27 hr. After stirring, the reaction mixture was added dropwise to cold water, and the mixture was extracted with ethyl acetate. The organic layer was washed with saturated brine, and concentrated, and the residue was washed by suspending in ethyl acetate to give the object compound of 2-(2-phenoxyethylamino)-6-(5-methyl-1H-pyrazol-3-ylamino)-4-(pyridin-3-yl)nicotinonitrile (82 mg).

$^1$H-NMR (400 MHz, DMSO-$d_6$) δ(ppm): 12.06 (1H, br-s), 10.22 (1H, br-s), 8.72-8.69 (2H, m), 7.98 (1H, dd), 7.65 (1H, dd), 7.29-7.23 (2H, m), 6.96-6.90 (3H, m), 6.16 (1H, br-s), 4.23 (2H, t), 3.67 (2H, t), 2.22 (3H, s).

m/z=412 (M+H)

Example 7

Compound A (400 mg, 1.63 mmol), 2-(pyridin-2-yloxy)ethylamine (674 μl) and sodium hydrogencarbonate (1.37 g) were added to DMSO (12 ml), and the mixture was stirred at 100° C. for 27 hr. After stirring, the reaction mixture was added to cold water, and the mixture was extracted with ethyl acetate. The organic layer was washed with saturated brine, and concentrated, and the residue was washed by suspending in ethyl acetate. This was converted to hydrochloride to give the object compound of 2-(2-(pyridin-2-yloxy)ethylamino)-6-(5-methyl-1H-pyrazol-3-ylamino)-4-methylnicotinonitrile dihydrochloride (68 mg).

$^1$H-NMR (400 MHz, DMSO-$d_6$) δ(ppm): 10.33 (1H, br-s), 8.15 (1H, d), 7.72 (1H, dd), 7.21 (1H, br-s), 6.98 (1H, dd), 6.83 (1H, d), 6.31 (1H, s), 6.23 (1H, s), 4.45 (2H, t), 3.78 (2H, t), 2.24 (3H, s), 2.18 (3H, s).

Example 8

Compound A (400 mg, 1.63 mmol), 2-(2-methoxyphenoxy)ethylamine hydrochloride (1.10 g) and sodium hydrogencarbonate (1.37 g) were added to DMSO (12 ml), and the mixture was stirred at 100° C. for 27 hr. After stirring, the reaction mixture was added to cold water, and the mixture was extracted with ethyl acetate. The organic layer was washed with saturated brine, and concentrated, and the residue was washed by suspending in ethyl acetate to give the object compound of 2-(2-(2-methoxyphenoxy)ethylamino)-6-(5-methyl-1H-pyrazol-3-ylamino)-4-methylnicotinonitrile (89 mg).

$^1$H-NMR (400 MHz, DMSO-$d_6$) δ(ppm): 11.83 (1H, br-s), 10.06 (1H, br-s), 6.98-6.82 (4H, m), 6.72 (1H, br-s), 6.25 (1H, br-s), 6.19 (1H, br-s), 4.11 (2H, t), 3.76 (5H, m), 2.19 (3H, s), 2.05 (3H, s). m/z=379 (M+H)

Example 9

Compound A (1.53 g, 6.25 mmol), 2-(3-fluorophenoxy)ethylamine hydrochloride (1.79 g) and sodium hydrogencarbonate (5.25 g) were added to DMSO (30 ml), and the mixture was stirred at 100° C. for 27 hr. After stirring, the reaction mixture was added dropwise to cold water, and the mixture was extracted with ethyl acetate. The organic layer was washed with saturated brine, and concentrated, and the residue was purified by silica gel chromatography. This was converted to hydrochloride to give the object compound of 2-(2-(3-fluorophenoxy)ethylamino)-6-(5-methyl-1H-pyrazol-3-ylamino)-4-methylnicotinonitrile hydrochloride (308 mg).

$^1$H-NMR (400 MHz, DMSO-$d_6$) δ(ppm): 9.90 (1H, s), 7.28 (1H, dd), 6.98 (1H, br-s), 6.83-6.72 (3H, m), 6.25 (1H, s), 6.24 (1H, s), 4.15 (2H, t), 3.76 (2H, t), 2.22 (3H, s), 2.11 (3H, s). m/z=367 (M+H)

Example 10

Compound A (200 mg, 813 mmol), 2-(4-fluorophenoxy) ethylamine hydrochloride (466 mg) and sodium hydrogencarbonate (683 mg) were added to DMSO (6 ml), and the mixture was stirred at 100° C. for 27 hr. After stirring, the reaction mixture was added to cold water, and the mixture was extracted with ethyl acetate. The organic layer was washed with saturated brine, and concentrated, and the residue was washed by suspending in ethyl acetate to give the object compound of 2-(2-(4-fluorophenoxy)ethylamino)-6-(5-methyl-1H-pyrazol-3-ylamino)-4-methylnicotinonitrile (38 mg).

$^1$H-NMR (400 MHz, DMSO-$d_6$) δ(ppm): 11.84 (1H, s), 9.47 (1H, s), 7.09 (1H, t), 6.98-6.94 (2H, m), 6.78 (1H, br-s), 6.32-6.10 (2H, m), 4.10 (2H, t), 3.74 (2H, q), 2.19 (3H, s), 2.06 (3H, s).

Example 11

Compound A (400 mg, 1.63 mmol), 2-(pyridin-4-yloxy) ethylamine (540 μl) and sodium hydrogencarbonate (1.32 g) were added to DMSO (12 ml), and the mixture was stirred at 100° C. for 27 hr. After stirring, the reaction mixture was added to cold water, and the mixture was extracted with ethyl acetate. The organic layer was washed with saturated brine, and concentrated, and the residue was washed by suspending in ethyl acetate to give the object compound of 2-(2-(pyridin-4-yloxy)ethylamino)-6-(5-methyl-1H-pyrazol-3-ylamino)-4-methylnicotinonitrile (23 mg).

$^1$H-NMR (400 MHz, DMSO-$d_6$) δ(ppm): 11.85 (1H, br-s), 9.48 (1H, br-s), 8.36 (2H, d), 6.97 (2H, d), 6.84 (1H, br-s), 6.26-6.45 (2H, m), 4.22 (2H, t), 3.76 (2H, q), 2.19 (3H, s), 2.05 (3H, s).

Example 12

Compound A (13 g, 53 mmol), 2-(pyridin-3-yloxy)ethylamine (11 g, 80 mmol) and sodium hydrogencarbonate (45 g) were added to DMSO (130 ml), and the mixture was stirred at 130° C. for 20 hr. After stirring, the reaction mixture was added to cold water, and insoluble substance was filtrated (20 g). This was converted to hydrochloride to give the object compound of 2-(2-(pyridin-3-yloxy)ethylamino)-6-(5-methyl-1H-pyrazol-3-ylamino)-4-methylnicotinonitrile dihydrochloride (15.5 g).

$^1$H-NMR (400 MHz, DMSO-$d_6$) δ(ppm): 9.94 (1H, br-s), 8.66 (1H, d), 8.47 (1H, d), 8.11 (1H, dd), 7.88 (1H, dd), 7.02 (1H, br-s), 6.26 (1H, s), 6.21 (1H, s), 4.40 (2H, t), 3.82 (2H, br-s), 2.22 (3H, s), 2.15 (3H, s).
m/z=350 (M+H)

Example 13

Compound A (300 mg, 1.22 mmol), 2-(2-fluorophenoxy) ethylamine hydrochloride (700 mg) and sodium hydrogencarbonate (1.02 g) were added to DMSO (10 ml), and the mixture was stirred at 100° C. for 27 hr. After stirring, the reaction mixture was added to cold water, and the mixture was extracted with ethyl acetate. The organic layer was washed with saturated brine, and concentrated, and the residue was washed by suspending in ethyl acetate. This was converted to hydrochloride to give the object compound of 2-(2-(2-fluorophenoxy)ethylamino)-6-(5-methyl-1H-pyrazol-3-ylamino)-4-methylnicotinonitrile hydrochloride (126 mg).

$^1$H-NMR (400 MHz, DMSO-$d_6$) δ(ppm): 10.10 (1H, br-s), 7.22-7.10 (2H, m), 7.08 (1H, t), 7.06 (1H, br-s), 6.92 (1H, dd), 6.27 (1H, s), 6.24 (1H, s), 4.21 (2H, t), 3.80 (2H, t), 2.23 (3H, s), 2.13 (3H, s).

Example 14

Compound E (400 mg, 1.72 mmol), 2-phenoxyethylamine (674 μl) and sodium hydrogencarbonate (1.44 g) were added to DMSO (12 ml), and the mixture was stirred at 100° C. for 27 hr. After stirring, the reaction mixture was added to cold water, and the mixture was extracted with ethyl acetate. The organic layer was washed with saturated brine, and concentrated, and the residue was washed by suspending in ethyl acetate to give the object compound of 2-(2-phenoxyethylamino)-6-(5-methyl-1H-pyrazol-3-ylamino)nicotinonitrile (85 mg).

$^1$H-NMR (400 MHz, DMSO-$d_6$) δ(ppm): 11.86 (1H, s), 9.59 (1H, br-s), 7.50 (1H, d), 7.27 (2H, t), 6.96-6.90 (3H, m), 6.90 (1H, br-s), 6.31 (1H, br-s), 6.24 (1H, br-s), 4.13 (2H, t), 3.76 (2H, q), 2.04 (3H, s).

Example 15

Compound E (400 mg, 1.72 mmol), 2-(3-fluorophenoxy) ethylamine hydrochloride (984 mg) and sodium hydrogencarbonate (1.44 g) were added to DMSO (12 ml), and the mixture was stirred at 100° C. for 27 hr. After stirring, the reaction mixture was added dropwise to cold water, and the mixture was extracted with ethyl acetate. The organic layer was washed with saturated brine, and concentrated, and the residue was washed by suspending in ethyl acetate to give the object compound of 2-(2-(3-fluorophenoxy)ethylamino)-6-(5-methyl-1H-pyrazol-3-ylamino)nicotinonitrile (123 mg).

$^1$H-NMR (400 MHz, DMSO-$d_6$) δ(ppm): 11.87 (1H, s), 9.59 (1H, s), 7.50 (1H, d), 7.27 (1H, dd), 6.91 (1H, br-s), 6.86-6.72 (3H, m), 6.32 (1H, br-s), 6.22 (1H, br-s), 4.16 (2H, t), 3.75 (2H, q), 2.06 (3H, s).

Example 16

Compound A (300 mg, 1.22 mmol), 2-(3-chloro-4-fluorophenoxy)ethylamine hydrochloride (824 mg) and sodium hydrogencarbonate (1.02 g) were added to DMSO (10 ml), and the mixture was stirred at 100° C. for 27 hr. After stirring, the reaction mixture was added to cold water, and the mixture was extracted with ethyl acetate. The organic layer was washed with saturated brine, and concentrated, and the residue was washed by suspending in ethyl acetate to give the object compound of 2-(2-(3-chloro-4-fluorophenoxy)ethylamino)-6-(5-methyl-1H-pyrazol-3-ylamino)-4-methylnicotinonitrile (26 mg).

$^1$H-NMR (400 MHz, DMSO-$d_6$) δ(ppm): 11.80 (1H, br-s), 9.47 (1H, br-s), 7.18 (1H, dd), 7.30 (1H, t), 6.96 (1H, dd), 6.94 (1H, br-s), 6.25 (1H, br-s), 6.19 (1H, br-s), 4.14 (2H, t), 3.73 (2H, q), 2.19 (3H, s), 2.07 (3H, s).
m/z=401 (M+H)

Example 17

Compound E (400 mg, 1.72 mmol), 2-(pyridin-3-yloxy) ethylamine (711 µl) and sodium hydrogencarbonate (1.44 g) were added to DMSO (12 ml), and the mixture was stirred at 100° C. for 27 hr. After stirring, the reaction mixture was added to cold water, and the mixture was extracted with ethyl acetate. The organic layer was washed with saturated brine, and concentrated, and the residue was washed by suspending in ethyl acetate to give the object compound of 2-(2-(pyridin-3-yloxy)ethylamino)-6-(5-methyl-1H-pyrazol-3-ylamino) nicotinonitrile (52 mg).

$^1$H-NMR (400 MHz, DMSO-d$_6$) δ(ppm): 11.87 (1H, s), 9.59 (1H, s), 8.30 (1H, d), 8.16 (1H, d), 7.50 (1H, d), 7.40 (1H, dd), 7.30 (1H, dd), 6.93 (1H, br-s), 6.32 (1H, br-s), 6.22 (1H, br-s), 4.22 (2H, t) 3.77 (2H, q) 2.04 (3H, s).

Example 18

Compound D (202 mg, 650 µmol), 2-(3-fluorophenoxy) ethylamine hydrochloride (357 mg) and sodium hydrogencarbonate (540 mg) were added to DMSO (3 ml), and the mixture was stirred at 130° C. for 24 hr. After stirring, the reaction mixture was added to cold water, and the mixture was extracted with ethyl acetate. The organic layer was washed with saturated brine, and concentrated, and the residue was purified by silica gel chromatography (90 mg). This was converted to hydrochloride to give the object compound of 2-(2-(3-fluorophenoxy)ethylamino)-6-(5-methyl-1H-pyrazol-3-ylamino)-4-(pyridin-3-yl)nicotinonitrile dihydrochloride (22 mg).

$^1$H-NMR (400 MHz, DMSO-d$_6$) δ(ppm): 10.49 (1H, br-s), 9.03 (1H, s), 8.93 (1H, d), 8.52 (1H, d), 8.03 (1H, dd), 7.50-7.20 (3H, m), 6.90-6.60 (3H, m), 6.45 (1H, s), 6.34 (1H, s), 4.18 (2H, t), 3.81 (2H, t-like), 2.11 (3H, s).

Example 19

Compound E (400 mg, 1.72 mmol), 2-(2-fluorophenoxy) ethylamine hydrochloride (787 mg) and sodium hydrogencarbonate (1.49 g) were added to DMSO (12 ml), and the mixture was stirred at 100° C. for 27 hr. After stirring, the reaction mixture was added to cold water, and the mixture was extracted with ethyl acetate. The organic layer was washed with saturated brine, and concentrated, and the residue was washed by suspending in ethyl acetate. This was converted to hydrochloride to give the object compound of 2-(2-(2-fluorophenoxy)ethylamino)-6-(5-methyl-1H-pyrazol-3-ylamino)nicotinonitrile hydrochloride (51 mg).

$^1$H-NMR (400 MHz, DMSO-d$_6$) δ(ppm): 9.96 (1H, br-s), 7.57 (1H, d), 7.22-7.14 (2H, m), 7.12-7.00 (2H, m), 6.96-6.90 (1H, m), 6.30 (1H, d), 6.27 (1H, s), 4.21 (2H, t), 3.79 (2H, t), 2.10 (3H, s).

Example 20

Compound A (300 mg, 1.22 mmol), 2-(3,5-difluorophenoxy)ethylamine hydrochloride (767 mg) and sodium hydrogencarbonate (1.02 g) were added to DMSO (10 ml), and the mixture was stirred at 100° C. for 27 hr. After stirring, the reaction mixture was added to cold water, and the mixture was extracted with ethyl acetate. The organic layer was washed with saturated brine, and concentrated, and the residue was washed by suspending in ethyl acetate. This was converted to hydrochloride to give the object compound of 2-(2-(3,5-difluorophenoxy)ethylamino)-6-(5-methyl-1H-pyrazol-3-ylamino)-4-methylnicotinonitrile hydrochloride (56 mg).

$^1$H-NMR (400 MHz, DMSO-d$_6$) δ(ppm): 9.94 (1H, br-s), 6.98 (1H, br-s), 6.79-6.70 (3H, m), 6.24 (2H, s), 4.18 (2H, t) 3.76 (2H, t), 2.22 (3H, s), 2.13 (3H, s).

Example 21

Compound A (300 mg, 1.22 mmol), 2-(6-methylpyridin-3-yloxy)ethylamine hydrochloride (549 mg) and sodium hydrogencarbonate (1.02 g) were added to DMSO (10 ml), and the mixture was stirred at 100° C. for 27 hr. After stirring, the reaction mixture was added to cold water, and the mixture was extracted with ethyl acetate. The organic layer was washed with saturated brine, and concentrated, and the residue was washed by suspending in ethyl acetate to give the object compound of 2-(2-(6-methylpyridin-3-yloxy)ethylamino)-6-(5-methyl-1H-pyrazol-3-ylamino)-4-methylnicotinonitrile (88 mg).

$^1$H-NMR (400 MHz, DMSO-d$_6$) δ(ppm): 11.85 (1H, s), 9.47 (1H, s), 8.15 (1H, d), 7.29 (1H, dd), 7.13 (1H, d), 6.80 (1H, br-s), 6.25 (1H, br-s), 6.19 (1H, br-s), 4.16 (2H, t), 3.74 (2H, q), 2.38 (3H, s), 2.19 (3H, s), 2.05 (3H, s). m/z=364 (M+H)

Example 22

Compound A (300 mg, 1.22 mmol), 2-(2-methylpyridin-3-yloxy)ethylamine hydrochloride (547 mg) and sodium hydrogencarbonate (1.02 g) were added to DMSO (10 ml), and the mixture was stirred at 100° C. for 27 hr. After stirring, the reaction mixture was added to cold water, and the mixture was extracted with ethyl acetate. The organic layer was washed with saturated brine, and concentrated, and the residue was washed by suspending in ethyl acetate. This was converted to hydrochloride to give the object compound of 2-(2-(2-methylpyridin-3-yloxy)ethylamino)-6-(5-methyl-1H-pyrazol-3-ylamino)-4-methylnicotinonitrile dihydrochloride (87 mg).

$^1$H-NMR (400 MHz, DMSO-d$_6$) δ(ppm): 10.01 (1H, br-s), 8.30 (1H, d), 8.15 (1H, d), 7.79 (1H, dd), 7.10 (1H, br-s), 6.24 (1H, s), 6.21 (1H, s), 4.41 (2H, t), 3.83 (2H, br-s), 2.53 (3H, s), 2.22 (3H, s), 2.17 (3H, s).
m/z=364 (M+H)

Example 23

Compound A (300 mg, 1.22 mmol), 2-(2,6-dimethylpyridin-3-yloxy)ethylamine hydrochloride (584 mg) and sodium hydrogencarbonate (1.02 g) were added to DMSO (10 ml), and the mixture was stirred at 100° C. for 27 hr. After stirring, the reaction mixture was added dropwise to cold water, and the mixture was extracted with ethyl acetate. The organic layer was washed with saturated brine, and concentrated, and the residue was washed by suspending in ethyl acetate. This was converted to hydrochloride to give the object compound of 2-(2-(2,6-dimethylpyridin-3-yloxy)ethylamino)-6-(5-methyl-1H-pyrazol-3-ylamino)-4-methylnicotinonitrile dihydrochloride (30 mg).

$^1$H-NMR (400 MHz, DMSO-d$_6$) δ(ppm): 9.78 (1H, br-s), 8.01 (1H, d), 7.61 (1H, d), 6.99 (1H, br-s), 6.23 (1H, br-s), 6.15 (1H, s), 4.37 (2H, t), 3.79 (2H, br-s), 2.59 (3H, s), 2.50 (3H, s), 2.20 (3H, s), 2.15 (3H, s).

Example 24

Compound A (200 mg, 813 µmol), 2-(2-chlorophenoxy) ethylamine (280 µl) and sodium hydrogencarbonate (683 mg)

were added to DMSO (6 ml), and the mixture was stirred at 100° C. for 27 hr. After stirring, the reaction mixture was added to cold water, and the mixture was extracted with ethyl acetate. The organic layer was washed with saturated brine, and concentrated, and the residue was washed by suspending in ethyl acetate. This was converted to hydrochloride to give the object compound of 2-(2-(2-chlorophenoxy)ethylamino)-6-(5-methyl-1H-pyrazol-3-ylamino)-4-methylnicotinonitrile hydrochloride (18 mg).

$^1$H-NMR (400 MHz, DMSO-$d_6$) δ(ppm): 9.97 (1H, br-s), 7.41 (1H, d), 7.25 (1H, t), 7.16 (1H, d), 7.00 (1H, br-s), 6.94 (1H, t), 6.24 (2H, br-s), 4.21 (2H, t), 3.80 (2H, br-s), 2.22 (3H, s), 2.09 (3H, s).

Example 25

Compound E (200 mg, 858 μmol), 2-(2-chlorophenoxy)ethylamine (295 μl) and sodium hydrogencarbonate (721 mg) were added to DMSO (6 ml), and the mixture was stirred at 100° C. for 27 hr. After stirring, the reaction mixture was added to cold water, and the mixture was extracted with ethyl acetate. The organic layer was washed with saturated brine, and concentrated, and the residue was washed by suspending in ethyl acetate. This was converted to hydrochloride to give the object compound of 2-(2-(2-chlorophenoxy)ethylamino)-6-(5-methyl-1H-pyrazol-3-ylamino)nicotinonitrile hydrochloride (50 mg).

$^1$H-NMR (400 MHz, DMSO-$d_6$) δ(ppm): 10.04 (1H, br-s), 7.58 (1H, d), 7.41 (1H, d), 7.26 (1H, t), 7.17 (1H, d), 7.08 (1H, br-s), 6.95 (1H, t), 6.30 (1H, d), 6.27 (1H, br-s), 4.22 (2H, t), 3.81 (2H, br-s), 2.08 (3H, s).

Example 26

Compound C (200 mg, 589 mmol), 2-(2-chlorophenoxy)ethylamine (202 μl) and sodium hydrogencarbonate (495 mg) were added to DMSO (6 ml), and the mixture was stirred at 100° C. for 27 hr. After stirring, the reaction mixture was added to cold water, and the mixture was extracted with ethyl acetate. The organic layer was washed with saturated brine, and concentrated, and the residue was washed by suspending in ethyl acetate. This was converted to hydrochloride to give the object compound of 2-(2-(2-chlorophenoxy)ethylamino)-6-(5-methyl-1H-pyrazol-3-ylamino)-4-(4-methoxyphenyl)nicotinonitrile hydrochloride (12 mg).

$^1$H-NMR (400 MHz, DMSO-$d_6$) δ(ppm): 9.74 (1H, br-s), 7.44 (2H, d), 7.43 (1H, d), 7.27 (1H, t), 7.19 (1H, d), 7.07 (2H, d), 6.95 (1H, t), 6.90 (1H, br-s), 6.41 (1H, br-s), 6.24 (1H, br-s), 4.25 (2H, t), 3.85 (3H, s), 3.84 (2H, br-s), 2.07 (3H, s).

Example 27

Compound E (300 mg, 1.29 mmol), 2-(6-methylpyridin-3-yloxy)ethylamine hydrochloride (577 mg) and sodium hydrogencarbonate (1.08 g) were added to DMSO (10 ml), and the mixture was stirred at 100° C. for 27 hr. After stirring, the reaction mixture was added to cold water, and the mixture was extracted with ethyl acetate. The organic layer was washed with saturated brine, and concentrated, and the residue was washed by suspending in ethyl acetate. This was converted to hydrochloride to give the object compound of 2-(2-(6-methylpyridin-3-yloxy)ethylamino)-6-(5-methyl-1H-pyrazol-3-ylamino)nicotinonitrile dihydrochloride (79 mg).

$^1$H-NMR (400 MHz, DMSO-$d_6$) δ(ppm): 9.92 (1H, s), 8.52 (1H, d), 8.11 (1H, dd), 7.78 (1H, d), 7.56 (1H, d), 7.06 (1H, br-s), 6.34 (1H, d), 6.21 (1H, s), 4.38 (2H, t), 3.81 (2H, br-s), 2.64 (3H, s), 2.14 (3H, s).

Example 28

Compound E (300 mg, 1.29 mmol), 2-(2-methylpyridin-3-yloxy)ethylamine hydrochloride (577 mg) and sodium hydrogencarbonate (1.08 g) were added to DMSO (10 ml), and the mixture was stirred at 100° C. for 27 hr. After stirring, the reaction mixture was added to cold water, and the mixture was extracted with ethyl acetate. The organic layer was washed with saturated brine, and concentrated, and the residue was washed by suspending in ethyl acetate. This was converted to hydrochloride to give the object compound of 2-(2-(2-methylpyridin-3-yloxy)ethylamino)-6-(5-methyl-1H-pyrazol-3-ylamino)nicotinonitrile dihydrochloride (34 mg).

$^1$H-NMR (400 MHz, DMSO-$d_6$) δ(ppm): 9.96 (1H, br-s), 8.28 (1H, d), 8.14 (1H, d), 7.79 (1H, dd), 7.56 (1H, d), 7.12 (1H, br-s), 6.32 (1H, d), 6.21 (1H, s), 4.42 (2H, t), 3.84 (2H, br-s), 2.54 (3H, s), 2.16 (3H, s).

Example 29

Compound E (250 mg, 1.07 mmol), 2-(2,6-dimethylpyridin-3-yloxy)ethylamine hydrochloride (512 mg) and sodium hydrogencarbonate (901 mg) were added to DMSO (10 ml), and the mixture was stirred at 100° C. for 27 hr. After stirring, the reaction mixture was added to cold water, and the mixture was extracted with ethyl acetate. The organic layer was washed with saturated brine, and concentrated, and the residue was washed by suspending in ethyl acetate. This was converted to hydrochloride to give the object compound of 2-(2-(2,6-dimethylpyridin-3-yloxy)ethylamino)-6-(5-methyl-1H-pyrazol-3-ylamino)nicotinonitrile dihydrochloride (20 mg).

$^1$H-NMR (400 MHz, DMSO-$d_6$) δ(ppm): 9.78 (1H, br-s), 8.12 (1H, d), 8.00 (1H, d), 7.63 (1H, d), 7.10 (1H, br-s), 6.29 (1H, d), 6.14 (1H, s), 4.43 (2H, t), 3.93 (2H, br-s), 2.61 (3H, s), 2.53 (3H, s), 2.23 (3H, s).

Example 30

Compound E (272 mg, 1.17 mmol), 2-(4-trifluoromethoxyphenoxy)ethylamine hydrochloride (450 mg) and sodium hydrogencarbonate (983 mg) were added to DMSO (8 ml), and the mixture was stirred at 100° C. for 27 hr. After stirring, the reaction system was added to cold water, and the mixture was extracted with ethyl acetate. The organic layer was washed with saturated brine, and concentrated, and the residue was washed by suspending in ethyl acetate to give the object compound of 2-(2-(4-(trifluoromethoxy)phenoxy)ethylamino)-6-(5-methyl-1H-pyrazol-3-ylamino)nicotinonitrile (38 mg).

$^1$H-NMR (400 MHz, DMSO-$d_6$) δ(ppm): 9.87 (1H, br-s), 7.55 (1H, d), 7.26 (1H, d), 7.05 (1H, br-s), 7.04 (2H, d), 6.30 (1H, d), 6.25 (1H, br-s), 4.17 (2H, t), 3.77 (2H, br-s), 2.06 (3H, s).

The structural formulas of respective Example compounds 1-30 are shown in the following Tables.

TABLE 7
Example 1
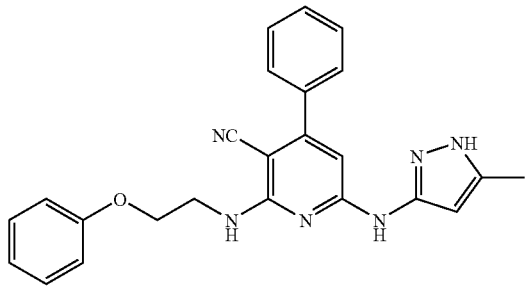
Example 2
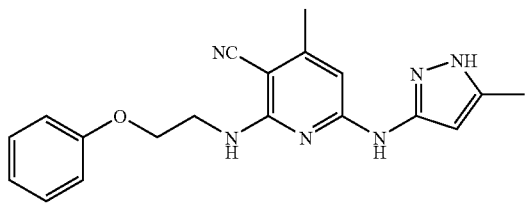
Example 3
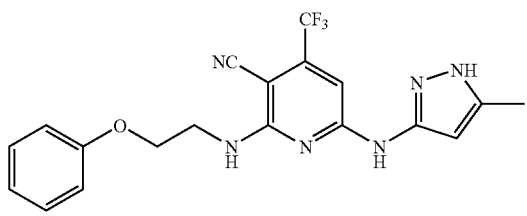
Example 4
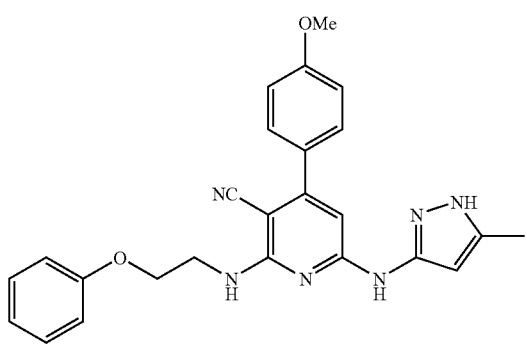
Example 5
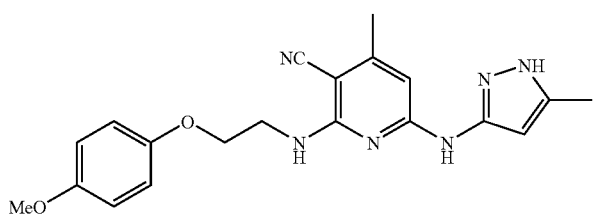
Example 6
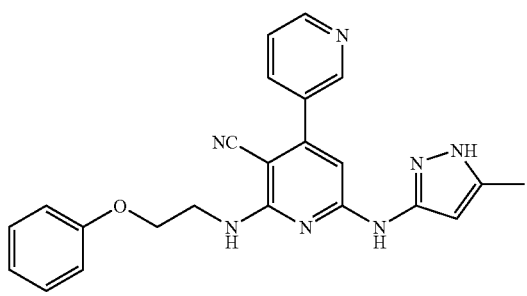

TABLE 7-continued
Example 7
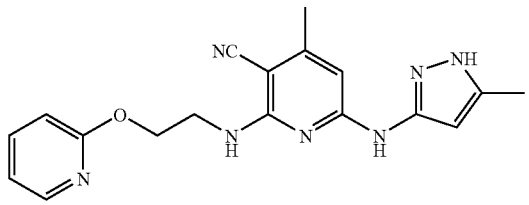
Example 8
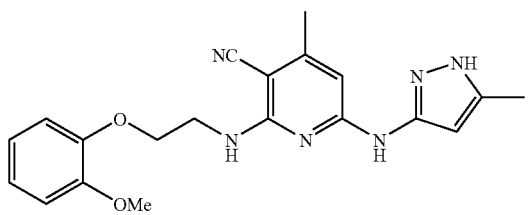
Example 9
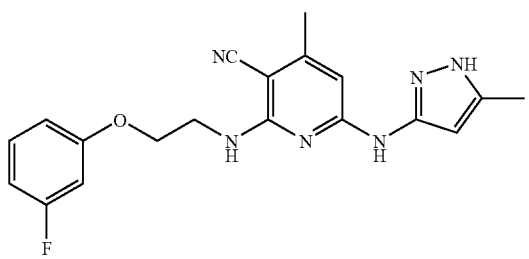
Example 10
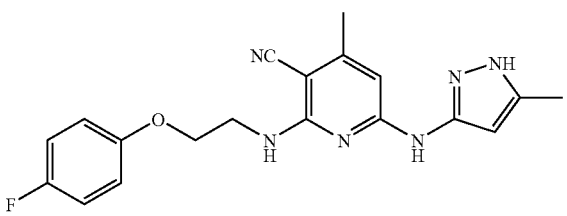
Example 11
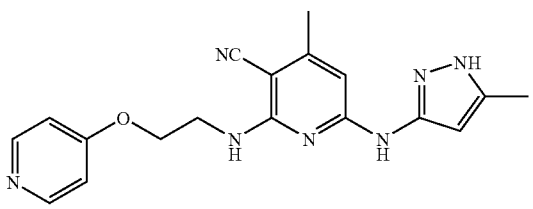
Example 12
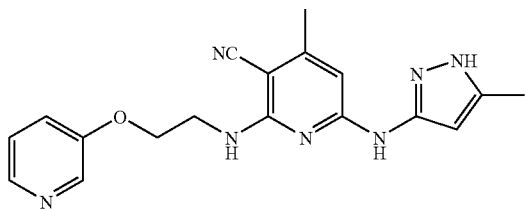
Example 13
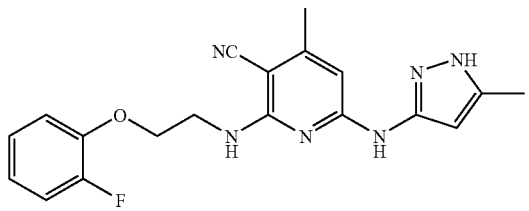

TABLE 7-continued
Example 14 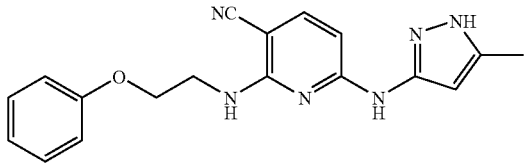
TABLE 8
Example 15 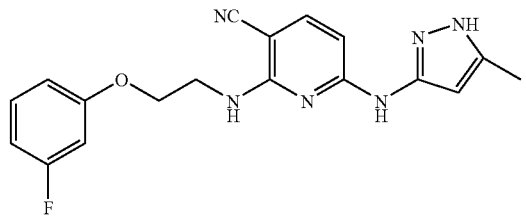
Example 16 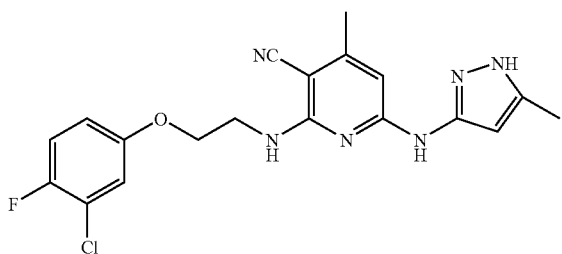
Example 17 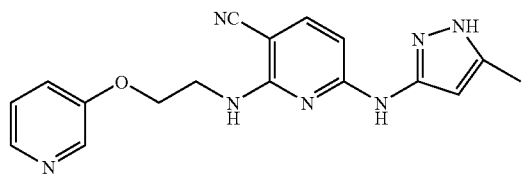
Example 18 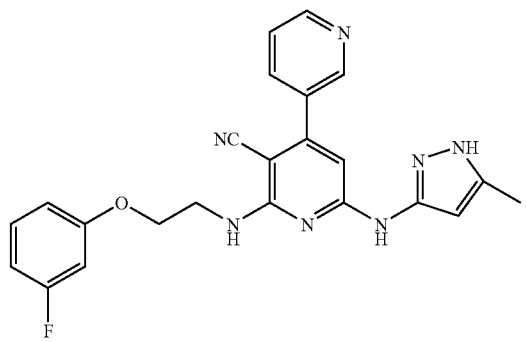
Example 19 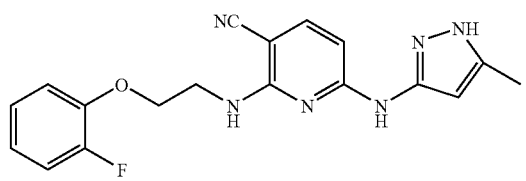

TABLE 8-continued
Example 20
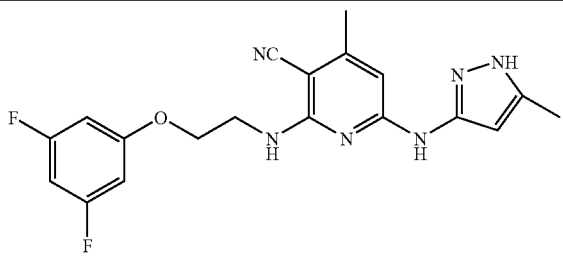
Example 21
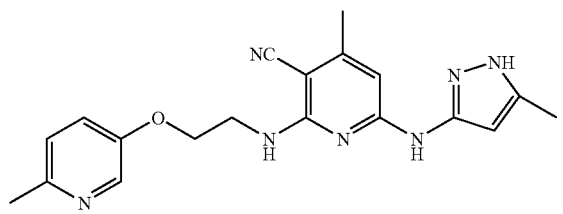
Example 22
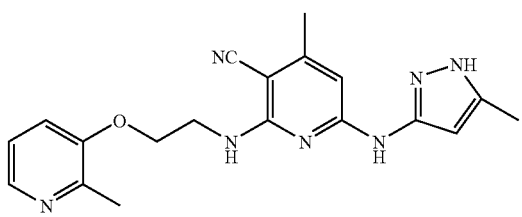
Example 23
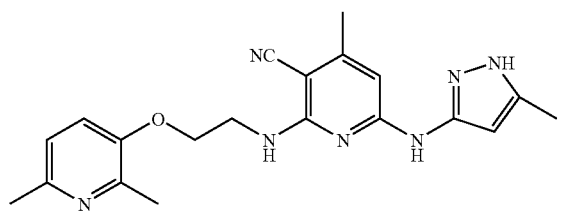
Example 24
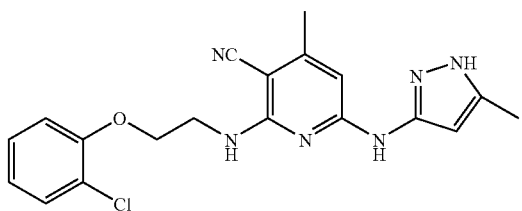
Example 25
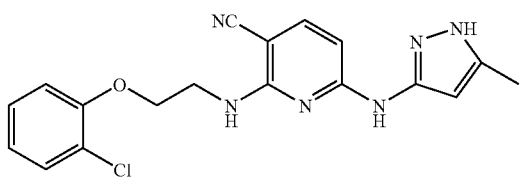

TABLE 8-continued

Example 26

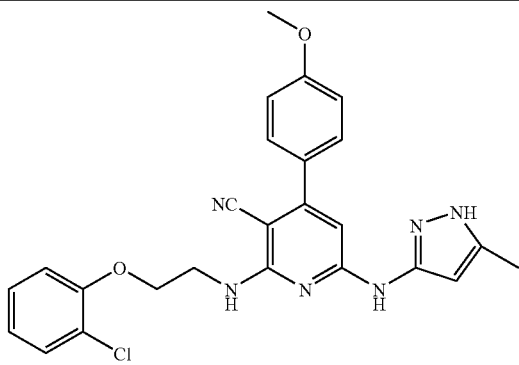

Example 27

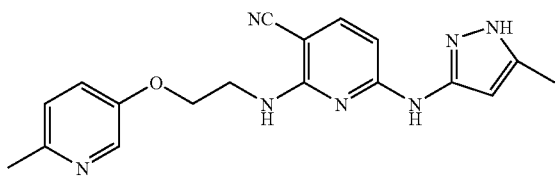

Example 28

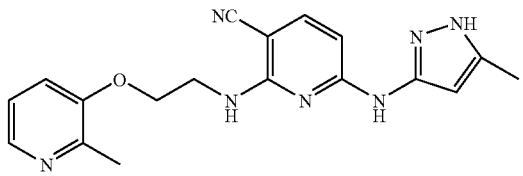

Example 29

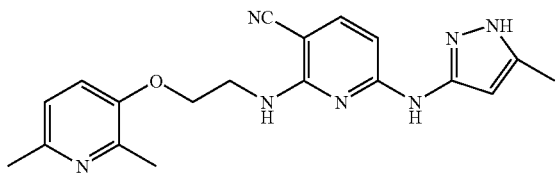

Example 30

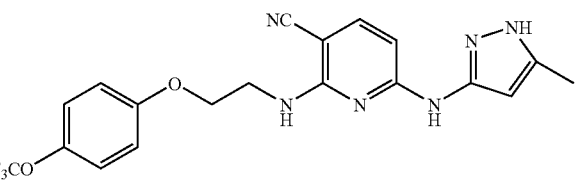

The compounds described below were synthesized in the same manner.

Example 31

2-((2-((2-((dimethylamino)methyl)pyridin-3-yl)oxy)ethyl) amino)-4-methyl-6-(5-methyl-1H-pyrazol-3-ylamino) nicotinonitrile Example 32

4-methyl-6-(5-methyl-1H-pyrazol-3-ylamino)-2-(2-(6-(piperazin-1-yl)pyridin-3-yloxy)ethylamino)nicotinonitrile Example 33

2-(2-(6-(4-acetylpiperazin-1-yl)pyridin-3-yloxy)ethylamino)-4-methyl-6-(5-methyl-1H-pyrazol-3-ylamino) nicotinonitrile Example 34

6-(5-cyclopropyl-1H-pyrazol-3-ylamino)-4-methyl-2-(2-(pyridin-3-yloxy)ethylamino)nicotinonitrile Example 35

6-(5-isopropyl-1H-pyrazol-3-ylamino)-4-methyl-2-(2-(pyridin-3-yloxy)ethylamino)nicotinonitrile Example 36

6-(5-methyl-1H-pyrazol-3-ylamino)-2-(2-(pyridin-3-yloxy) ethylamino)nicotinonitrile Example 37

4-ethyl-6-(5-methyl-1H-pyrazol-3-ylamino)-2-(2-(2-methylpyridin-3-yloxy)ethylamino)nicotinonitrile

Example 38

4-ethyl-6-(5-methyl-1H-pyrazol-3-ylamino)-2-(2-(6-methylpyridin-3-yloxy)ethylamino)nicotinonitrile

Example 39

2-(2-(2,6-dimethylpyridin-3-yloxy)ethylamino)-4-ethyl-6-(5-methyl-1H-pyrazol-3-ylamino)nicotinonitrile

Example 40

2-(2-(2,6-dimethylpyridin-3-yloxy)ethylamino)-6-(5-isopropyl-1H-pyrazol-3-ylamino)-4-methylnicotinonitrile

Example 41

2-(2-(2,6-dimethylpyridin-3-yloxy)ethylamino)-6-(5-methyl-1H-pyrazol-3-ylamino)-4-(3-morpholin-4-ylpropyl)nicotinonitrile

Example 42

2-(2-(2,6-dimethylpyridin-3-yloxy)ethylamino)-6-(5-ethyl-1H-pyrazol-3-ylamino)-4-methylnicotinonitrile

Example 43

6-(−5-ethyl-1H-pyrazol-3-ylamino)-4-methyl-2-(2-(6-methylpyridin-3-yloxy)ethylamino)nicotinonitrile

Example 44

6-(−5-ethyl-1H-pyrazol-3-ylamino)-5-methyl-2-(2-(2-methylpyridin-3-yloxy)ethylamino)nicotinonitrile

Example 45

4-methyl-2-(2-(6-methylpyridin-3-yloxy)ethylamino)-6-(1H-pyrazol-3-ylamino)nicotinonitrile

Example 46

4-cyclopropyl-2-(2-(2,6-dimethylpyridin-3-yloxy)ethylamino)-6-(5-methyl-1H-pyrazol-3-ylamino)nicotinonitrile

Example 47

2-(2-(2-ethylpyridin-3-yloxy)ethylamino)-4-methyl-6-(5-ethyl-1H-pyrazol-3-ylamino)nicotinonitrile

Example 48

2-(2-(2-ethylpyridin-3-yloxy)ethylamino)-6-(5-ethyl-1H-pyrazol-3-ylamino)nicotinonitrile

Example 49

4-methyl-2-(2-(2-methylpyridin-3-yloxy)ethylamino)-6-(5-(methylthio)-1H-pyrazol-3-ylamino)nicotinonitrile

Example 50

6-(5-methyl-1H-pyrazol-3-ylamino)-2-((pyridin-3-yloxy)propylamino)nicotinonitrile

Example 51

6-(5-cyclopropyl-1H-pyrazol-3-ylamino)-4-methyl-2-(2-(pyridin-3-yloxy)ethylamino)nicotinonitrile

Example 52

4-cyclopropyl-6-(5-methyl-1H-pyrazol-3-ylamino)-2-(2-(2-methylpyridin-3-yloxy)ethylamino)nicotinonitrile

Example 53

6-(5-cyclopropyl-1H-pyrazol-3-ylamino)-4-methyl-2-(2-(6-methylpyridin-3-yloxy)ethylamino)nicotinonitrile

Example 54

1-(5-methyl-1H-pyrazol-3-ylamino)-3-(2-(6-methylpyridin-3-yloxy)ethylamino)-6,7-dihydro-5H-cyclopenta[c]pyridine-4-carbonitrile

Example 55

4-methyl2-(2-(6-methylpyridin-3-yloxy)ethylamino)-6-(5-(methylthio)-1H-pyrazol-3-ylamino)nicotinonitrile

Example 56

6-(5-methyl-1H-pyrazol-3-ylamino)-2-(1-methyl-2-(pyridin-3-yloxy)ethylamino)nicotinonitrile

Example 57

5-fluoro-6-(5-methyl-1H-pyrazol-3-ylamino)-2-(2-(6-methylpyridin-3-yloxy)ethylamino)nicotinonitrile

Example 58

6-(5-methyl-1H-pyrazol-3-ylamino)-2-((2-phenoxyethyl)amino)-4-piperidin-4-ylnicotinonitrile

Example 59

6-(5-methyl-1H-pyrazol-3-ylamino)-2-((2-methyl-1-((pyridin-3-yloxy)methyl)propyl)amino)nicotinonitrile

Example 60

2-(2-(6-methylpyridin-3-yloxy)ethylamino)-6-(5-(methylthio)-1H-pyrazol-3-ylamino)nicotinonitrile

Example 61

6-(5-ethoxy-1H-pyrazol-3-ylamino)-4-methyl-2-(2-(6-methylpyridin-3-yloxy)ethylamino)nicotinonitrile

Example 62

4-methyl-6-(5-methyl-1H-pyrazol-3-ylamino)-2-(2-(pyrimidin-2-yloxy)ethylamino)nicotinonitrile

Example 63

N-(3-(2-(((3-cyano-4-methyl-6-(5-methyl-1H-pyrazol-3-ylamino)pyridin-2-yl)amino)ethoxy)pyridin-2-yl)acetamide

Example 64

2-(2-(2-aminopyridin-3-yloxy)ethylamino)-4-methyl-6-(5-methyl-1H-pyrazol-3-ylamino)nicotinonitrile

Example 65

6-(5-cyclopropyl-1H-pyrazol-3-ylamino)-2-(2-(pyridin-3-yloxy)ethylamino)nicotinonitrile

Example 66

6'-(5-methyl-1H-pyrazol-3-ylamino)-2'-((2-phenoxyethyl)thio)-3,4'-bipyridine-3'-carbonitrile

Example 67

4-methyl-6-(5-methyl-1H-pyrazol-3-ylamino)-2-(2-(3-thienyloxy)ethylthio)nicotinonitrile

Example 68

4-methyl-6-(5-methyl-1H-pyrazol-3-ylamino)-2-(2-(thienyloxy)ethylamino)nicotinonitrile

Example 69

4-methyl-6-(5-methyl-1H-pyrazol-3-ylamino)-2-(2-(pyridin-3-yloxy)ethylthio)nicotinonitrile

Example 70

N-(3-(2-((3-cyano-6-(5-methyl-1H-pyrazol-3-ylamino)pyridin-2-yl)amino)ethoxy)pyridin-2-yl)cyclopropanecarboxamide

Example 71

N-(3-(2-(3-cyano-4-methyl-6-(5-methyl-1H-pyrazol-3-ylamino)pyridin-2-yl)aminoethoxy)pyridin-2-yl)benzamide

Example 72 tert-butyl 4-(3-cyano-6-(5-methyl-1H-pyrazol-3-ylamino)-2-((2-phenoxyethyl)thio)pyridin-4-yl)piperidine-1-carboxylate

Example 73

N-(3-(2-((3-cyano-6-(5-methyl-1H-pyrazol-3-ylamino)pyridin-2-yl)amino)ethoxy)pyridin-2-yl)acetamide

Example 74

N-(3-(2-((3-cyano-4-methyl-6-(5-methyl-1H-pyrazol-3-ylamino)pyridin-2-yl)amino)ethoxy)pyridin-2-yl)cyclopropanecarboxamide

Example 75

6-(5-methyl-1H-pyrazol-3-ylamino)-2-((2-phenoxyethyl)thio)-4-piperidin-4-ylnicotinonitrile

Example 76

4-methyl-6-(5-methyl-1H-pyrazol-3-ylamino)-2-(2-((3-oxo-2,3-dihydro-1H-isoindol-5-yl)oxy)ethylamino)nicotinonitrile

Example 77

6-(4,6-dihydro-1H-thieno[3,4,c]pyrazol-3-ylamino)-4-methyl-2-((2-((2-methylpyridin-3-yl)oxy)ethyl)amino)nicotinonitrile

Example 78

6-(5-(dimethylamino)-1H-pyrazol-3-ylamino)-4-methyl-2-(2-(6-methylpyridin-3-yl)oxyethyl)amino)nicotinonitrile

Example 79

4-(1-acetylpiperidin-4-yl)-6-(5-methyl-1H-pyrazol-3-ylamino)-2-(2-(6-methylpyridin-3-yloxy)ethylamino)nicotinonitrile

Example 80

4-methyl-6-(5-methyl-1H-pyrazol-3-ylamino)-2-(2-(6-methylpyridin-3-yloxy)ethylthio)nicotinonitrile

Example 81

4-methyl-6-(5-methyl-1H-pyrazol-3-ylamino)-2-(2-(pyrimidin-2-yloxy)ethylthio)nicotinonitrile

Example 82

6-(5-methyl-1H-pyrazol-3-ylamino)-2-(2-(6-methylpyridin-3-yloxy)ethylthio)nicotinonitrile

Example 83

6-(5-hydroxy-1H-pyrazol-3-ylamino)-4-methyl-2-(2-(6-methylpyridin-3-yloxy)ethylamino)nicotinonitrile

Example 84

6-(5-cyclopropyl-1H-pyrazol-3-ylamino)-2-(2-(2,6-dimethylpyridin-3-yloxy)ethylamino)-4-methylnicotinonitrile

Example 85

6-(5-cyclopropyl-1H-pyrazol-3-ylamino)-2-(2-(2,6-dimethylpyridin-3-yloxy)ethylamino)nicotinonitrile

Example 86

5-fluoro-6-(5-methyl-1H-pyrazol-3-ylamino)-2-(2-(2-methylpyridin-3-yloxy)ethylamino)nicotinonitrile

Example 87

2-(2-(6-ethylpyridin-3-yloxy)ethylamino)-4-methyl-6-(5-methyl-1H-pyrazol-3-ylamino)nicotinonitrile

Example 88

2-(2-(3-cyanophenoxy)ethylamino)-4-methyl-6-(5-methyl-1H-pyrazol-3-ylamino)nicotinonitrile

Example 89

2-(2-(3-nitrophenoxy)ethylamino)-4-methyl-6-(5-methyl-1H-pyrazol-3-ylamino)nicotinonitrile

Example 90

2-(2-(6-bromopyridin-3-yloxy)ethylamino)-6-(5-methyl-1H-pyrazol-3-ylamino)nicotinonitrile

Example 91

2-(2-(2-methoxyphenoxy)ethylamino)-6-(5-methyl-1H-pyrazol-3-ylamino)-4-piperidin-4-ylnicotinonitrile

Example 92

2-((1S)-1-methyl-2-(6-methylpyridin-3-yloxy)ethylamino)-6-(5-methyl-1H-pyrazol-3-ylamino)nicotinonitrile

Example 93

4-methyl-2-((1S)-1-methyl-2-((6-methylpyridin-3-yl)oxy)ethylamino)-6-(5-methyl-1H-pyrazol-3-ylamino)nicotinonitrile

Example 94

2-((1S)-1-methyl-2-(6-methylpyridin-3-yloxy)ethylamino)-6-(5-methyl-1H-pyrazol-3-ylamino)-4-piperidin-4-ylnicotinonitrile

Example 95

2-(2-(2-aminopyridin-3-yloxyethyl)amino)-6-(5-methyl-1H-pyrazol-3-ylamino)nicotinonitrile

Example 96

2-(1-methyl-2-(6-methylpyridin-3-yloxy)ethylamino)-6-(5-methyl-1H-pyrazol-3-ylamino)nicotinonitrile

Example 97

2-(2-(2-methylpyridin-3-yloxy)ethylamino)-6-(5-methyl-1H-pyrazol-3-ylamino)-4-piperidin-4-ylnicotinonitrile

Example 98

2-(2-(2,6-dimethylpyridin-3-yloxy)ethylamino)-6-(5-methyl-1H-pyrazol-3-ylamino)-4-piperidin-4-ylnicotinonitrile

Example 99

6-(5-methyl-1H-pyrazol-3-ylamino)-2-(2-(6-methylpyridin-3-yloxy)ethylamino)-4-piperidin-4-ylnicotinonitrile

Example 100

3-((5-cyano-4-methyl-6-(2-(2-methylpyridin-3-yloxy)ethylamino)pyridin-2-yl)amino-N-propyl-1H-pyrazole-5-carboxamide

Example 101

4-methyl-6-(5-methyl-1H-pyrazol-3-ylamino)-2-(2-(6-morpholin-4-ylpyridin-3-yloxy)ethylamino)-nicotinonitrile

Example 102

4-methyl-2-(2-(6-(4-methylpiperazin-1-yl)pyridin-3-yloxy)ethylamino)-6-(5-methyl-1H-pyrazol-3-ylamino)nicotinonitrile

Example 103

2-(2-(3-fluorophenoxy)ethylamino)-6-(5-methyl-1H-pyrazol-3-ylamino)-4-piperidin-4-ylnicotinonitrile

Example 104

2-(2-(4-fluorophenoxy)ethylamino)-6-(5-methyl-1H-pyrazol-3-ylamino)-4-piperidin-4-ylnicotinonitrile

Example 105

4-methyl-6-(5-methyl-1H-pyrazol-3-ylamino)-2-(2-(3-morpholin-4-ylphenoxy)ethylamino)nicotinonitrile

Example 106

6-(5-methyl-1H-pyrazol-3-ylamino)-2-(2-(3-morpholin-4-ylphenoxy)ethylamino)nicotinonitrile

Example 107

4-methyl-6-(5-methyl-1H-pyrazol-3-ylamino)-2-(2-(4-morpholin-4-ylphenoxy)ethylamino)nicotinonitrile

Example 108

2-(2-(2-fluorophenoxy)ethylamino)-6-(5-methyl-1H-pyrazol-3-ylamino)-4-piperidin-4-ylnicotinonitrile

Example 109

2-(2-(2-methylphenoxy)ethylamino)-6-(5-methyl-1H-pyrazol-3-ylamino)-4-piperidin-4-ylnicotinonitrile

Example 110

2-(2-(4-(dimethylamino)phenoxy)ethylamino)-4-methyl-6-(5-methyl-1H-pyrazol-3-ylamino)nicotinonitrile

Example 111

2-(2-(4-(dimethylamino)phenoxy)ethylamino)-6-(5-methyl-1H-pyrazol-3-ylamino)nicotinonitrile

Example 112

2-(2-(4-methylphenoxy)ethylamino)-6-(5-methyl-1H-pyrazol-3-ylamino)-4-piperidin-4-ylnicotinonitrile

Example 113

6-(5-methyl-1H-pyrazol-3-ylamino)-2-(2-(4-(1H-1,2,4-triazol-1-yl)phenoxy)ethylamino)-nicotinonitrile

Example 114

4-methyl-6-(5-methyl-1H-pyrazol-3-ylamino)-2-(2-(4-(1H-1,2,4-triazol-1-yl)phenoxy)ethylamino)nicotinonitrile

Example 115

4-(1-(N-methylglycyl)piperidin-4-yl)-6-(5-methyl-1H-pyrazol-3-ylamino)-2-((2-phenoxyethyl)amino)nicotinonitrile

Example 116

4-(1-(N,N-dimethyl-β-alanyl)piperidin-4-yl)-6-(5-methyl-1H-pyrazol-3-ylamino)-2-(2-phenoxyethylamino)nicotinonitrile

Example 117

2-2-(3-cyanophenoxy)ethylamino)-6-(5-methyl-1H-pyrazol-3-ylamino)-4-piperidin-4-ylnicotinonitrile

Example 118 ethyl 3-(2-((3-cyano-6-(5-methyl-1H-pyrazol-3-ylamino)-4-piperidin-4-ylpyridin-2-yl)amino)ethoxy)benzoate

Example 119 methyl 4-(2-(3-cyano-4-methyl-6-(5-methyl-1H-pyrazol-3-ylamino)pyridin-2-yl)amino)ethoxy)benzoate

Example 120

4-(2-(3-cyano-4-methyl-6-(5-methyl-1H-pyrazol-3-ylamino)pyridin-2-yl)aminoethoxy)benzoic acid

Example 121

4-(1-(azetidin-3-ylcarbonyl)piperidin-4-yl)-6-(5-methyl-1H-pyrazol-3-ylamino)-2-(2-phenoxyethylamino)nicotinonitrile

Example 122

4-(1-(2-hydroxyethyl)piperidin-4-yl)-6-(5-methyl-1H-pyrazol-3-ylamino)-2-(2-phenoxyethylamino)nicotinonitrile

Example 123

4-(2-(3-cyano-4-methyl-6-(5-methyl-1H-pyrazol-3-ylamino)pyridin-2-yl)aminoethoxy)-N,N-dimethyl benzamide

Example 124

6-(5-methyl-1H-pyrazol-3-ylamino)-4-piperidin-4-yl-2-(2-(pyridin-3-yloxy)ethylamino)nicotinonitrile

Example 125

4-(1-(N,N-dimethyl-β-alanyl)piperidin-4-yl-6-(5-methyl-1H-pyrazol-3-ylamino)-2-(2-(pyridin-3-yloxy)ethylamino)nicotinonitrile

Example 126

4-(1-(N-methylglycyl)piperidin-4-yl-6-(5-methyl-1H-pyrazol-3-ylamino)-2-(2-(pyridin-3-yloxy)ethylamino)nicotinonitrile

Example 127

6-(5-methyl-1H-pyrazol-3-ylamino)-2-(2-(6-methylpyridin-3-yloxy)ethylamino)-4-(2-thienyl)nicotinonitrile

Example 128

6-(5-(hydroxymethyl)-1H-pyrazol-3-ylamino)-4-methyl-2-(2-(6-methylpyridin-3-yloxy)ethylamino)nicotinonitrile

Example 129

4-methyl-2-(2-(6-methyl-1-oxy-pyridin-3-yloxy)ethylamino)-6-(5-(hydroxymethyl)-1H-pyrazol-3-ylamino) nicotinonitrile The structural formulas and analysis data of the Example compounds are shown below.

TABLE 9

| EX | Structural formula | NMR(ppm) and Mass |
|----|--------------------|-------------------|
| 31 | | 9.82(br-s, 1H), 9.50(br-, 1H), 8.24(d, 1H), 7.60(d, 1H), 7.46(dd, 1H), 6.66(br-s, 1H), 6.28(s, 1H), 6.20(br-s, 1H), 4.40(s, 2H), 4.28(dd, 2H), 3.84(dd, 2H), 2.80(s, 6H), 2.20(s, 3H), 2.08(s, 3H) |
| 32 | | 11.84(s, 1H), 9.90(br-s, 1H), 7.10-7.00(m, 4H), 6.86(br-s, 1H), 6.52(br-s, 1H), 5.44(s, 1H), 3.60-3.44(m, 6H), 3.40-3.10(m, 6H), 2.04(s, 3H), 2.00(s, 3H) m/z = 434(M + H) |

TABLE 9-continued
| EX | Structural formula | NMR(ppm) and Mass |
|---|---|---|
| 33 | | 9.92(br-s, 1H), 7.50(d, 2H), 7.02(d, 2H), 6.96(br-s, 1H), 6.24(d, 1H), 4.14(dd, 2H), 3.90-3.68(m, 6H), 3.40-3.24(m, 4H), 2.24(s, 3H), 2.10(s, 3H), 2.04(s, 3H) |
| 34 | | 9.52(s, 1H), 8.42(d, 1H), 8.28(d, 1H), 7.68(dd, 1H), 7.54(dd, 1H), 6.86(br-s, 1H), 6.16(br-s, 1H), 6.10(s, 1H), 4.24(dd, 2H), 3.76(dd, 2H), 2.20(s, 6H), 1.80-1.70(m, 1H), 1.84-1.78(m, 2H), 1.54-1.48(m, 2H) m/z = 376(M + H) |
| 35 | | 9.56(s, 1H), 8.38(br-s, 1H), 8.25(br-s, 1H), 7.58(br-s, 1H), 7.48(br-s, 1H), 6.86(br-s, 1H), 6.30(br-s, 1H), 6.19(br-s, 1H), 4.24(t, 2H), 3.81(m, 2H), 2.79(m, 1H), 2.19(s, 3H), 1.11(d, 6H) |
| 36 | | 10.08(s, 1H), 8.68(s, 1H), 8.48(dd, 1H), 8.15(dd, 1H), 7.90(dd, 1H), 7.58(d, 1H), 7.14(br-s, 1H), 6.34(d, 1H), 6.24(s, 1H), 4.40(dd, 2H), 3.84(dd, 2H), 2.15(s, 3H) |
| 37 | | 9.84(s, 1H), 8.26(d, 1H), 8.14(d, 1H), 7.76(dd, 1H), 6.92(br-s, 1H), 6.26(s, 1H), 6.16(s, 1H), 4.40(dd, 2H), 3.80(dd, 2H), 2.56(s, 3H), 2.54(q, 2H), 2.14(s, 3H), 1.14(t, 3H) |
TABLE 10
| EX | Structural formula | NMR(ppm) and Mass |
|---|---|---|
| 38 | 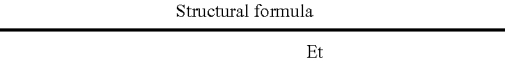 | 9.84(s, 1H), 8.30(d, 1H), 8.08(dd, 1H), 7.76(d, 1H), 6.92(br-s, 1H), 6.26(s, 1H), 6.20(s, 1H), 4.36(dd, 2H), 3.80(dd, 2H), 2.62(s, 3H), 2.54(q, 2H), 2.14(s, 3H), 1.14(t, 3H) |

TABLE 10-continued

| EX | Structural formula | NMR(ppm) and Mass |
|---|---|---|
| 39 | | 9.88(s, 1H), 8.06(d, 1H), 7.60(d, 1H), 6.94(br-s, 1H), 6.26(s, 1H), 6.20(s, 1H), 4.36(dd, 2H), 3.80(dd, 2H), 2.60(s, 3H), 2.56(q, 2H), 2.50(s, 3H), 2.16(s, 3H), 1.12(t, 3H) |
| 40 | | 9.64(s, 1H), 8.09(d, 1H), 7.61(d, 1H), 6.91(br-s, 1H), 6.26(s, 1H), 6.21(s, 1H), 4.36(t, 2H), 3.82(m, 2H), 2.85(m, 1H), 2.59(s, 3H), 2.49(s, 3H), 2.20(s, 3H), 1.15(d, 6H) |
| 41 | | 13.71(br-s, 1H), 8.06(d, 1H), 7.61(d, 1H), 6.81(br-s, 1H), 6.01(s, 1H), 5.58(s, 1H), 4.31, (t-like, 2H), 4.0-3.0(m, 10H), 2.6-2.2(m, 2H), 2.74, 2.27, 2.05(each s, each 3H), 1.9-1.6(m, 2H) m/z = 491(M + H) |
| 42 | | 9.56(s, 1H), 8.08(d, 1H), 7.60(d, 1H), 6.88(br-s, 1H), 6.22(s, 1H), 6.20(s, 1H), 4.37(t, 2H), 3.81(m, 2H), 2.58(s, 3H), 2.60-2.40(maskedsignal, 2H), 2.47(s, 3H), 2.19(s, 3H), 1.11(t, 3H) |
| 43 | | 9.72(s, 1H), 8.50(d, 1H), 8.08(dd, 1H), 7.77(d, 1H), 6.92(br-s, 1H), 6.24(s, 2H), 4.35(t, 2H), 3.81(m, 2H), 2.63(s, 3H), 2.60-2.40(maskedsignal, 2H), 2.21(s, 3H), 1.10(t, 3H) |
| 44 | | 9.14(br-s, 1H), 8.24(d, 1H), 8.06(d, 1H), 7.72(dd, 1H), 7.48(s, 1H), 7.10(br-s, 1H), 6.32(s, 1H), 4.34(dd, 2H), 3.76(dd, 2H), 2.60(s, 3H), 2.18(s, 3H), 2.08(s, 3H) |

TABLE 10-continued

| EX | Structural formula | NMR(ppm) and Mass |
|---|---|---|
| 45 | (structure) | 9.66(s, 1H), 8.51(d, 1H), 8.10(dd, 1H), 7.77(d, 1H), 7.54(d, 1H), 6.87(br-s, 1H), 6.39(s, 1H), 6.25(s, 1H), 4.37(t, 2H), 3.81(m, 2H), 2.63(s, 3H), 2.20(s, 3H) |

TABLE 11

| EX | Structural formula | NMR(ppm) and Mass |
|---|---|---|
| 46 | (structure) | 9.94(s, 1H), 8.07(d, 1H), 7.58(d, 1H), 7.05(s, 1H), 6.15(s, 1H), 5.88(s, 1H), 4.35(t-like, 2H), 3.79(t-like, 2H), 2.58, 2.48, 2.15(each S, each 3H), 1.90(m, 1H), 1.2-0.9(m, 2H), 0.8-0.6(m, 2H) m/z = 404(M + H) |
| 47 | (structure) | 9.92(s, 1H), 8.30(d, 1H), 8.14(dd, 1H), 7.80(dd, 1H), 7.06(br-s, 1H), 6.28(s, 1H), 6.22(s, 1H), 4.40(dd, 2H), 3.88(br-s, 2H), 2.92(q, 2H), 2.22(s, 3H), 2.18(s, 3H), 1.14(t, 3H) m/z = 378(M + H) |
| 48 | (structure) | 9.86(s, 1H), 8.30(d, 1H), 8.14(d, 1H), 7.78(dd, 1H), 7.56(d, 1H), 7.06(br-s, 1H), 6.32(d, 1H), 6.20(s, 1H), 4.42(dd, 2H), 3.86(br-s, 2H), 2.92(q, 2H), 2.18(s, 3H), 1.14(t, 3H) |
| 49 | (structure) | 12.40(s, 1H), 9.65(s, 1H), 7.95(d, 1H), 7.29(d, 1H), 7.11(dd, 1H), 6.84(t, 1H), 6.53(s, 1H), 6.17(s, 1H), 4.13(t, 2H), 3.78(m, 2H), 2.32, 2.30, 2.18(each s, each 3H), m/z = 396(M + H) |
| 50 | (structure) | 9.86(br-s, 1H), 8.58(d, 1H), 8.42(d, 1H), 8.03(dd, 1H), 7.81(dd, 1H), 7.51(d, 1H), 7.07(br-s, 1H), 6.29(d, 1H), 6.25(s, 1H), 5.01(m, 1H), 3.68(m, 2H), 2.11(s, 3H), 1.34(d, 3H) |

TABLE 11-continued

| EX | Structural formula | NMR(ppm) and Mass |
|---|---|---|
| 51 | | 9.66(br-s, 1H), 8,61(s, 1H), 8.44(s, 1H), 8.00(d, 1H), 7.81(m, 1H), 6.92(br-s, 1H), 8.21(s, 1H), 6.13(s, 1H), 4.33(t, 2H), 2.20(s, 3H), 1.79(m, 1H), 0.85(m, 2H), 0.59(m, 2H) |
| 52 | | 9.79(br-s, 1H), 8.29(d, 1H), 8.14(d, 1H), 7.78(dd, 1H), 7.01(br-s, 1H), 6.17(s, 1H), 5.93(br-s, 1H), 4.41(t, 2H), 3.84(m, 2H), 2.54(s, 3H), 2.16(s, 3H), 1.93(m, 1H), 1.09(m, 2H), 0.71(m, 2H) |
| 53 | | 9.65(s, 1H), 8.50(d, 1H), 8.08(dd, 1H), 7.77(d, 1H), 6.90(br-s, 1H), 6.21(s, 1H), 6.10(s, 1H), 4.33(t, 2H), 3.79(m, 2H), 2.62(s, 3H), 2.20(s, 3H), 1.79(m, 1H), 0.86(m, 2H), 0.59(m, 2H) |

TABLE 12

| EX | Structural formula | NMR(ppm) and Mass |
|---|---|---|
| 54 | | 9.60(s, 1H), 8.46(d, 1H), 8.06(dd, 1H), 7.76(d, 1H), 7.16(br-s, 1H), 6.28(s, 1H), 4.34(dd, 2H), 3.88(br-s, 2H), 2.88-2.50(m, 4H), 2.64(s, 3H), 2.18(s, 3H), 2.10-2.00(m, 2H) m/z = 390(M + H) |
| 55 | | 9.70(s, 1H), 8.50(d, 1H), 8.07(dd, 1H), 7.76(d, 1H), 6.93(br-s, 1H), 6.41(s, 1H), 6.16(s, 1H), 4.34(t, 2H), 3.80(m, 2H), 2.62(s, 3H), 2.37(s, 3H), 2.20(s, 3H) m/z = 396(M + H) |
| 56 | | 9.60(s, 1H), 8.44(d, 1H), 8.26(d, 1H), 7.66(d, 1H), 7.50(m, 2H), 6.55(d, 1H), 6.32(br-s, 1H), 6.16(s, 1H), 4.60(m, 1H), 4.33(m, 1H), 4.03(m, 1H), 2.07(s, 3H), 1.33(d, 3H) |

TABLE 12-continued
| EX | Structural formula | NMR(ppm) and Mass |
|---|---|---|
| 57 | 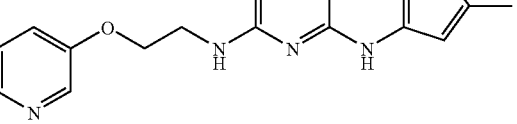 | 9.78(s, 1H), 8.48(d, 1H), 8.07(dd, 1H), 7.76(d, 1H), 7.68(d, 1H), 7.07(s, 1H), 6.28(s, 1H), 4.33(t, 2H), 3.73(m, 2H), 2.62, 2.12(each s, each 3H) |
| 58 | 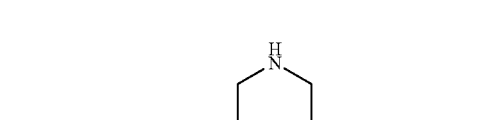 | 10.34(s, 1H), 9.10(s, 2H), 7.3-7.0(m, 3H), 7.07(br-s, 1H), 7.0-8.8(m, 2H), 6.31, 6.27(each s, each 1H), 4.11(t, 2H) 3.76(m, 2H), 3.5-2.8(m, 5H), 2.09(s, 3H), 2.0-1.6(m, 4H) m/z = 418(M + H) |
| 59 | 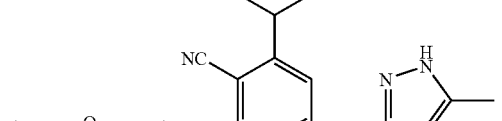 | 9.59(s, 1H), 8.44(d, 1H), 8.28(d, 1H), 7.70(d, 1H), 7.53(m, 2H), 6.41(d, 1H), 6.26(m, 2H), 4.35(m, 3H), 2.15(s, 3H), 2.11(m, 1H), 1.00(d, 6H) |
| 60 | 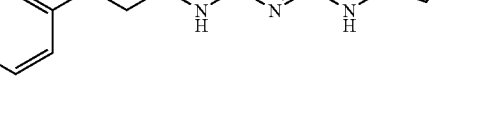 | 9.83(s, 1H), 8.52(d, 1H), 8.10(dd, 1H), 7.80(d, 1H), 7.55(d, 1H), 7.04(br-s, 1H), 6.43(s, 1H), 6.25(d, 1H), 4.35(t, 2H), 3.81(m, 2H), 2.63(s, 3H), 2.37(s, 3H) |
| 61 | 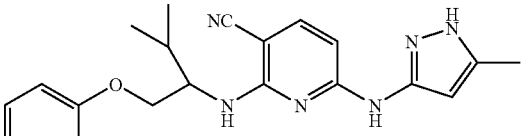 | 9.77(s, 1H), 8.50(d, 1H), 8.07(dd, 1H), 7.77(d, 1H), 7.00(br-s, 1H), 6.08(s, 1H), 5.65(s, 1H), 4.35(t, 2H), 4.02(q, 2H), 3.80(m, 2H), 2.62(s, 3H), 2.22(s, 3H), 1.25(t, 3H) |
TABLE 13
| EX | Structural formula | NMR(ppm) and Mass |
|---|---|---|
| 62 |  | 9.54(br-s, 1H), 8.58(d, 2H), 7.12(dd, 1H), 6.88(br-s, 1H), 6.28(br-s, 1H), 6.20(br-s, 1H), 4.48(dd, 2H), 3.78(dd, 2H), 2.20(s, 3H), 2.10(s, 3H) m/z = 351(M + H) |

TABLE 13-continued

| EX | Structural formula | NMR(ppm) and Mass |
|---|---|---|
| 63 | | 10.16(br-s, 1H), 9.50(br-s, 1H), 7.94(d, 1H), 7.70(d, 1H), 7.26(dd, 1H) 6.88(br-s, 1H), 6.26(br-s, 1H), 6.10(s, 1H), 4.28(dd, 2H), 3.80(dd, 2H), 2.20(s, 3H), 2.16(s, 3H), 2, 10(s, 3H) |
| 64 | | 9.88(br-s, 1H), 8.20(br-s, 2H), 7.50(d, 1H), 7.40(d, 1H), 7.16(br-s, 1H), 6.74(dd, 1H), 6.26(br-s, 1H), 6.20(s, 1H), 4.20(dd, 2H), 3.84(dd, 2H), 2.24(s, 3H), 2.16(s, 3H) |
| 65 | | 9.66(s, 1H), 8.49(d, 1H), 8.32(m, 1H), 7.76(m, 1H), 7.61(dd, 1H), 7.50(d, 1H), 6.97(m, 1H), 6.27(m, 1H), 6.15(s, 1H), 4.28(t, 2H), 3.79(m, 2H), 1.75(m, 1H), 0.82(m, 2H), 0.57(m, 2H) |
| 66 | | 11.92(s, 1H), 9.80(br-s, 1H), 8.67(s-like, 2H), 7.90(dd, 1H), 7.53(dd, 1H), 7.4-7.2(m, 2H), 7.06(s, 1H), 7.0-6.8(m, 3H), 6.27(br-s, 2H), 4.15(t, 2H), 3.9-3.7(m, 2H), 1.97(s, 3H) m/z = 429(M + H) |
| 67 | | 10.06(s, 1H), 7.40(d, 1H), 6.80(d, 2H), 6.58(s, 1H), 6.14(s, 1H), 4.14(dd, 2H), 3.60(dd, 2H), 2.30(s, 3H), 2.14(s, 3H) |
| 68 | | 9.84(s, 1H), 7.40(dd, 1H), 6.94(br-s, 1H), 6.76(d, 2H), 6.56(d, 1H), 6.26(s, 1H), 6.20(s, 1H), 4.04(dd, 2H), 3.72(dd, 2H), 2.20(s, 3H), 2.10(s, 3H) |
| 69 | | 9.90(s, 1H), 8.57(s, 1H), 8.30(dd, 1H), 7.70(dd, 1H), 7.58(dd, 1H), 6.83(br-s, 1H), 6.10(s, 1H), 4.40(dd, 2H), 3.68(dd, 2H), 2.30(s, 3H), 2.06(s, 3H) |

TABLE 14

| EX | Structural formula | NMR(ppm) and Mass |
|----|-------------------|-------------------|
| 70 | | 11.24(br-s, 1H), 9.92(br-s, 1H), 8.00(d, 1H), 7.94(d, 1H), 7.56(d, 1H), 7.44(dd, 1H), 6.32(d, 1H), 6.20(s, 1H), 4.44(dd, 2H), 3.88(br-s, 2H), 2.50-2.40(m, 1H), 2.16(s, 3H), 1.08-0.92(m, 4H) |
| 71 | | 10.04(br-s, 1H), 8.06(d, 1H), 7.98(d, 1H), 7.84(d, 2H), 7.64(dd, 1H), 7.60-7.40(m, 3H), 7.08(br-s, 1H), 6.20(s, 1H), 4.34(dd, 2H), 3.82(br-s, 2H), 2.20(s, 3H), 2.10(s, 3H) |
| 72 | | 12.04(s, 1H), 9.96(s, 1H), 7.27(t, 2H), 7.0-6.9(m, 4H), 6.13(br-s, 1H), 4.21(t, 2H), 4.15-4.0(m, 2H), 3.63(t, 2H), 2.9-2.7(m, 3H), 2.10(s, 3H), 1.79(d, 2H), 1.5-1.35(m, 11H) |
| 73 | | 10.00(br-s, 1H), 8.06(d, 1H), 7.94(d, 2H), 7.82(d, 1H), 7.62(dd, 1H), 7.60-7.44(m, 3H), 7.40(ddd, 1H), 7.10(br-s, 1H), 6.30(d, 1H), 6.22(s, 1H), 4.34(dd, 2H), 3.82(br-s, 2H), 2.10(s, 3H) |
| 74 | | 11.26(br-s, 1H), 9.96(br-s, 1H), 8.04(d, 1H), 7.94(d, 1H), 7.44(dd, 1H) 7.14(br-s, 1H), 6.26(s, 1H), 6.20(s, 1H), 4.44(dd, 2H), 3.88(br-s, 2H), 2.50-2.40(m, 1H), 2.26(s, 3H), 2, 16(s, 3H), 1.08-0.92(m, 4H) |

TABLE 15

| EX | Structural formula | NMR(ppm) and Mass |
|---|---|---|
| 75 | | 12.04(s, 1H), 9.99(s, 1H), 7.28(t, 2H) 7.0-6.88(m, 4H), 6.13(br-s, 1H), 4.21(t, 2H) 3.63(t, 2H), 3.12(d, 2H), 2.8-2.6(m, 3H) 2.11(s, 3H), 1.76(d, 2H), 1.76(d, 2H), 1.51(q, 2H)<br>m/z = 435(M + H) |
| 76 | | 9.72(s, 1H), 8.30(s, 1H), 7.54(d, 1H), 7.14(s, 1H), 6.98(d, 1H), 6.94(br-s, 1H), 6.20(br-s, 2H), 4.26(s, 2H), 4.20(dd, 2H), 3.72(dd, 2H), 2.20(s, 3H), 2.06(s, 3H) |
| 77 | | 9.32(s, 1H), 8.29(d, 1H), 8.06(d, 1H), 7.75(dd, 1H), 6.90(br-s, 1H), 6.18(s, 1H), 4.34(t, 2H), 3.87(s, 2H), 3.78(m, 2H), 3.71(s, 2H), 2.48(s, 3H), 2.21(s, 3H) |
| 78 | | 10.31(s, 1H), 8.39(d, 1H), 7.82(dd, 1H), 7.59(d, 1H), 7.17(br-s, 1H), 6.18(s, 1H), 5.82(s, 1H), 4.30(t, 2H), 3.82(m, 2H), 2.85(s, 6H), 2.55(s, 3H), 2.26(s, 3H) |
| 79 | | 10.67(s, 1H), 8.46(d, 1H), 8.08(dd, 1H), 6.30, 6.29(each s, each 1H), 4.6-4.3(m, 3H), 4.1-3.7(m, 3H), 3.3-2.5(m, 3H), 2.48, 2.20, 2.00(each s,each, 3H), 1.9-1.2(m, 4H) |
| 80 | | 9.92(br-s, 1H), 8.40(d, 1H), 7.76(dd, 1H), 7.54(dd, 1H), 8.80(br-s, 1H), 6.08(s, 1H), 4.34(dd, 2H), 3.84(dd, 2H), 2.28(s, 3H), 2.12(s, 3H) |

TABLE 16

| EX | Structural formula | NMR(ppm) and Mass |
|---|---|---|
| 81 | | 9.92(br-s, 1H), 8.60(d, 2H), 7.14(t, 1H), 6.80(br-s, 1H), 6.10(br-s, 1H), 4.50(dd, 2H), 3.54(dd, 2H), 2.30(s, 3H), 2.18(s, 3H) |
| 82 | | 10.04(br-s, 1H), 8.40(d, 1H), 7.82(dd, 1H), 7.80(dd, 1H), 7.54(d, 1H), 6.90(br-s, 1H), 6.10(br-s, 1H), 4.36(dd, 2H), 3.60(dd, 2H), 2.14(s, 3H) m/z = 367(M + H) |
| 83 | | 10.47(s, 1H), 8.48(br-s, 1H), 8.05(d, 1H), 7.74(d, 1H), 7.15(br-s, 1H), 6.19(s, 1H), 5.86(s, 1H), 4.42(br-s, 2H), 3.81(br-s, 2H), 2.63(s, 3H), 2.25(s, 3H) m/z = 366(M + H) |
| 84 | | 9.96(br-s, 1H), 8.10(d, 1H), 7.60(d, 1H), 7.06(br-s, 1H), 6.20(s, 1H), 6.10(s, 1H), 4.32(dd, 2H), 3.80(br-s, 2H), 2.60(s, 3H), 2,50(s, 3H), 2.20(s, 3H), 1.90-1.80(m, 1H), 0.96-0.84(m, 2H), 0.70-0.60(m, 1H) |
| 85 | | 9.98(br-s, 1H), 8.10(d, 1H), 7.62(d, 1H), 7.56(d, 1H), 7.10(br-s, 1H), 6.24(d, 1H), 6.10(s, 1H), 4.36(dd, 2H), 3.80(br-s, 2H), 2.60(s, 3H), 2, 50(s, 3H), 1.90-1.80(m, 1H), 0.92-0.82(m, 2H), 0.70-0.60(m, 1H) |
| 86 | | 9.51(s, 1H), 8.23(d, 1H), 7.93(d, 1H), 7.7-7.5(m, 2H), 6.96(t-like, 1H), 6.26(s, 1H), 4.32(t, 2H), 3.74(dd, 2H), 2.44, 2.07(each s, each 3H) m/z = 368(M + H) |
| 87 | | 9.74(s, 1H), 8.50(d, 1H), 8.10(dd, 1H), 7.80(dd, 1H), 6.92(br-s, 1H), 6.24(br-s, 1H), 6.18(s, 1H), 4.36(dd, 2H), 3.88(br-s, 2H), 2.92(q, 2H), 2.20(s, 3H), 2.12(s, 3H), 1.24(t, 3H) |

TABLE 16-continued

| EX | Structural formula | NMR(ppm) and Mass |
|---|---|---|
| 88 | | 9.51(s, 1H), 7.6-7.1(m, 4H), 6.83(t, 1H), 6.21, 6.16(each s, each, 1H), 4.18(t, 2H), 3.73(dd, 1H), 2.19, 2.03(each s, each 3H) m/z = 374(M + H) |

TABLE 17

| EX | Structural formula | NMR(ppm) and Mass |
|---|---|---|
| 89 | | 9.51(s, 1H), 7.79(dd, 1H), 7.69(t, 1H), 7.54(dd, 1H), 7.41(dd, 1H), 6.85(t, 1H), 6.22, 6.17(each s, each 1H), 4.26(t, 2H), 3.76(dd, 2H), 2.16, 2.14(each s, each s) |
| 90 | | 9.68(s, 1H), 8.12(d, 1H), 7.54(d, 1H), 7.52(dd, 1H), 7.40(dd, 1H), 7.00(br-s, 1H), 6.30(d, 1H), 6.20(s, 1H), 4.20(dd, 2H), 3.72(dd, 2H), 2.06(s, 3H) |
| 91 | | 9.83(s, 1H), 8.84(br-s, 1H), 8.66(br-s, 1H), 7.00-6.80(m, 5H), 6.23(br-s, 2H), 4.11(t, 2H), 3.75(s, 3H), 3.8-3.5(masked, 2H), 3.39(d, 2H), 3.15-2.95(m, 2H), 2.95-2.8(m, 1H), 2.07(s, 3H), 2.00-1.70(m, 4H) |
| 92 | | 10.28(br-s, 1H), 8.54(d, 1H), 8.12(dd, 1H), 7.77(d, 1H), 7.60(d, 1H), 6.96(br-s, 1H), 6.32(d, 1H), 6.21(s, 1H), 4.7-4.58(m, 1H), 4.39(dd, 1H), 4.19(dd, 1H), 2.65(s, 3H), 2.19(s, 3H)1.33(d, 3H) |
| 93 | | 10.32(br-s, 1H), 8.52(d, 1H), 8.11(dd, 1H), 7.76(d, 1H), 6.86(br-s, 1H), 6.26(s, 1H) 6.21(s, 1H), 4.7-4.55(m, 1H), 4.38(dd, 1H) 4.21(dd, 1H), 2.65(s, 3H), 2.24(s, 3H), 2.21(s, 3H), 1.32(d, 3H) m/z = 378(M + H) |

TABLE 17-continued

| EX | Structural formula | NMR(ppm) and Mass |
|---|---|---|
| 94 | | 10.24(br-s, 1H), 9.3-9.1(m, 2H), 8.51(d, 1H) 8.11(dd, 1H), 7.77(d, 1H), 6.77(br-s, 1H), 6.30(br-s, 1H), 6.20(s, 1H), 4.7-4.58(m, 1H), 4.40(dd, 1H), 4.20(dd, 1H), 3.4-3.3(m, 2H) 3.1-2.95(m, 1H), 2.85(s, 3H), 2.18(s, 3H) 1.95-1.75(m, 4H), 1.32(d, 3H) |
| 95 | | 10.00(br-s, 1H), 8.20(br-s, 2H), 7.58(d, 1H), 7.52(d, 1H), 7.44(d, 1H), 7.24(br-s, 1H), 6.74(dd, 1H), 6.32(d, 1H), 6.22(s, 1H), 4.24(dd, 2H), 3.82(br-, 2H), 2.20(s, 3H) |

TABLE 18

| EX | Structural formula | NMR(ppm) and Mass |
|---|---|---|
| 96 | | 9.92(br-s, 1H), 8.54(d, 1H), 8.12(dd, 1H), 7.78(dd, 1H), 7.58(d, 1H), 6.76(br-s, 1H), 6.30(d, 1H), 6.18(s, 1H), 4.64-4.54(m, 1H), 4.34(dd, 2H), 4.12(dd, 2H), 2.62(s, 3H), 2.14(s, 3H), 1.34(d, 3H) |
| 97 | | 10.35(br-s, 1H), 9.22(br-s, 2H), 8.30(s, 1H), 8.17(d, 1H), 7.79(d, 1H), 7.20(br-s, 1H), 6.28(s, 1H), 6.25(s, 1H), 4.41(dd, 2H), 3.81(dd, 2H), 3.40-3.36(m, 2H), 3.04-2.86(m, 3H), 2.68(s, 3H), 2.17(s, 3H), 2.04-1.84(m, 4H) |
| 98 | | 10.12(br-s, 1H), 9.24(br-s, 2H), 8.04(d, 1H), 7.62(d, 1H), 7.08(br-s, 1H), 6.28(s, 1H), 6.20(s, 1H), 4.38(dd, 2H), 3.78(dd, 2H), 3.36-3.32(m, 2H), 3.00-2.82(m, 3H), 2.62(s, 3H), 2.54(s, 3H), 2.16(3H, s), 1.96-1.76(m, 4H) |

TABLE 18-continued
| EX | Structural formula | NMR(ppm) and Mass |
|---|---|---|
| 99 | | 10.24(br-s, 1H), 9.22(br-s, 2H), 8.50(s, 1H), 8.12(d, 1H), 7.78(d, 1H), 7.10(br-s, 1H), 6.30(s, 1H), 6.24(s, 1H), 4.38(dd, 2H), 3.80(dd, 2H), 3.38-3.34(m, 2H), 3.02-2.84(m, 3H), 2.66(s, 3H), 2.18(s, 3H), 2.00-1.80(m, 4H) |
| 100 | | 9.65(s, 1H), 8.25(s, 1H), 8.17(d, 1H), 7.80(d, 1H), 7.52(dd, 1H), 6.90(br-s, 1H), 6.77(s, 1H), 6.22(s, 1H), 4.29(t, 2H), 3.84(m, 2H), 3.15(q, 2H), 2.41(s, 3H), 2.21(s, 3H), 1.48(q, 2H) 0.88(t, 3H) |
| 101 | | 9.50(br-s, 1H), 7.82(d, 1H), 7.40(dd, 1H), 6.88(dd, 1H), 6.80(br-s, 1H), 6.26(br-s, 1H), 6.20(s, 1H), 4.10(dd, 2H), 3.80-3.60(m, 6H), 3.34(dd, 4H), 2.20(s, 3H), 2.08(s, 3H) |
| 102 | | 9.70(br-s, 1H), 9.48(br-s, 1H), 7.90(d, 1H), 7.34(dd, 1H), 6.90(dd, 1H), 6.76(br-s, 1H), 6.20(br-s, 1H), 6.18(s, 1H), 4.20(d, 2H), 4.10(dd, 2H), 3.80-3.64(m, 2H), 3.50-3.40(m, 2H), 3.10-2.94(m, 4H), 2.82(s, 3H), 2.20(s, 3H), 2.06(s, 3H) |
TABLE 19
| EX | Structural formula | NMR(ppm) and Mass |
|---|---|---|
| 103 | 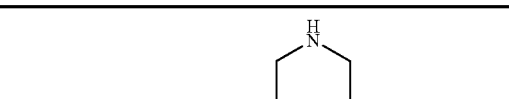 | 10.00(br-s, 1H), 9.10-8.80(m, 2H), 7.28(dd, 1H), 6.96(br-s, 1H), 6.82-6.70(m, 3H), 6.30(s, 1H), 6.26(s, 1H), 4.16(dd, 2H), 3.74(br-s, 2H), 3.40(d, 2H), 3.14-2.86(m, 3H), 2.06(s, 3H), 2.00-1.70(m, 4H) |

TABLE 19-continued
| EX | Structural formula | NMR(ppm) and Mass |
|---|---|---|
| 104 | 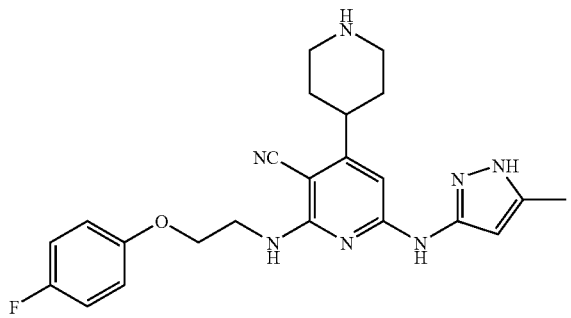 | 9.84(br-s, 1H), 9.00-8.70(m, 2H), 7.08(dd, 2H), 6.92(dd, 2H), 6.30(br-s, 1H), 6.26(s, 1H), 4.10(dd, 1H), 3.74(br-s, 2H), 3.44(d, 2H), 3.16-2.84(m, 3H), 2.08(s, 3H), 1.96-1.74(m, 4H) |
| 105 | 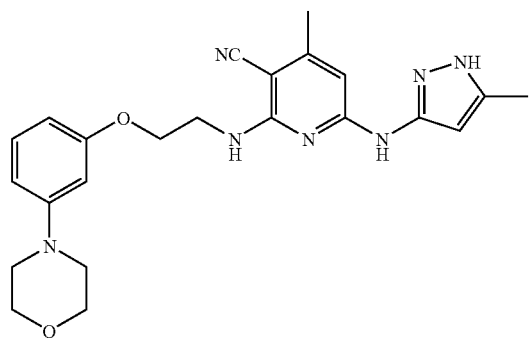 | 10.24(s, 1H), 9.50(s, 1H), 7.08(dd, 1H), 6.80(br-s, 1H), 6.54(d, 1H), 6.46(s, 1H), 6.40(d, 1H), 6.24(br-s, 2H), 4.10(dd, 2H), 3.80-3.60(m, 6H), 3.06(dd, 4H), 2.22(s, 3H), 2.14(s, 3H) |
| 106 | 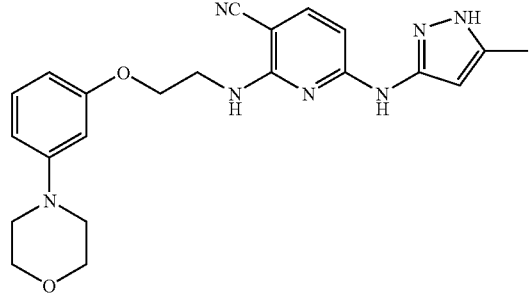 | 9.64(s, 1H), 7.50(d, 1H), 7.08(dd, 1H), 6.90(br-s, 1H), 6.52(d, 1H), 6.46(s, 1H), 6.40(d, 1H), 6.30(br-s, 1H), 6.16(s, 1H), 4.14(dd, 2H), 3.80-3.60(m, 6H), 3.08(dd, 4H), 2.06(s, 3H) |
| 107 | 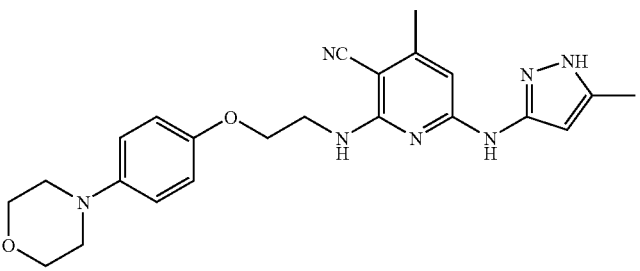 | 9.54(s, 1H), 6.92(d, 2H), 6.88(d, 2H), 6.80(br-s, 1H), 6.20(br-s, 2H), 4.08(dd, 2H), 3.80-3.68(m, 6H), 3.06(br-s, 4H), 2.20(s, 3H), 2.08(s, 3H) |
| 108 | 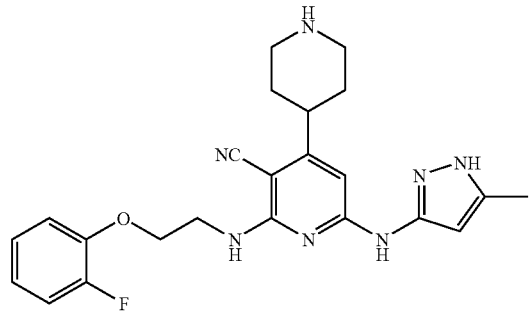 | 9.92(br-s, 1H), 9.00-8.80(m, 2H), 7.24-6.90(m, 5H), 6.30(br-s, 1H), 6.26(s, 1H), 4.20(dd, 2H), 3.80(br-s, 2H), 3.40(d, 2H), 3.14-2.84(m, 3H), 2.08(s, 3H), 2.00-1.76(m, 4H) |

TABLE 19-continued
| EX | Structural formula | NMR(ppm) and Mass |
|---|---|---|
| 109 | 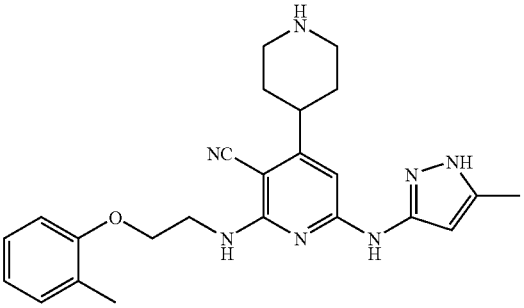 | 10.00(br-s, 1H), 9.06-8.86(m, 2H), 7.14(dd, 2H), 6.96(br-s, 1H), 6.80-6.70(m, 3H), 6.26(br-s, 2H), 4.12(dd, 2H), 3.76(br-s, 2H), 3.38(d, 2H), 3.10-2.86(m, 3H), 2.24(s, 3H), 2.08(s, 3H), 2.00-1.74(m, 4H) |
TABLE 20
| EX | Structural formula | NMR(ppm) and Mass |
|---|---|---|
| 110 | 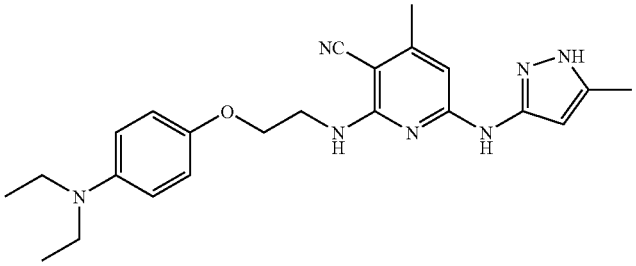 | 9.76(br-s, 1H), 7.50-6.92(m, 5H), 6.24(s, 2H), 4.20(dd, 2H), 3.80(br-s, 2H), 3.60-3.40(m, 4H), 2.20(s, 3H), 2.08(s, 3H), 1.06(t, 6H) |
| 111 | 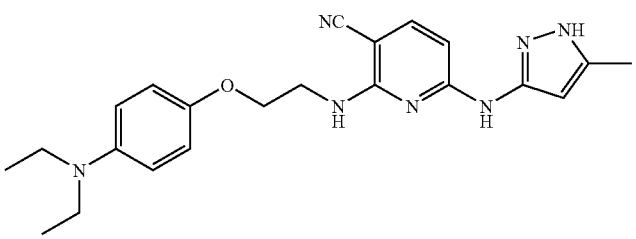 | 9.80(br-s, 1H), 7.54(d, 1H), 7.50-6.96(m, 5H), 6.32(d, 1H), 6.24(s, 1H), 4.20(dd, 2H), 3.80(br-s, 2H), 3.60-3.40(m, 4H), 2.08(s, 3H), 1.00(t, 6H) |
| 112 | 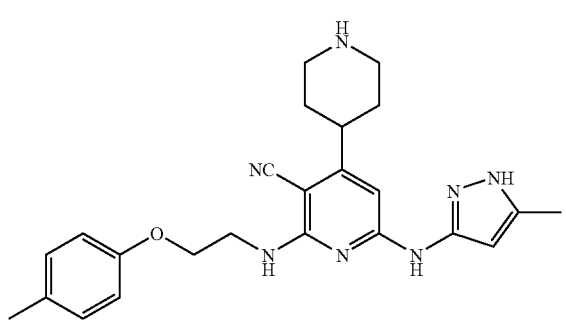 | 9.68(br-s, 1H), 8.70(br-s, 1H), 8.40(br-s, 1H), 7.06(d, 2H), 6.86(br-s, 1H), 6.84(d, 2H), 6.24(br-s, 2H), 4.10(dd, 2H), 3.76(dd, 2H), 3.40(d, 2H), 3.10-2.80(m, 3H), 2.22(s, 3H), 2.06(s, 3H), 2.00-1.68(m, 4H) |
| 113 | 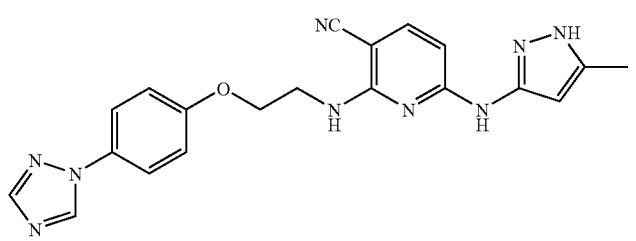 | 9.62(br-s, 1H), 9.15(s, 1H), 8.18(s, 1H), 7.74(d, 2H), 7.52(d, 1H), 7.12(d, 2H), 6.94(br-s, 1H), 6.32(br-s, 1H), 6.24(br-s, 1H), 4.20(dd, 2H), 3.80(dd, 2H), 2.06(s, 3H) |

TABLE 20-continued
| EX | Structural formula | NMR(ppm) and Mass |
|---|---|---|
| 114 | | 9.50(br-s, 1H), 9.16(s, 1H), 8.18(s, 1H), 7.74(d, 2H), 7.12(d, 2H), 6.84(br-s, 1H), 6.24(br-s, 1H), 6.20(br-s, 1H), 4.20(dd, 2H), 3.78(dd, 2H), 2.20(s, 3H), 2.06(s, 3H) |
| 115 | | 9.69(s, 1H), 8.76(br-s, 2H), 7.27(dd, 2H), 7.0-6.8(m, 4H), 6.28(s, 1H), 6.22(s, 1H), 4.52(d, 1H), 4.2-4.1(m, 1H), 4.13(t, 2H), 4.1-3.9(m, 1H), 3.9-3.6(masked, 3H), 3.17(t, 1H), 2.9-2.7(m, 2H), 2.57(t-like, 3H), 2.05(s, 3H), 1.86(d, 2H), 1.6-1.4(m, 2H) |
| 116 | | 9.71(br-s, 2H), 7.27(t-like, 2H), 7.0-6.8(m, 4H), 6.30(s, 1H), 6.23(s, 1H), 4.56(d, 1H), 4.13(t, 2H), 4.1-3.9(m, 1H), 3.9-3.6(masked, 2H), 3.28(m, 2H), 3.15(t, 1H), 3.0-2.8(m, 3H), 2.78(d, 6H), 2.68(t, 1H), 2.06(s, 3H), 1.84(t, 2H), 1.6-1.3(m, 2H) |
TABLE 21
| EX | Structural formula | NMR(ppm) and Mass |
|---|---|---|
| 117 | 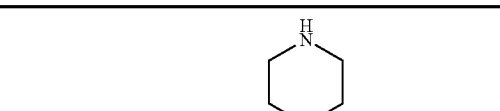 | 9.64(br-s, 1H), 8.68(br-s, 1H), 8.36(br-s, 1H), 7.70-7.28(m, 4H), 6.88(br-s, 1H), 6.20(br-s, 2H), 4.22(dd, 2H), 3.76(dd, 2H), 3.48-3.44(m, 2H), 3.20-2.80(m, 3H), 2.06(s, 3H), 2.00-1.66(m, 4H) m/z = 443(M + H) |

TABLE 21-continued
| EX | Structural formula | NMR(ppm) and Mass |
|---|---|---|
| 118 | 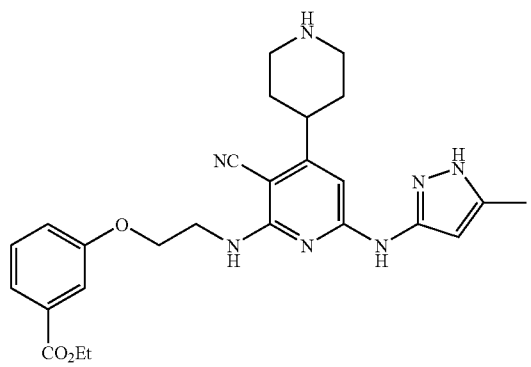 | 9.69(s, 1H), 8.77(br-s, 1H), 8.55(br-s, 1H), 7.6-7.2(m, 4H), 6.91(br-s, 1H), 6.28(br-s, 1H), 6.23(br-s, 1H), 4.30(q, 2H), 4.21(t, 2H), 3.78(m, 2H), 3.6-3.3(masked, 2H), 3.1-3.0(m, 2H), 3.0-2.8(m, 1H), 2.06(s, 3H), 2.0-1.6(m, 4H), 1.30(t, 3H) |
| 119 | 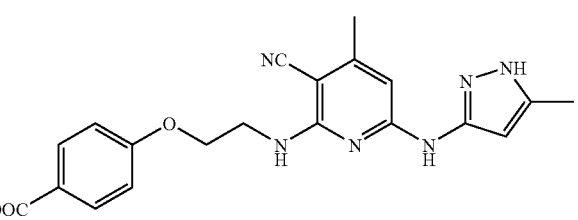 | 11.84(br-s, 1H), 9.48(br-s, 1H), 7.89(d, 2H), 7.06(d, 2H), 6.83(t-like, 1H), 6.32-6.13(m, 2H), 4.22(t, 2H), 3.81(s, 3H), 3.77(q, 2H), 2.19(s, 3H), 2.04(s, 3H) |
| 120 | 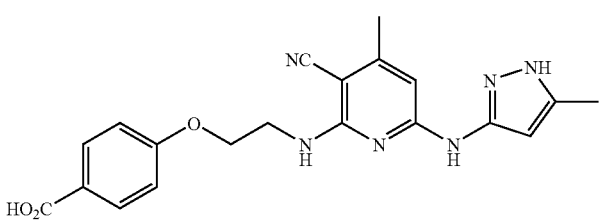 | 7.70(d, 2H), 6.82(d, 2H), 6.76(br-s, 1H), 6.18(br-s, 2H), 4.10(dd, 2H), 3.72(dd, 2H), 2.18(s, 3H), 2.06(s, 3H) |
| 121 | 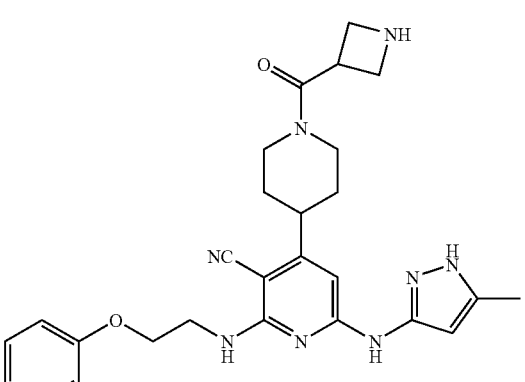 | 11.85(s, 1H), 9.52(s, 1H), 8.74(br-s, 1H) 8.66(br-s, 1H), 7.30(t-like, 2H), 7.0-6.9(m, 3H), 6.82(br-s, 1H), 6.21(br-s, 2H), 4.54(d, 1H), 4.2-4.0(m, 6H), 3.95(m, 1H), 3.76(m, 2H), 3.61(d, 1H), 3.09(t, 1H), 2.9-2.6(m, 2H), 2.04(s, 3H), 1.9-1.7(m, 2H), 1.6-1.3(m, 2H) |
| 122 | 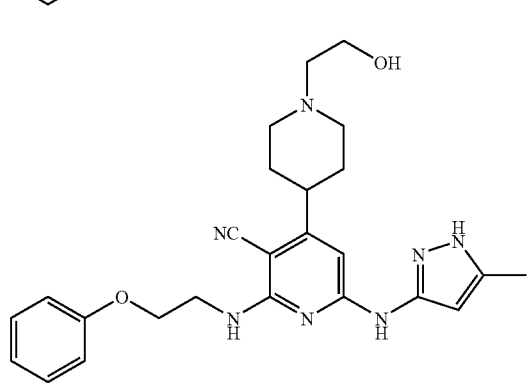 | 11.88(br-s, 1H), 9.66(br-s, 1H), 9.22(br-s, 1H) 7.4-6.9(m, 5H), 6.87(br-s, 1H), .23(br-s, 2H), 5.33(br-s, 1H), 4.13(t, 2H), 3.76(m, 2H), 3.9-3.5(m, 4H), 3.5-3.1(m, 4H), 2.85(m, 1H), 2.05(s, 3H), 2.0-1.8(m, 4H) |

TABLE 21-continued

| EX | Structural formula | NMR(ppm) and Mass |
|---|---|---|
| 123 | | 9.80(br-s, 1H), 7.34(d, 2H), 7.00(d, 2H), 6.94(br-s, 1H), 6.26(br-s, 2H), 4.20(dd, 2H), 3.74(dd, 2H), 2.72(s, 6H), 2.24(s, 3H), 2.10(s, 3H) |

TABLE 22

| EX | Structural formula | NMR(ppm) and Mass |
|---|---|---|
| 124 | | 10.00(s, 1H), 9.06(br-s, 2H), 8.64(d, 1H) 8.46(d, 1H), 8.08(dd, 1H), 7.86(dd, 1H), 7.02(br-s, 1H), 6.31(s, 1H), 6.23(s, 1H), 4.39(t, 2H), 3.82(m, 2H), 3.42-3.35(m, 2H), 3.10-2.95(m, 2H), 2.95-2.85(m, 1H), 2.13(s, 3H), 2.00-1.75(m, 4H) |
| 125 | | 10.21(s, 1H), 9.85(s, 1H), 8.63(d, 1H) 8.44(d, 1H), 8.05(d, 1H), 7.83(dd, 1H), 6.95(br-s, 1H), 6.33(s, 1H), 6.20(s, 1H), 4.55(d, 1H), 4.38(t, 2H), 4.1-3.9(m, 1H), 3.81(m, 2H), 3.27(m, 2H), 3.15(t, 1H), 3.0-2.8(m, 3H), 2.77(d, 6H), 2.67(t, 1H), 2.12(s, 3H), 1.84(t, 2H), 1.6-1.3(m, 2H) |
| 126 | | 9.77(s, 1H), 8.82(br-s, 2H), 8.60(d, 1H) 8.42(d, 1H), 7.99(d, 1H), 7.78(dd, 1H), 6.95(br-s, 1H), 6.31(s, 1H), 6.19(s, 1H), 4.53(d, 1H), 4.36(t, 2H), 4.2-4.1(m, 1H), 4.1-3.9(m, 1H), 3.9-3.7(m, 3H), 3.17(t, 1H), 2.9-2.7(m, 2H), 2.57(t-like, 3H), 2.10(s, 3H), 1.85(d, 2H), 1.6-1.3(m, 2H) |

TABLE 22-continued

| EX | Structural formula | NMR(ppm) and Mass |
|---|---|---|
| 127 | | 10.1(s, 1H), 8.51(d, 1H), 8.11(dd, 1H), 7.9-7.1(m, 1H), 7.61(d, 1H), 7.21(dd, 1H), 7.12(s, 1H), 6.58, 6.21(each s, each 3H) 4.39(t, 2H), 3.84(br-s, 1H), 2.48, 2.14(each s, each 3H), m/z = 432(M + H) |
| 128 | | 9.55(s, 1H), 8.44(d, 1H), 7.93(dd, 1H), 7.64(d, 1H), 6.85(t, 1H), 6.26(s, 2H), 4.32(s, 2H), 4.30(t, 2H), 3.77(dd, 2H), 2.54, 2.17(each s,each 3H) m/z = 380(M + H) |
| 129 | | 9.72(s, 1H), 8.48(s, 1H), 7.34(d, 1H), 6.99(dd, 1H), 6.86(br-s, 1H), 6.40, 6.09(each s,each 1H), 4.14(t, 2H), 3.66(dd, 2H), 2.26, 2.18, 2.10(each s, each 3H) m/z = 380(M + H) |

Pharmacological Experimental Example 1

Aurora 2 Kinase Activity Inhibitory Action (1) Preparation of Aurora 2 Kinase

Total RNA was extracted from HeLa cells (ATCC No. CCL-2) by a conventional method, and cDNA was synthesized by a reverse transcriptase reaction. Using the cDNA as a template, PCR reaction was performed. The primer sequences subjected to the PCR reaction were SEQ ID NO: 1 (5'-GGA ATT CCA TAT GGA CCG ATC TAA AGA AAA CTG-3') and SEQ ID NO: 2 (5'-GGG GGG CTC GAG AGA CTG TTT GCT AGC TGA TTC-3').

The sequence obtained by the PCR reaction was the same as the sequence of the aurora 2 kinase coding gene reported in the reference cited earlier (The EMBO Journal Vol. 17 No. 11 p 3052-3065 1998).

The amplified gene encoding aurora 2 kinase was introduced into *Escherichia coli* expression vector pET32a (manufactured by Novagen) to give a recombinant. The recombinant can be obtained according to Sambrook et al., "Molecule Cloning-Experiment Manual, second ed. (1989 Cold Spring Harbor Laboratory press)", and Ausubel et al., "Current Protocols in Molecular Biology, (1999 John Wiley and Sons Inc.)".

Thereafter, the recombinant was introduced into protein overexpression *Escherichia coli* BL21R strain (Novagen) to give *Escherichia coli* strain for aurora 2 kinase overexpression.

The *Escherichia coli* strain for aurora 2 kinase overexpression was cultured in LB medium containing Ampicilin (50 ug/ml). After shaking culture at 37° C. for 1 hr, to induce expression of aurora 2 kinase, the culture temperature was set to 25° C., IPTG (SIGMA) was added at the final concentration of 0.1 mM, and shaking culture was performed at 25° C. for 24 hr. Thereafter, the culture medium was centrifuged at 7000 rpm for 10 min and the fungus bodies were collected.

The collected fungus bodies were suspended in 36 ml of lysis buffer [50 mM Tris pH 6.8, 150 mM NaCl, 20 mM β-Glycerophosphate, 0.3 mM Na3VO4, 50 mM NaF, 2 mM PMSF (phenylmethylsulfonyl fluoride), 1 tablet protease inhibitor cocktail (Boehringer Mannheim)] and disrupted by ultrasonication. Furthermore, to dissociate non-specific binding between proteins, 4 ml of 10% NP-40 (Wako Pure Chemical Industries, Ltd.) was added.

Then, recombinant aurora 2 kinase in the buffer was adsorbed onto Ni-NTA agarose beads (QIAGEN), and the beads carrying recombinant aurora 2 kinase were washed with 50 ml of K buffer (1M KCl/1×TNT), G buffer (30% Glycerol, 0.5M KCl/1×TNT) to give aurora 2 kinase.

(2) Aurora 2 Kinase Assay

An enzyme reaction buffer (200 mM Tris-HCl (pH 7.0), 100 mM MgCl2) (1.5 μl), 50 mM dithiothreitol (1.5 μl), 1 mM peptide substrate [LRRASLG] (1.5 μl), water (2.5 μl) and a DMSO solution (1.5 μl) containing the compound were added to each well.

The aurora 2 kinase (1 mg/ml) (1.5 μl) diluted with an enzyme dilution buffer [50 mM Tris-HCl (pH 6.8), 200 mM NaCl, 50% glycerol, 1 mg/ml BSA] was added to all the wells except "blank" well. An enzyme dilution buffer (1.5 μl) free of aurora 2 kinase was added to the "blank" well. To the "total" well was added DMSO solution (1.5 µl) without the compound.

Then, 28 µM ATP solution (5 ul) containing 1.2µ Ci [(γ-32P)ATP (Muromachi Yakuhin, specific activity >3500 Ci/mmol)] was added to all test wells, followed by incubation at room temperature for 60 min. The reaction mixture (5 µl) was spotted on a phosphocellulose (Wattman, p 81) filter to allow adsorption of phosphorylated 32P-labeled peptide on the filter. The filter was washed 4 times with 0.75% phosphoric acid solution, unreacted product was removed and reacted $^{32}P$ was counted using BAS5000 (FUJI FILM).

The count of the "blank" (no enzyme) was taken as 0%, and the count of the "total" (no compound) was taken as 100%. Using these control values, the Ki value of the enzyme inhibitory activity was determined.

(3) Evaluation Results

The compound was evaluated according to the operation procedure of (2) aurora 2 kinase assay mentioned above. As a result, it was confirmed that the compound of the formula (I) of the present invention inhibited the aurora 2 kinase activity.

The results have revealed that the compounds of the Examples of the present invention show a strong aurora 2 kinase activity inhibitory action.

TABLE 23

| test substance | Ki (µM) | test substance | Ki (µM) | test substance | Ki (µM) |
| --- | --- | --- | --- | --- | --- |
| Example 1 | 0.019 | Example 2 | 0.003 | Example 3 | 0.015 |
| Example 4 | 0.015 | Example 5 | 0.026 | Example 6 | 0.003 |
| Example 7 | 0.006 | Example 8 | 0.006 | Example 9 | 0.001 |
| Example 10 | 0.003 | Example 11 | 0.024 | Example 12 | 0.002 |
| Example 13 | 0.002 | Example 14 | 0.003 | Example 15 | 0.002 |
| Example 16 | 0.003 | Example 17 | 0.002 | Example 18 | 0.002 |
| Example 19 | 0.001 | Example 20 | 0.002 | Example 21 | 0.002 |
| Example 22 | 0.004 | Example 23 | 0.010 | Example 24 | 0.001 |
| Example 25 | 0.002 | Example 26 | 0.013 | Example 27 | 0.003 |
| Example 28 | 0.004 | Example 29 | 0.066 | Example 30 | 0.080 |

Pharmacological Experimental Example 2

Aurora 1 Kinase Activity Inhibitory Action (1) Aurora 1 Kinase Assay

An enzyme reaction buffer (200 mM Tris-HCl (pH 7.0), 100 mM MgCl2) (1.5 µl), 50 mM dithiothreitol (5 µl), 1 mM peptide substrate [LRRWSLG] (1.5 µl), water (4.83 µl) and a DMSO solution (1.5 µl) containing the compound were added to each well.

A 0.6 mg/ml enzyme solution (UPSTATE) (0.17 µl) was added to all the wells except "blank" well. Water (0.17 µl) free of aurora 2 kinase was added to the "blank" well. To the "total" well was added DMSO solution (1.5 µl) without the compound.

Then, 24 µM ATP solution (5 µl) containing 1.2 µCi [(γ-32P)ATP (Muromachi Yakuhin, specific activity >3500 Ci/mmol)] was added to all test wells, followed by incubation at room temperature for 60 min. The reaction mixture (5 µl) was spotted on a phosphocellulose (Wattman, p 81) filter to allow adsorption of phosphorylated 32P-labeled peptide on the filter. The filter was washed 4 times with 0.75% phosphoric acid solution, unreacted product was removed and reacted $^{32}P$ was counted using BAS5000 (FUJI FILM).

The count of the "blank" (no enzyme) was taken as 0%, and the count of the "total" (no compound) was taken as 100%. Using these control values, the Ki value of the enzyme inhibitory activity was determined.

(2) Evaluation Results

The compound was evaluated according to the operation procedure of (1) aurora 1 kinase assay mentioned above. As a result, it was confirmed that the compound of the formula (I) of the present invention inhibited the aurora 1 kinase activity.

The following compounds showed Ki of 0.1 µM or below. Example 2, Example 12, Example 13, Example 21, Example 25, Example 27, Example 28, Example 34, Example 35.

Pharmacological Experimental Example 3

Tubulin Polymerization Inhibitory Action (1) Tubulin Polymerization Assay

A tubulin polymerization reaction mixture (50 µL) (80 mM Pipes pH=6.9, 0.5 mM MgCl2, 1 mM EGTA, 1 mM GTP, 3.3 mg/ml Porcine brain tubulin protein: Cytoskeleton, 10 µM compound) was prepared in a 96 well flat bottom plate under ice-cooling. This was placed in a plate reader (IWAKI microplate reader, EZS-ABS) controlled to a temperature of 37° C., whereby a temperature dependent tubulin polymerization reaction was initiated. Since the turbidity of the reaction mixture increases as the tubulin polymerization proceeds, the absorbance at 405 nm was measured every other minute for 30 min to monitor the polymerization reaction. Of the 30 min measures, the three largest differences per min of turbidity (generally those immediately after start of the reaction) were taken, and the average of the three values was calculated and taken as the maximum polymerization rate. Inhibitory percent (%)=(C−T)/C×100 wherein T is the maximum polymerization rate of the reaction mixture containing the compound, and C is the maximum polymerization rate of the reaction mixture without the compound.

(2) Evaluation Results

The compounds were evaluated according to the aforementioned operation procedures and, as a result, the compound of the formula (I) of the present invention was confirmed to have inhibited tubulin polymerization. Combined with the earlier evaluation results of the aurora kinase inhibitory activity, it was clarified that the compounds of the Examples of the present invention showed a dual inhibitory activity of aurora kinase and tubulin polymerization.

TABLE 24

| test substance | inhibitory rate (%) |
| --- | --- |
| Example 1 | 51 |
| Example 2 | 69 |
| Example 3 | 36 |
| Example 4 | 63 |
| Example 5 | 51 |
| Example 6 | <0 |
| Example 7 | 63 |
| Example 8 | 42 |
| Example 9 | 86 |
| Example 10 | 44 |
| Example 11 | 42 |
| Example 12 | 44 |

TABLE 24-continued

| test substance | inhibitory rate (%) |
|---|---|
| Example 13 | 69 |
| Example 14 | 55 |
| Example 15 | 69 |
| Example 16 | 65 |
| Example 17 | 67 |
| Example 18 | 79 |
| Example 19 | 59 |
| Example 20 | 75 |
| Example 21 | 63 |
| Example 22 | 79 |
| Example 23 | 77 |
| Example 24 | 73 |
| Example 25 | 51 |
| Example 26 | 48 |
| Example 27 | 57 |
| Example 28 | 69 |
| Example 29 | 42 |
| Example 30 | 34 |

Pharmacological Experimental Example 4

Cancer Cell Growth Inhibitory Effect

Using RPMI1640 medium (manufactured by SIGMA) containing 10% fetal bovine serum, human prostate cancer cell line PC-3, human pancreatic cancer cell line PK-8, and human breast cancer cell line MDA-MB-453 were cultured at 37° C. under 5% $CO_2$. Using DMEM/F-12 medium (manufactured by SIGMA) containing 10% fetal bovine serum, human colon cancer cell line HCT-116, human colon cancer cell line SW620, human ovarian cancer cell line SKOV-3, human prostate cancer cell line DU-145 and human pancreatic cancer cell line PANC-1 were cultured at 37° C. under 5% $CO_2$. These cells were inoculated to a 96 well plate and cultured for one day. Thereto was added a compound diluted with a medium to a final concentration of 0.00064-20 µM (final DMSO concentration, 0.4%). After further cultivation for 3 days, WST-8 (0.16 mg/mL) was added to the culture medium and the culture medium was cultured for 2 hr. The absorbance at 650 nm was subtracted from the absorbance at 450 nm. The growth inhibitory activity was expressed by the decrease rate of the absorbance of compound addition group relative to the absorbance of compound non-addition group, and $IC_{50}$ value was determined from the dose-reaction curve plotting the decrease rate of the absorbance, which was obtained by changing the concentration of the compound, and the concentration of the compound. The values are shown in the Table.

The Examples 12, 21, 22 and 23 of the present invention showed a good cancer cell growth inhibitory action over a broad range.

TABLE 25

| Cell proliferation suppressive activity value IC50 [nM] | | | | |
|---|---|---|---|---|
| | cell line | | | |
| No. | HCT116 | SW620 | PC3 | SKOV3 |
| Example 2 | 11 | 8 | 17 | 10 |
| Example 9 | 17 | <6.4 | <6.4 | <6.4 |
| Example 12 | 2 | <6.4 | 7 | 1 |
| Example 21 | 7 | 5 | 4 | 3 |
| Example 22 | 4 | <6.4 | 15 | 4 |

TABLE 25-continued

| Cell proliferation suppressive activity value IC50 [nM] | | | | |
|---|---|---|---|---|
| Example 23 | 37 | 40 | 21 | 8 |
| Example 28 | 3 | <6.4 | <6.4 | <6.4 |
| | cell line | | | |
| No. | PK8 | DU145 | MDAMB-453 | PANC-1 |
| Example 2 | 18 | 7 | 7 | 1292 |
| Example 9 | 83 | 647 | <6.4 | 1179 |
| Example 12 | 4 | 7 | 3 | 9 |
| Example 21 | 8 | 13 | 12 | 14 |
| Example 22 | 7 | 8 | <6.4 | <6.4 |
| Example 23 | 13 | 50 | 40 | 3 |
| Example 28 | <6.4 | 19 | 4 | 6176 |

(<6.4 in the Tables shows that the IC50 value is less than 6.4 nM)

INDUSTRIAL APPLICABILITY

According to the present invention, a therapeutic drug for cancer containing a substance selected from the group consisting of a novel cyanopyridine derivative, a pharmaceutically acceptable salt, a hydrate, a water adduct and a solvate as an active ingredient can be provided.

This application is based on a patent application No. 2005-131498 filed in Japan, the contents of which are incorporated in full herein by this reference.

The invention claimed is:

1. A cyanopyridine compound represented by the formula (I)

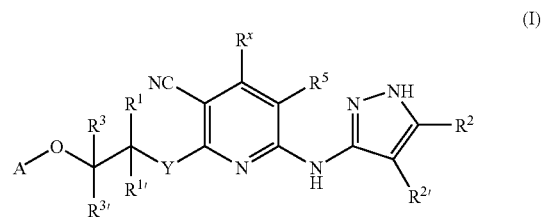

wherein $R^1$, $R^{1\prime}$, $R^3$, $R^{3\prime}$ and $R^5$ are each a hydrogen atom, a halogen atom or alkyl optionally substituted with substituent(s) selected from the group consisting of a halogen atom, $C_{1-6}$ alkyl, haloalkyl, cyano, nitro, hydroxy, $C_{1-6}$ alkoxy, mercapto, $C_{1-6}$ alkylthio, amino and $C_{1-6}$ alkylamino, $R^2$ is a hydrogen atom, a hydroxyl group, alkyl optionally substituted with substituent(s) selected from the group consisting of a halogen atom, $C_{1-6}$ alkyl, haloalkyl, cyano, nitro, hydroxy, $C_{1-6}$ alkoxy, mercapto, $C_{1-6}$ alkylthio, amino and $C_{1-6}$ alkylamino, alkoxy, hydroxyalkyl, alkylthio, carbamoyl, alkanoylamino or amine, $R^{2\prime}$ is a hydrogen atom or alkyl optionally substituted with substituent(s) selected from the group consisting of a halogen atom, $C_{1-6}$ alkyl, haloalkyl, cyano, nitro, hydroxy, $C_{1-6}$ alkoxy, mercapto, $C_{1-6}$ alkylthio, amino and $C_{1-6}$ alkylamino, Y is N—$R^4$ or S, $R^4$ is a hydrogen atom or alkyl optionally substituted with substituent(s) selected from the group consisting of a halogen atom, $C_{1-6}$ alkyl, haloalkyl, cyano, nitro, hydroxy, $C_{1-6}$ alkoxy, mercapto, $C_{1-6}$ alkylthio, amino and $C_{1-6}$ alkylamino, A is 3-pyridyl optionally substituted with substituent(s) selected from the group consisting of a halogen atom, $C_{1-6}$ alkyl, haloalkyl, cyano, nitro, hydroxy, $C_{1-6}$ alkoxy, mercapto, $C_{1-6}$ alkylthio, amino, $C_{1-6}$ alkylamino, $C_{2-6}$ alkanoylamino, $C_{1-6}$ alkanesulfonylamino, 5- to 7-membered cyclic compound, carboxyl, carbamoyl and alkylcarbonyl, $R^x$ is -T-$R^4$, T is a valence bond or a $C_{1-4}$ alkylene chain, and $R^4$ is —R, a halogen atom, —OR or —$NR_2$ wherein R is a hydrogen atom, alkyl optionally substituted with substituent(s) selected from the group consisting of a halogen atom, $C_{1-6}$ alkyl, haloalkyl, cyano, nitro, hydroxy, $C_{1-6}$ alkoxy, mercapto, $C_{1-6}$ alkylthio, amino and $C_{1-6}$ alkylamino, or aryl optionally substituted with substituent(s) selected from the group consisting of a halogen atom, $C_{1-6}$ alkyl, haloalkyl, cyano, nitro, hydroxy, $C_{1-6}$ alkoxy, mercapto, $C_{1-6}$ alkylthio, amino, $C_{1-6}$ alkylamino, $C_{2-6}$ alkanoylamino, $C_{1-6}$ alkanesulfonylamino, 5- to 7-membered cyclic compound, carboxyl, carbamoyl and alkylcarbonyl, or a pharmaceutically acceptable salt thereof.

2. The cyanopyridine compound of claim 1, wherein, in the above-mentioned formula (I), T is a valence bond, $R^4$ is hydrogen, alkyl optionally substituted with substituent(s) selected from the group consisting of a halogen atom, $C_{1-6}$ alkyl, haloalkyl, cyano, nitro, hydroxy, $C_{1-6}$ alkoxy, mercapto, $C_{1-6}$ alkylthio, amino and $C_{1-6}$ alkylamino, or aryl optionally substituted with substituent(s) selected from the group consisting of a halogen atom, $C_{1-6}$ alkyl, haloalkyl, cyano, nitro, hydroxy, $C_{1-6}$ alkoxy, mercapto, $C_{1-6}$ alkylthio, amino, $C_{1-6}$ alkylamino, $C_{2-6}$ alkanoylamino, $C_{1-6}$ alkanesulfonylamino, 5- to 7-membered cyclic compound, carboxyl, carbamoyl and alkylcarbonyl, or a pharmaceutically acceptable salt thereof.

3. The cyanopyridine compound of claim 1, wherein, in the above-mentioned formula (I), $R^4$ is hydrogen, alkyl, or phenyl, or a pharmaceutically acceptable salt thereof.

4. A pharmaceutical composition comprising a cyanopyridine compound of claim 1, or a pharmaceutically acceptable salt thereof, as an active ingredient and a pharmaceutically acceptable carrier, excipient or diluent.

5. The cyanopyridine compound of claim 2, wherein, in the above-mentioned formula (I), $R^4$ is hydrogen, alkyl, or phenyl, or a pharmaceutically acceptable salt thereof.

6. A pharmaceutical composition comprising a cyanopyridine compound of claim 2, or a pharmaceutically acceptable salt thereof, as an active ingredient and a pharmaceutically acceptable carrier, excipient or diluent.

7. A pharmaceutical composition comprising a cyanopyridine compound of claim 3, or a pharmaceutically acceptable salt thereof, as an active ingredient and a pharmaceutically acceptable carrier, excipient or diluent.

8. The cyanopyridine compound of claim 1, which is a compound selected from the group consisting of:
- 2-(2-(pyridin-3-yloxy)ethylamino)-6-(5-methyl-1H-pyrazol-3-ylamino)-4-methylnicotinonitrile;
- 2-(2-(6-methylpyridin-3-yloxy)ethylamino)-6-(5-methyl-1H-pyrazol-3-ylamino)-4-methylnicotinonitrile;
- 2-(2-(2-methylpyridin-3-yloxy)ethylamino)-6-(5-methyl-1H-pyrazol-3-ylamino)-4-methylnicotinonitrile;
- 2-(2-(2,6-dimethylpyridin-3-yloxy)ethylamino)-6-(5-methyl-1H-pyrazol-3-ylamino)-4-methylnicotinonitrile; and
- 2-(2-(2-methylpyridin-3-yloxy)ethylamino)-6-(5-methyl-1H-pyrazol-3-ylamino)nicotinonitrile;

or a pharmaceutically acceptable salt thereof.

9. A pharmaceutical composition comprising a cyanopyridine compound of claim 8, or a pharmaceutically acceptable salt thereof, as an active ingredient and a pharmaceutically acceptable carrier, excipient or diluent.

* * * * *